US012702122B2

(12) United States Patent
Brydges et al.

(10) Patent No.: US 12,702,122 B2
(45) Date of Patent: Aug. 11, 2026

(54) NON-HUMAN ANIMALS COMPRISING A HUMANIZED ACE2 LOCUS

(71) Applicant: Regeneron Pharmaceuticals, Inc., Tarrytown, NY (US)

(72) Inventors: Susannah Brydges, Scarsdale, NY (US); Christos Kyratsous, Irvington, NY (US); Alina Baum, Pleasantville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 739 days.

(21) Appl. No.: 18/002,228

(22) PCT Filed: Jun. 25, 2021

(86) PCT No.: PCT/US2021/039162

§ 371 (c)(1),
(2) Date: Dec. 16, 2022

(87) PCT Pub. No.: WO2021/263146

PCT Pub. Date: Dec. 30, 2021

(65) Prior Publication Data

US 2023/0232796 A1 Jul. 27, 2023

Related U.S. Application Data

(60) Provisional application No. 63/093,994, filed on Oct. 20, 2020, provisional application No. 63/093,892, filed on Oct. 20, 2020, provisional application No. 63/045,183, filed on Jun. 28, 2020, provisional application No. 63/044,976, filed on Jun. 26, 2020.

(51) Int. Cl.

| | |
|---|---|
| ***A01K 67/0278*** | (2024.01) |
| ***A61K 49/00*** | (2006.01) |
| ***C12N 9/48*** | (2006.01) |
| ***C12N 15/90*** | (2006.01) |

(52) U.S. Cl.
CPC ...... *A01K 67/0278* (2013.01); *A61K 49/0008* (2013.01); *C12N 9/485* (2013.01); *C12N 15/907* (2013.01); *C12Y 304/17023* (2013.01); *A01K 2207/15* (2013.01); *A01K 2217/072* (2013.01); *A01K 2227/105* (2013.01); *A01K 2267/0337* (2013.01)

(58) Field of Classification Search
CPC ............ A01K 67/0278; A01K 2207/15; A01K 2217/072; A01K 2227/105; A01K 2267/0337; A61K 49/0008; C12N 9/485; C12N 15/907; C12Y 304/17023
See application file for complete search history.

(56) References Cited

U.S. PATENT DOCUMENTS

| | | | |
|---|---|---|---|
| 6,586,251 | B2 | 7/2003 | Economides et al. |
| 7,294,754 | B2 | 11/2007 | Poueymirou et al. |
| 7,576,259 | B2 | 8/2009 | Poueymirou et al. |
| 7,612,250 | B2 | 11/2009 | Overstrom et al. |
| 7,659,442 | B2 | 2/2010 | Poueymirou et al. |
| 8,232,447 | B2 | 7/2012 | Argane et al. |
| 8,586,713 | B2 | 11/2013 | Davis et al. |
| 8,697,851 | B2 | 4/2014 | Frendewey et al. |
| 2004/0177390 | A1 | 9/2004 | Lewis et al. |
| 2005/0144655 | A1 | 6/2005 | Economides et al. |
| 2008/0078001 | A1 | 3/2008 | Poueymirou et al. |
| 2008/0092249 | A1 | 4/2008 | Lewis et al. |
| 2011/0104799 | A1 | 5/2011 | Economides et al. |
| 2013/0309670 | A1 | 11/2013 | Frendewey et al. |
| 2013/0312129 | A1 | 11/2013 | Frendewey et al. |
| 2014/0178879 | A1 | 6/2014 | Economides et al. |
| 2014/0235933 | A1 | 8/2014 | Lee et al. |
| 2015/0159175 | A1 | 6/2015 | Frendewey et al. |
| 2016/0145646 | A1 | 5/2016 | Frendewey et al. |

FOREIGN PATENT DOCUMENTS

| | | | |
|---|---|---|---|
| CN | 111979273 | A | 11/2020 |
| WO | 1999/005266 | A2 | 2/1999 |
| WO | 2006/052691 | A2 | 5/2006 |
| WO | 2008/017234 | A1 | 2/2008 |
| WO | 2008/045120 | A2 | 4/2008 |
| WO | 2013/176772 | A1 | 11/2013 |
| WO | 2014/033644 | A2 | 3/2014 |
| WO | 2014/089290 | A1 | 6/2014 |
| WO | 2015/184164 | A1 | 12/2015 |
| WO | 2016/081923 | A2 | 5/2016 |

OTHER PUBLICATIONS

Gretebeck, Lisa M. et al. Current opinion in virology 13 (2015): 123-129 (Year: 2015).*

Li, Wenhui, et al. The EMBO journal 24.8 (2005): 1634-1643 (Year: 2005).*

Yang, Xiu-hong, et al. Comparative medicine 57.5 (2007): 450-459 (Year: 2007).*

Roebroek, Anton JM, et al. Transgenic Mouse Methods and Protocols. Totowa, NJ: Humana Press, 2010. 257-275. (Year: 2010).*

Bao et al., "The pathogenicity of SARS-CoV-2 in hACE2 transgenic mice," Nature 583:830-833, 2020.

(Continued)

*Primary Examiner* — Marcia S Noble
*Assistant Examiner* — Zanna Maria Beharry
(74) *Attorney, Agent, or Firm* — FisherBroyles, LLP; Rita S. Wu; Elysa Goldberg

(57) ABSTRACT

Non-human animal cells and non-human animals comprising a humanized ACE2 locus and methods of using such non-human animal cells and non-human animals are provided. Non-human animal cells or non-human animals comprising a humanized ACE2 locus express a human ACE2 protein or a chimeric ACE2 protein, fragments of which are from human ACE2. Methods are also provided for using such non-human animals comprising a humanized ACE2 locus to assess in vivo ACE2 activity, e.g., coronavirus infection and/or the treatment or prevention thereof.

14 Claims, 20 Drawing Sheets

Specification includes a Sequence Listing.

(56) References Cited

OTHER PUBLICATIONS

Chen et al., "Elevated ACE-2 expression in the olfactory neuroepithelium: implications for anosmia and upper respiratory SARS-CoV-2 entry and replication," Eur Respir Journal 56:2001948, 2020 https://doi.org/10.1183/13993003.01948-2020.
Cho et al., "Generation of Transgenic Mice," Current Protocols in Cell Biology 42:19.11.1-19.11.22, 2009, Author Manuscript.
Dinnon, III, et al., "A mouse-adapted model of SARS-CoV-2 to test COVID-19 countermeasures," Author Manuscript, Nature 586(7830):560-566, 2020 doi: 10.1038/s41586-020-2708-8.
Festing et al., "Revised nomenclature for strain 129 mice," Mammalian Genome 10:836, 1999.
Frendewey et al., "The Loss-of-Allele Assay for ES Cell Screening and Mouse Genotyping," Methods in Enzymology 476:295-307, 2010.
Gama Sosa et al., "Animal transgenesis: an overview," Brain Struct. Funct. 214:91-109, 2010.
GenBank Accession No. NP-001123985.1 (4 Pages) (Jan. 16, 2024).
GenBank Accession No. NM_001130513.1 (6 Pages) (Jan. 16, 2024).
GenBank Accession No. NM_021804.3 (7 Pages) (Jan. 15, 2024).
GenBank Accession No. NP-068576.1 (5 Pages) (Jan. 15, 2024).
Gorbalenya et al., "The species Severe acute respiratory syndrome-related coronavirus: classifying 2019-nCoV and naming it SARS-CoV-2," Nat Microbiol 5: 536-544, 2020 https://doi.org/10.1038/s41564-020-0695-z.
Hamming et al., "Tissue distribution of ACE2 protein, the functional receptor for SARS coronavirus. A first step in understanding SARS pathogenesis," Journal of Pathology 2004(203):631-637, 2004 DOI: 10.1002/path.1570.
Jiang et al., "Pathogenesis of SARS-CoV-2 in Transgenic Mice Expressing Human Angiotensin- Converting Enzyme 2," Cell 182:50-58, 2020 https://doi.org/10.1016/j.cell.2020.05.027.
Kasparek and Humphrey, "DNA double-strand break repair pathways, chromosomal rearrangements and cancer," Seminars in Cell & Developmental Biology 22:886-897, 2011.
Le Bras, A., "Modeling SARS-CoV-2 infection in mice," Lab Animal, 49:198, 2020.
Liu et al., "Epithelial Cells Lining Salivary Gland Ducts Are Early Target Cells of Severe Acute Respiratory Syndrome Coronavirus Infection in the Upper Respiratory Tracts of Rhesus Macaques," Journal of Virology, 85(8):4025-4030, 2011 doi:10.1128/JVI.02292-10.
Lu et al., "US CDC Real-Time Reverse Transcription PCR Panel for Detection of Severe Acute Respiratory Syndrome Coronavirus 2. Emerging Infectious Diseases," 26(8):1654-1665, 2020 doi:10.3201/eid2608.201246.
Mandalos et al., "Application of a Novel Strategy of Engineering Conditional Alleles to a Single Exon Gene, Sox2," Plos One, 7(9)e45768:1-9, 2012.
Maresca et al., "Obligate Ligation-Gated Recombination (ObLiGaRe): Custom-designed nuclease-mediated targeted integration through nonhomologous end joining," Genome Research, 23:539-546, 2013.
Mccray et al., "Lethal Infection of K18-hACE2 Mice Infected with Severe Acute Respiratory Syndrome Coronavirus," Journal of Virology, 81(2):813-821, 2007 doi:10.1128/JVI.02012-06.
Morris, Glenn E., "Epitope Mapping of Protein Antigens by Competition ELISA," The Protein Protocols Handbook, Totowa, NJ, Humana Press (Jan. 1, 1996):595-600, 1996.
Nakamura et al., "Codon usage tabulated from international DNA sequence databases: status for the year 2000," Nucleic Acids Research, 28:292, 2000.
Orman et al., "Detection of 2019 novel coronavirus (2019-nCoV) by real-time RT-PCR," Euro Surveill 25(3), 2020.
Poueymirou et al., "FO generation mice fully derived from gene-targeted embryonic stem cells allowing immediate phenotypic analyses," Nature Biotechnology 25(1):91-99, 2007.
Sato et al., "Expression of ACE2 and TMPRSS2 proteins in the upper and lower aerodigestive tracts of rats," BioRxiv Preprint, Author Manuscript, 1-17, 2020 https://doi.org/10.1101/2020.05.14.097204.
Smith et al., "Cigarette Smoke Exposure and Inflammatory Signaling Increase the Expression of the SARS-CoV-2 Receptor ACE2 in the Respiratory Tract," Developmental Cell 53:514-529, 2020 https://doi.org/10.1016/j.devcel.2020.05.012.
Smith et al., "Cigarette smoke triggers the expansion of a subpopulation of respiratory epithelial cells that express the SARS-CoV-2 receptor ACE2," bioRxiv, 2020 doi:https://doi.org/10.1101/2020.03.28.013672.
Song et al., "Ontogeny of angiotensin-converting enzyme 2," Pediatric Research, Nature 71(1):13-19, 2012 doi: 10.1038/pr.2011.7.
Subbarao and Roberts, "Is there an ideal animal model for SARS?" Trends in Microbiology, 14(7):299-303, 2006.
Sun et al., "A Mouse Model of SARS-CoV-2 Infection and Pathogenesis," Cell Host & Microbe, 28:1-10, 2020 https://doi.org/10.1016/j.chom.2020.05.020.
Sun et al., "A Mouse Model of SARS-CoV-2 Infection and Pathogenesis," Cell Host & Microbe, 28:124-133, 2020.
Tostanoski et al., "Ad26 vaccine protects against SARS-CoV-2 severe clinical disease in hamsters," nature medicine, 26:1694-1700, 2020 https://doi.org/10.1038/s41591-020-1070-6.
UniProt Accession No. Q9BYF1-1 (16 Pages) (Jan. 18, 2024).
UniProt Accession No. Q8R010-1 (12 Pages) (Jan. 18, 2024).
Varga et al., "Endothelial cell infection and endotheliitis in COVID-19," Lancet 395(10234): 1417-1418, 2020 doi: 10.1016/S0140-6736(20)30937-5.
Wan et al., "Receptor Recognition by the Novel Coronavirus from Wuhan: an Analysis Based on Decade-Long Structural Studies of SARS Coronavirus," Journal of Virology, 94(7):1-9, 2020.
Wang et al., "One-Step Generation of Mice Carrying Mutations in Multiple Genes by CRISPR/Cas-Mediated Genome Engineering," Cell, 153:910-918, 2013.
Wang et al., "TALEN-mediated editing of the mouse Y chromosome," Nature Biotechnology, 31(6): 530-532, 2013.
Wiener et al., "Angiotensin Converting Enzyme 2 is Primarily Epithelial and Is Developmentally Regulated in the Mouse Lung," Journal of Cellular Biochemistry 101:1278-1291, 2007 DOI 10.1002/jcb.21248.
Wolfel et al., "Virological assessment of hospitalized patients with COVID-2019," Nature 581:465-469, 2020 https://doi.org/10.1038/s41586-020-2196-x.
Wu et al., "A new coronavirus associated with human respiratory disease in China," Nature 579:265-269, 2020 https://doi.org/10.1038/s41586-020-2008-3.
Zhang et al., "Specific ACE2 expression in small intestinal enterocytes may cause gastrointestinal symptoms and injury after 2019-nCoV infection," International Journal of Infectious Diseases 96:19-24, 2020 https://doi.org/10.1016/j.ijid.2020.04.027.
Zhou et al., "A pneumonia outbreak associated with a new coronavirus of probable bat origin," Nature 579:270-273, 2020 https://doi.org/10.1038/s41586-020-2012-7.
Hoffman et al., ""SARS-CoV-2 Cell Entry Depends on ACE2 and TMPRSSZ and is Blocked by a Clinically Proven Protease Inhibitor,"" Cell 181(2):271-280 (2020)doi: 10.1016/j.cell.2020.02.052.
Riva et al. "Discovery of SARS-CoV-2 antiviral drugs through large-scale compound repurposing," Nature, 586:113 (24 pages) (2020) https://doi.org/10.1038/541586-020-2577-1.
Soldatov et al. "On the way from SARS-CoV-sensitive mice to murine COVID-19 model," Research Results in Pharmacology, 6(2):1-7 (2020) DOI 10.3897/rrpharmacology.6.53633.
Valenzuela et al., "High-throughput engineering of the mouse genome coupled with high-resolution expression analysis," Nature Biotech. 21(6):652-659 (2003).

* cited by examiner

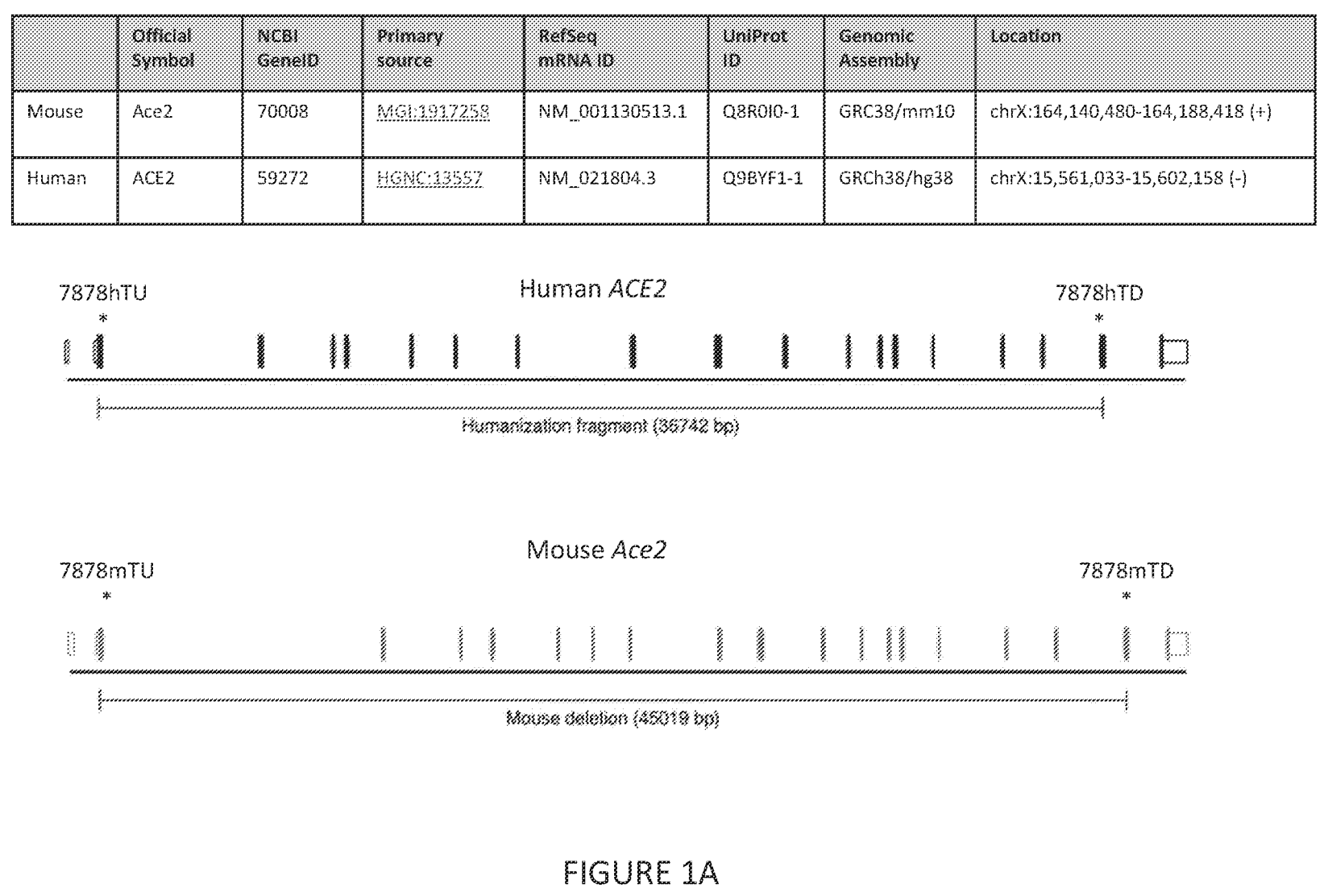

| | Official Symbol | NCBI GeneID | Primary source | RefSeq mRNA ID | UniProt ID | Genomic Assembly | Location |
|---|---|---|---|---|---|---|---|
| Mouse | Ace2 | 70008 | MGI:1917258 | NM_001130513.1 | Q8R0I0-1 | GRC38/mm10 | chrX:164,140,480-164,188,418 (+) |
| Human | ACE2 | 59272 | HGNC:13557 | NM_021804.3 | Q9BYF1-1 | GRCh38/hg38 | chrX:15,561,033-15,602,158 (-) |

FIGURE 1A

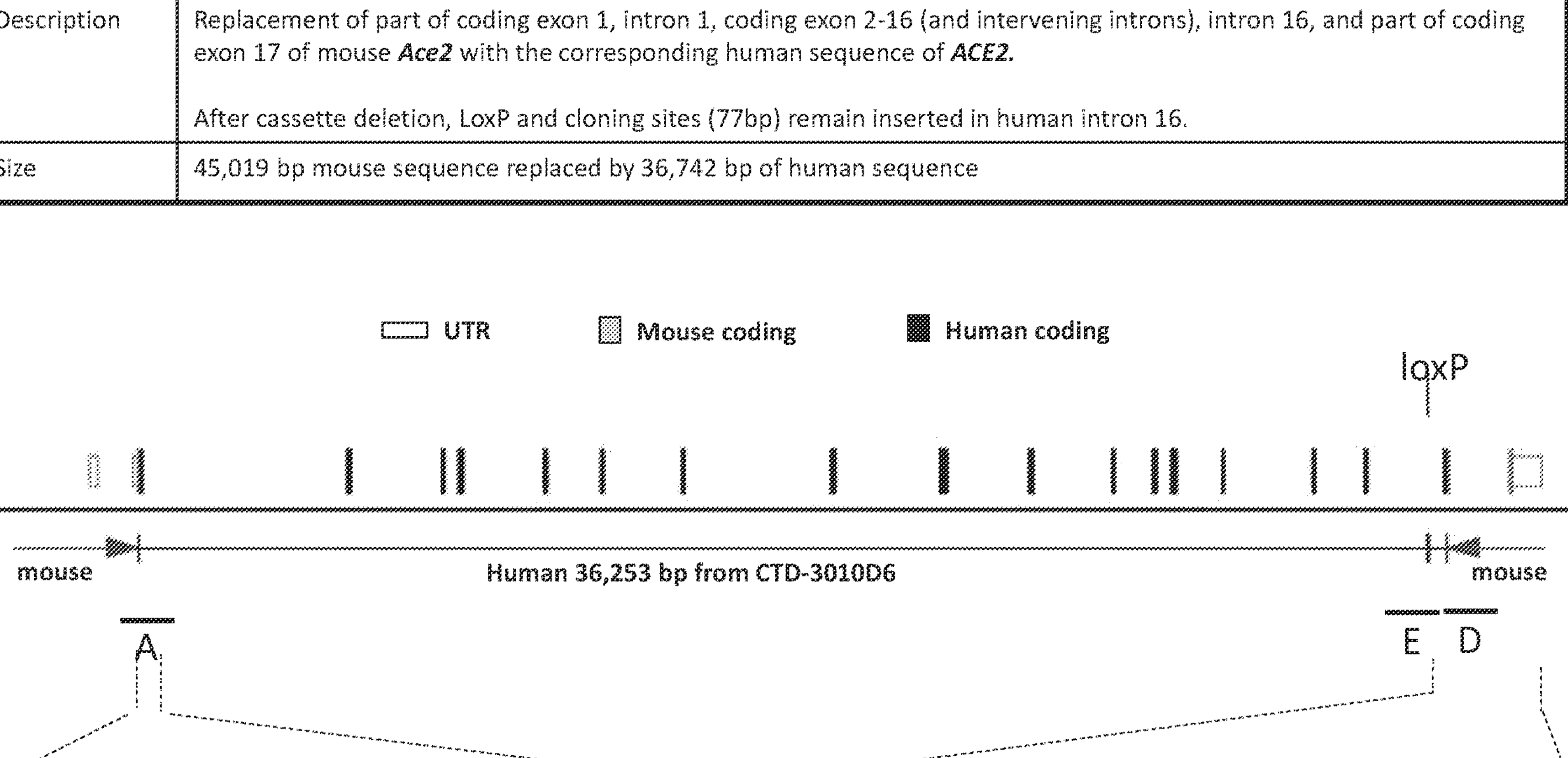

7879 Allele. *ACE2* humanization, cassette deleted, LoxP site remains

| | |
|---|---|
| Description | Replacement of part of coding exon 1, intron 1, coding exon 2-16 (and intervening introns), intron 16, and part of coding exon 17 of mouse ***Ace2*** with the corresponding human sequence of ***ACE2.***<br><br>After cassette deletion, LoxP and cloning sites (77bp) remain inserted in human intron 16. |
| Size | 45,019 bp mouse sequence replaced by 36,742 bp of human sequence |

FIGURE 1C

| | Official Symbol | NCBI GeneID | Primary source | RefSeq mRNA ID | UniProt ID | Genomic Assembly | Location |
|---|---|---|---|---|---|---|---|
| Mouse | Ace2 | 70008 | MGI:1917258 | NM_001130513.1 | Q8R0I0-1 | GRC38/mm10 | chrX:164,140,480-164,183,418 (+) |

90034 *Ace2* CRISPR/Cas9 collapse

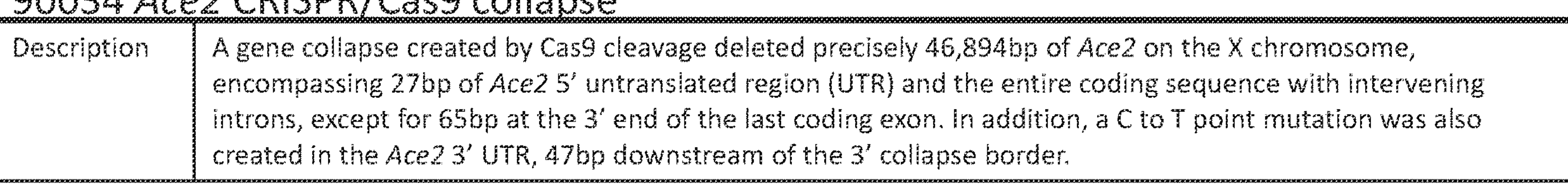

| Description | A gene collapse created by Cas9 cleavage deleted precisely 46,894bp of *Ace2* on the X chromosome, encompassing 27bp of *Ace2* 5' untranslated region (UTR) and the entire coding sequence with intervening introns, except for 65bp at the 3' end of the last coding exon. In addition, a C to T point mutation was also created in the *Ace2* 3' UTR, 47bp downstream of the 3' collapse border. |
|---|---|

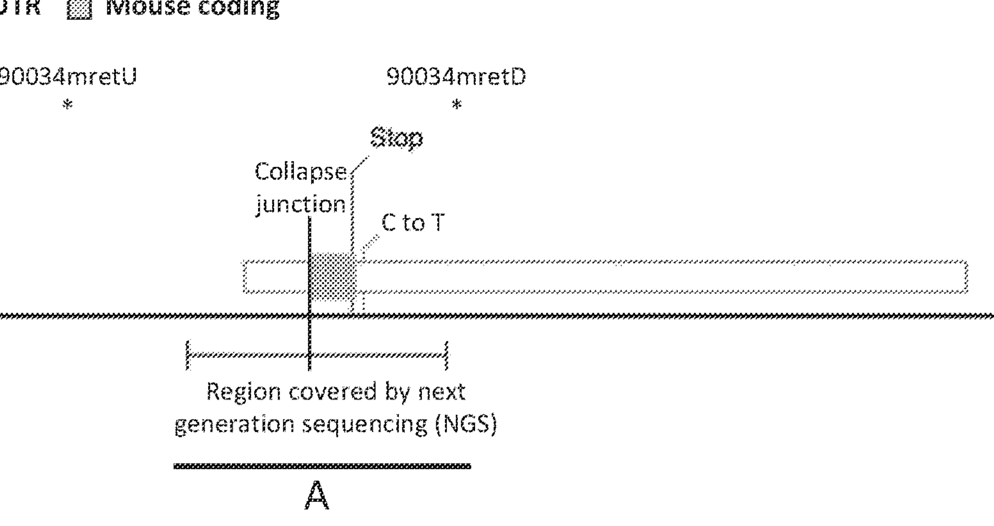

| **A.** 5' mouse (*Ace2* 5' UTR in bold) / *Ace2* exon 19 coding sequence (stop codon in green)-3' UTR in bold, C to T point mutation in red.<br><br>Region sequenced by NGS is underlined. | ATCTGTCCTC TCCAGGATTA ACTTCATATT GGTCCAGCAG CTTGTTTACT GTTCTCTTCT<br>GTTTCTTCTT CTGCTTTTTT TTTCTTCTCT TCTCAG**TGCC CAACCCAAGT TCAAAGGCTG**<br>**ATGAGAGAGA AAAACTCATG AAGAGATTTT ACTCTAGGGA AAGTTGCTCA GTGGATGGGA**<br>**TCTTG** / GAAAA GGAGAAAGCA ATGCAGGATT CCAAAACAGT GATGATGCTC AGACTTCCTT<br>TTAG**CAAAGC ACTTGTTATC TTCCTGTATG TAAATGCTAA CTTCATAGTA CACAAAATAT**<br>**GAGAGTATAC ACATGTCATT AGCTATCAAA ACTATGATCT GTTCAGTAAA CGTTGTCCAA**<br>**AGAGCATCAG ACTTGAGTGG ACATCTTCAC TGACAT** (SEQ ID NO:55) |
|---|---|

FIGURE 2B

Signal peptide

```
mAce2             1 MSSSSWLLLSLVAVTTAQSLTEENAKTFLNNFNQEAEDLSYQSSLASWNYNTNITEENAQ  60
hACE2             1 MSSSSWLLLSLVAVTAAQSTIEEQAKTFLDKFNHEAEDLFYQSSLASWNYNTNITEENVQ  60
7879 final prot   1 MSSSSWLLLSLVAVTTAQSTIEEQAKTFLDKFNHEAEDLFYQSSLASWNYNTNITEENVQ  60
                    ***************.***  **.*****   **.***** ****************** *

mAce2            61 KMSEAAAKWSAFYEEQSKTAQSFSLQEIQTPIIKRQLQALQQSGSSALSADKNKQLNTIL 120
hACE2            61 NMNNAGDKWSAFLKEQSTLAQMYPLQEIQNLTVKLQLQALQQNGSSVLSEDKSKRLNTIL 120
7879 final prot  61 NMNNAGDKWSAFLKEQSTLAQMYPLQEIQNLTVKLQLQALQQNGSSVLSEDKSKRLNTIL 120
                     *  *  *****  ***  **  . *****.   .* ******* *** ** ** *.*****

mAce2           121 NTMSTIYSTGKVCNPKNPQECLLLEPGLDEIMATSTDYNSRLWAWEGWRAEVGKQLRPLY 180
hACE2           121 NTMSTIYSTGKVCNPDNPQECLLLEPGLNEIMANSLDYNERLWAWESWRSEVGKQLRPLY 180
7879 final prot 121 NTMSTIYSTGKVCNPDNPQECLLLEPGLNEIMANSLDYNERLWAWESWRSEVGKQLRPLY 180
                    *************** ************ ****.* *** ****** **.**********

mAce2           181 EEYVVLKNEMARANNYNDYGDYWRGDYEAEGADGYNYNRNQLIEDVERTFAEIKPLYEHL 240
hACE2           181 EEYVVLKNEMARANHYEDYGDYWRGDYEVNGVDGYDYSRGQLIEDVEHTFEEIKPLYEHL 240
7879 final prot 181 EEYVVLKNEMARANHYEDYGDYWRGDYEVNGVDGYDYSRGQLIEDVEHTFEEIKPLYEHL 240
                    **************.* ***********   * *** * *.*******.** *********

mAce2           241 HAYVRRKLMDTYPSYISPTGCLPAHLLGDMWGRFWTNLYPLTVPFAQKPNIDVTDAMMNQ 300
hACE2           241 HAYVRAKLMNAYPSYISPIGCLPAHLLGDMWGRFWTNLYSLTVPFGQKPNIDVTDAMVDQ 300
7879 final prot 241 HAYVRAKLMNAYPSYISPIGCLPAHLLGDMWGRFWTNLYSLTVPFGQKPNIDVTDAMVDQ 300
                    ***** ***  .******* ******************* ***** ***********. *
```

FIGURE 3

```
mAce2           301 GWDAERIFQEAEKFFVSVGLPHMTQGFWANSMLTEPADGRKVVCHPTAWDLGHGDFRIKM 360
hACE2           301 AWDAQRIFKEAEKFFVSVGLPNMTQGFWENSMLTDPGNVQKAVCHPTAWDLGKGDFRILM 360
7879 final prot 301 AWDAQRIFKEAEKFFVSVGLPNMTQGFWENSMLTDPGNVQKAVCHPTAWDLGKGDFRILM 360
                     ***.***.************.****** *****.*   .* **********.***** *

mAce2           361 CTKVTMDNFLTAHHEMGHIQYDMAYARQPFLLRNGANEGFHEAVGEIMSLSAATPKHLKS 420
hACE2           361 CTKVTMDDFLTAHHEMGHIQYDMAYAAQPFLLRNGANEGFHEAVGEIMSLSAATPKHLKS 420
7879 final prot 361 CTKVTMDDFLTAHHEMGHIQYDMAYAAQPFLLRNGANEGFHEAVGEIMSLSAATPKHLKS 420
                    ******* ****************** *********************************

mAce2           421 IGLLPSDFQEDSETEINFLLKQALTIVGTLPFTYMLEKWRWMVFRGEIPKEQWMKKWWEM 480
hACE2           421 IGLLSPDFQEDNETEINFLLKQALTIVGTLPFTYMLEKWRWMVFKGEIPKDQWMKKWWEM 480
7879 final prot 421 IGLLSPDFQEDNETEINFLLKQALTIVGTLPFTYMLEKWRWMVFKGEIPKDQWMKKWWEM 480
                    ****  ***** ********************************.*****.*********

mAce2           481 KREIVGVVEPLPHDETYCDPASLFHVSNDYSFIRYYTRTIYQFQFQEALCQAAKYNGSLH 540
hACE2           481 KREIVGVVEPVPHDETYCDPASLFHVSNDYSFIRYYTRTLYQFQFQEALCQAAKHEGPLH 540
7879 final prot 481 KREIVGVVEPVPHDETYCDPASLFHVSNDYSFIRYYTRTLYQFQFQEALCQAAKHEGPLH 540
                    **********.****************************.**************  * **

mAce2           541 KCDISNSTEAGQKLLKMLSLGNSEPWTKALENVVGARNMDVKPLLNYFQPLFDWLKEQNR 600
hACE2           541 KCDISNSTEAGQKLFNMLRLGKSEPWTLALENVVGAKNMNVRPLLNYFEPLFTWLKDQNK 600
7879 final prot 541 KCDISNSTEAGQKLFNMLRLGKSEPWTLALENVVGAKNMNVRPLLNYFEPLFTWLKDQNK 600
                    **************  ** ** ***** ********.** *.******.*** ***.**.
```

FIGURE 3 - continued

```
mAce2            601 NSFVGWNTEWSPYADQSIKVRISLKSALGANAYEWTNNEMFLFRSSVAYAMRKYFSIIKN 660
hACE2            601 NSFVGWSTDWSPYADQSIKVRISLKSALGDKAYEWNDNEMYLFRSSVAYAMRQYFLKVKN 660
7879 final prot  601 NSFVGWSTDWSPYADQSIKVRISLKSALGDKAYEWNDNEMYLFRSSVAYAMRQYFLKVKN 660
                     ****** *.*******************  ****. ***.***********.**  .**

mAce2            661 QTVPFLEEDVRVSDLKPRVSFYFFVTSPQNVSDVIPRSEVEDAIRMSRGRINDVFGLNDN 720
hACE2            661 QMILFGEEDVRVANLKPRISFNFFVTAPKNVSDIIPRTEVEKAIRMSRSRINDAFRLNDN 720
7879 final prot  661 QMILFGEEDVRVANLKPRISFNFFVTAPKNVSDIIPRTEVEKAIRMSRSRINDAFRLNDN 720
                     *  . * ******. ****.** ****.*.****.***.*** ****** **** * ****

                                                 TM
mAce2            721 SLEFLGIHPTLEPPYQPPVTIWLIIFGVVMALVVVGIIILIVTGIKGRKKKNETKREENP 780
hACE2            721 SLEFLGIQPTLGPPNQPPVSIWLIVFGVVMGVIVVGIVILIFTGIRDRKKKNKARSGENP 780
7879 final prot  721 SLEFLGIQPTLGPPNQPPVSIWLIIFGVVMALVVVGIIILIVTGIKGRKKKNETKREENP 780
                     *******.*** ** ****.****.*****  ..****.*** ***. *****  ..   ***

mAce2            781 YDSMDIGKGESNAGFQNSDDAQTSF   805
hACE2            781 YASIDISKGENNPGFQNTDDVQTSF   805
7879 final prot  781 YDSMDIGKGESNAGFQNSDDAQTSF   805
                     * *.** *** * ****.** ****
```

FIGURE 3- continued

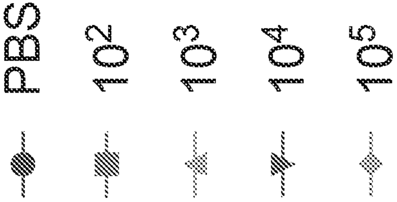
Figure 8
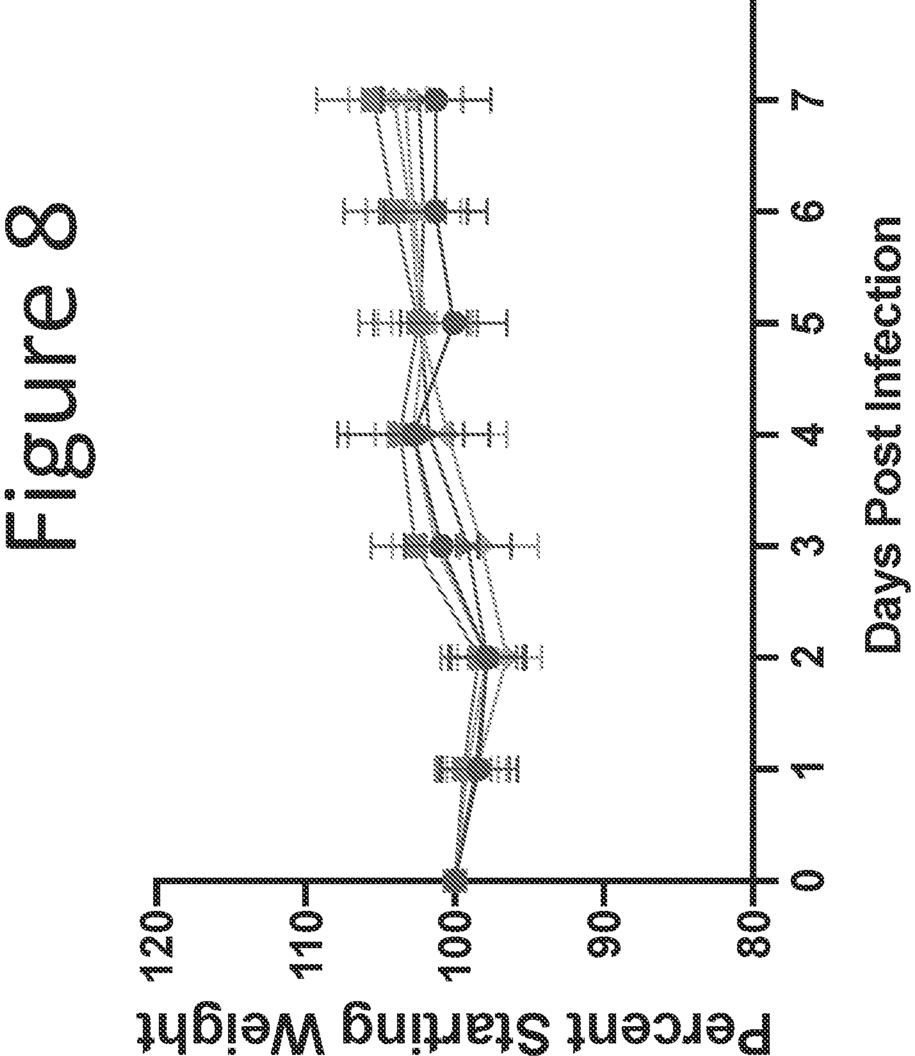

Fold SARS2 Genome
10000
1000
100
10
1
0.1
0.01
50 mg/kg
5 mg/kg
0.5 mg/kg
50 mg/kg
5 mg/kg
0.5 mg/kg
25/25 mg/kg
2.5/2.5 mg/kg
0.25/0.25 mg/kg
0.025/0.025 mg/kg
Placebo
Uninfected Uninfected control
Infected control
Hyperplasia/hypertrophy
Syncytia FIGURE 15
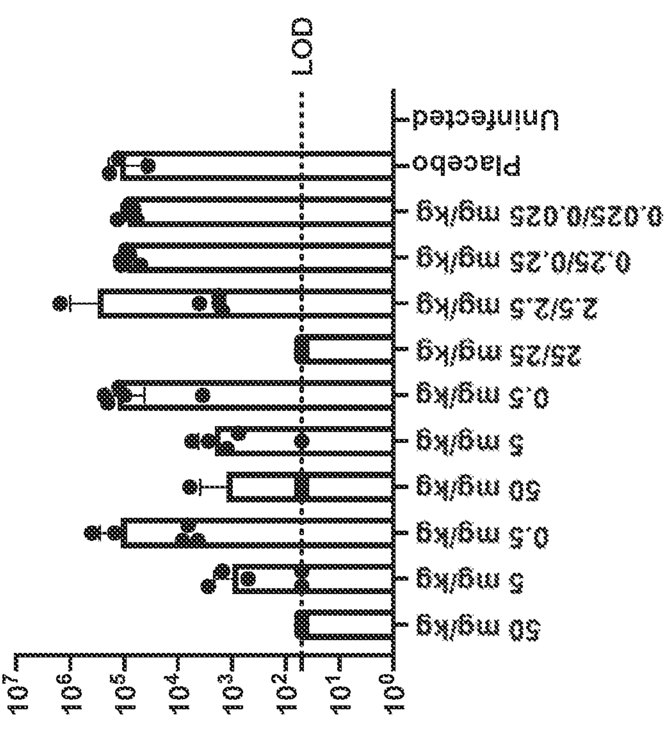
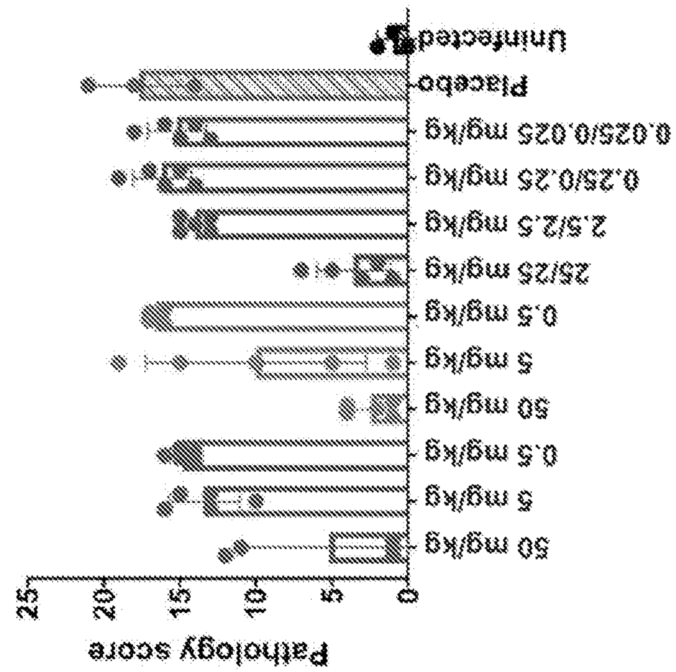

SEQUENCE LISTING

```
<160> NUMBER OF SEQ ID NOS: 67

<210> SEQ ID NO 1
<211> LENGTH: 2418
<212> TYPE: DNA
<213> ORGANISM: Mus musculus
<220> FEATURE:
<221> NAME/KEY: sig_peptide
<222> LOCATION: (1)..(51)
<220> FEATURE:
<221> NAME/KEY: misc_feature
<222> LOCATION: (52)..(2220)
<223> OTHER INFORMATION: Extracellular_domain
<220> FEATURE:
<221> NAME/KEY: misc_feature
<222> LOCATION: (2221)..(2283)
<223> OTHER INFORMATION: Transmembrane Domain
<220> FEATURE:
<221> NAME/KEY: misc_feature
<222> LOCATION: (2284)..(2418)
<223> OTHER INFORMATION: Cytoplasmic Domain

<400> SEQUENCE: 1

atgtccagct cctcctggct ccttctcagc cttgttgctg ttactactgc tcagtccctc     60

accgaggaaa atgccaagac atttttaaac aactttaatc aggaagctga agacctgtct    120

tatcaaagtt cacttgcttc ttggaattat aatactaaca ttactgaaga aaatgcccaa    180

aagatgagtg aggctgcagc caaatggtct gccttttatg aagaacagtc taagactgcc    240

caaagtttct cactacaaga aatccagact ccgatcatca agcgtcaact acaggccctt    300

cagcaaagtg ggtcttcagc actctcagca gacaagaaca aacagttgaa cacaattctg    360

aacaccatga gcaccattta cagtactgga aaagtttgca acccaaagaa cccacaagaa    420

tgcttattac ttgagccagg attggatgaa ataatggcga caagcacaga ctacaactct    480

aggctctggg catgggaggg ctggagggct gaggttggca agcagctgag gccgttgtat    540

gaagagtatg tggtcctgaa aaacgagatg gcaagagcaa acaattataa cgactatggg    600

gattattgga gaggggacta tgaagcagag ggagcagatg gctacaacta taaccgtaac    660

cagttgattg aagatgtaga acgtaccttc gcagagatca agccattgta tgagcatctt    720

catgcctatg tgaggaggaa gttgatggat acctaccctt cctacatcag ccccactgga    780

tgcctccctg cccatttgct tggtgatatg tggggtagat tttggacaaa tctgtaccct    840

ttgactgttc cctttgcaca gaaaccaaac atagatgtta ctgatgcaat gatgaatcag    900

ggctgggatg cagaaaggat atttcaagag gcagagaaat tctttgtttc tgttggcctt    960

cctcatatga ctcaaggatt ctgggcaaac tctatgctga ctgagccagc agatggccgg   1020

aaagttgtct gccaccccac agcttgggat ctgggacacg gagacttcag aatcaagatg   1080

tgtacaaagg tcacaatgga caacttcttg acagcccatc acgagatggg acacatccaa   1140
```

```
tatgacatgg catatgccag gcaacctttc ctgctaagaa acggagccaa tgaagggttc   1200
catgaagctg ttggagaaat catgtcactt tctgcagcta cccccaagca tctgaaatcc   1260
attggtcttc tgccatccga ttttcaagaa gatagcgaaa cagagataaa cttcctactg   1320
aaacaggcat tgacaattgt tggaacacta ccgtttactt acatgttaga gaagtggagg   1380
tggatggtct ttcggggtga aattcccaaa gagcagtgga tgaaaaagtg gtgggagatg   1440
aagcgggaga tcgttggtgt ggtggagcct ctgcctcatg atgaaacata ctgtgaccct   1500
gcatctctgt tccatgtttc taatgattac tcattcattc gatattacac aaggaccatt   1560
taccaattcc agtttcaaga agctctttgt caagcagcta agtataatgg ttctctgcac   1620
aaatgtgaca tctcaaattc cactgaagct gggcagaagt tgctcaagat gctgagtctt   1680
ggaaattcag agccctggac caaagccttg gaaaatgtgg taggagcaag gaatatggat   1740
gtaaaaccac tgctcaatta cttccaaccg ttgtttgact ggctgaaaga gcagaacaga   1800
aattcttttg tggggtggaa cactgaatgg agcccatatg ccgaccaaag cattaaagtg   1860
aggataagcc taaaatcagc tcttggagct aatgcatatg aatggaccaa caacgaaatg   1920
ttcctgttcc gatcatctgt tgcatatgcc atgagaaagt atttttcaat aatcaaaaac   1980
cagacagttc cttttctaga ggaagatgta cgagtgagtg atttgaaacc aagagtctcc   2040
ttctacttct ttgtcacctc accccaaaat gtgtctgatg tcattcctag aagtgaagtt   2100
gaagatgcca tcaggatgtc tcggggccgc atcaatgatg tctttggcct gaatgataac   2160
agcctggagt ttctggggat tcacccaaca cttgagccac cttaccagcc tcctgtcacc   2220
atatggctga ttatttttgg tgttgtgatg gcactggtag tggttggcat catcatcctg   2280
attgtcactg ggatcaaagg tcgaaagaag aaaaatgaaa caaaaagaga agagaaccct   2340
tatgactcga tggacattgg aaaaggagaa agcaatgcag gattccaaaa cagtgatgat   2400
gctcagactt ccttttag                                                  2418
```

<210> SEQ ID NO 2
<211> LENGTH: 805
<212> TYPE: PRT
<213> ORGANISM: Mus musculus
<220> FEATURE:
<221> NAME/KEY: SIGNAL
<222> LOCATION: (1)..(17)
<220> FEATURE:
<221> NAME/KEY: MISC_FEATURE
<222> LOCATION: (18)..(740)
<223> OTHER INFORMATION: Extracellular Domain
<220> FEATURE:
<221> NAME/KEY: MISC_FEATURE
<222> LOCATION: (741)..(761)
<223> OTHER INFORMATION: Transmembrane Domain
<220> FEATURE:
<221> NAME/KEY: MISC_FEATURE
<222> LOCATION: (762)..(805)
<223> OTHER INFORMATION: Cytoplasmic Domain

<400> SEQUENCE: 2

```
Met Ser Ser Ser Ser Trp Leu Leu Leu Ser Leu Val Ala Val Thr Thr
1               5                   10                  15

Ala Gln Ser Leu Thr Glu Glu Asn Ala Lys Thr Phe Leu Asn Asn Phe
            20                  25                  30

Asn Gln Glu Ala Glu Asp Leu Ser Tyr Gln Ser Ser Leu Ala Ser Trp
        35                  40                  45

Asn Tyr Asn Thr Asn Ile Thr Glu Glu Asn Ala Gln Lys Met Ser Glu
    50                  55                  60
```

-continued

```
Ala Ala Ala Lys Trp Ser Ala Phe Tyr Glu Glu Gln Ser Lys Thr Ala
65                  70                  75                  80

Gln Ser Phe Ser Leu Gln Glu Ile Gln Thr Pro Ile Ile Lys Arg Gln
                85                  90                  95

Leu Gln Ala Leu Gln Gln Ser Gly Ser Ser Ala Leu Ser Ala Asp Lys
            100                 105                 110

Asn Lys Gln Leu Asn Thr Ile Leu Asn Thr Met Ser Thr Ile Tyr Ser
        115                 120                 125

Thr Gly Lys Val Cys Asn Pro Lys Asn Pro Gln Glu Cys Leu Leu Leu
    130                 135                 140

Glu Pro Gly Leu Asp Glu Ile Met Ala Thr Ser Thr Asp Tyr Asn Ser
145                 150                 155                 160

Arg Leu Trp Ala Trp Glu Gly Trp Arg Ala Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn Asn Tyr Asn Asp Tyr Gly Asp Tyr Trp Arg Gly Asp Tyr Glu
        195                 200                 205

Ala Glu Gly Ala Asp Gly Tyr Asn Tyr Asn Arg Asn Gln Leu Ile Glu
    210                 215                 220

Asp Val Glu Arg Thr Phe Ala Glu Ile Lys Pro Leu Tyr Glu His Leu
225                 230                 235                 240

His Ala Tyr Val Arg Arg Lys Leu Met Asp Thr Tyr Pro Ser Tyr Ile
                245                 250                 255

Ser Pro Thr Gly Cys Leu Pro Ala His Leu Leu Gly Asp Met Trp Gly
            260                 265                 270

Arg Phe Trp Thr Asn Leu Tyr Pro Leu Thr Val Pro Phe Ala Gln Lys
        275                 280                 285

Pro Asn Ile Asp Val Thr Asp Ala Met Met Asn Gln Gly Trp Asp Ala
    290                 295                 300

Glu Arg Ile Phe Gln Glu Ala Glu Lys Phe Phe Val Ser Val Gly Leu
305                 310                 315                 320

Pro His Met Thr Gln Gly Phe Trp Ala Asn Ser Met Leu Thr Glu Pro
                325                 330                 335

Ala Asp Gly Arg Lys Val Val Cys His Pro Thr Ala Trp Asp Leu Gly
            340                 345                 350

His Gly Asp Phe Arg Ile Lys Met Cys Thr Lys Val Thr Met Asp Asn
        355                 360                 365

Phe Leu Thr Ala His His Glu Met Gly His Ile Gln Tyr Asp Met Ala
    370                 375                 380

Tyr Ala Arg Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Pro Ser Asp Phe Gln Glu Asp Ser
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Arg Gly Glu Ile Pro Lys Glu Gln Trp Met Lys Lys Trp Trp Glu Met
465                 470                 475                 480

Lys Arg Glu Ile Val Gly Val Val Glu Pro Leu Pro His Asp Glu Thr
```

```
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Ile Tyr Gln Phe Gln Phe Gln Glu Ala
        515                 520                 525

Leu Cys Gln Ala Ala Lys Tyr Asn Gly Ser Leu His Lys Cys Asp Ile
    530                 535                 540

Ser Asn Ser Thr Glu Ala Gly Gln Lys Leu Leu Lys Met Leu Ser Leu
545                 550                 555                 560

Gly Asn Ser Glu Pro Trp Thr Lys Ala Leu Glu Asn Val Val Gly Ala
                565                 570                 575

Arg Asn Met Asp Val Lys Pro Leu Leu Asn Tyr Phe Gln Pro Leu Phe
            580                 585                 590

Asp Trp Leu Lys Glu Gln Asn Arg Asn Ser Phe Val Gly Trp Asn Thr
        595                 600                 605

Glu Trp Ser Pro Tyr Ala Asp Gln Ser Ile Lys Val Arg Ile Ser Leu
    610                 615                 620

Lys Ser Ala Leu Gly Ala Asn Ala Tyr Glu Trp Thr Asn Asn Glu Met
625                 630                 635                 640

Phe Leu Phe Arg Ser Ser Val Ala Tyr Ala Met Arg Lys Tyr Phe Ser
                645                 650                 655

Ile Ile Lys Asn Gln Thr Val Pro Phe Leu Glu Glu Asp Val Arg Val
            660                 665                 670

Ser Asp Leu Lys Pro Arg Val Ser Phe Tyr Phe Phe Val Thr Ser Pro
        675                 680                 685

Gln Asn Val Ser Asp Val Ile Pro Arg Ser Glu Val Glu Asp Ala Ile
    690                 695                 700

Arg Met Ser Arg Gly Arg Ile Asn Asp Val Phe Gly Leu Asn Asp Asn
705                 710                 715                 720

Ser Leu Glu Phe Leu Gly Ile His Pro Thr Leu Glu Pro Pro Tyr Gln
                725                 730                 735

Pro Pro Val Thr Ile Trp Leu Ile Ile Phe Gly Val Val Met Ala Leu
            740                 745                 750

Val Val Val Gly Ile Ile Ile Leu Ile Val Thr Gly Ile Lys Gly Arg
        755                 760                 765

Lys Lys Lys Asn Glu Thr Lys Arg Glu Glu Asn Pro Tyr Asp Ser Met
    770                 775                 780

Asp Ile Gly Lys Gly Glu Ser Asn Ala Gly Phe Gln Asn Ser Asp Asp
785                 790                 795                 800

Ala Gln Thr Ser Phe
                805
```

```
<210> SEQ ID NO 3
<211> LENGTH: 2418
<212> TYPE: DNA
<213> ORGANISM: Homo sapiens
<220> FEATURE:
<221> NAME/KEY: sig_peptide
<222> LOCATION: (1)..(51)
<220> FEATURE:
<221> NAME/KEY: misc_feature
<222> LOCATION: (52)..(2220)
<223> OTHER INFORMATION: Extracellular Domain
<220> FEATURE:
<221> NAME/KEY: misc_feature
<222> LOCATION: (2221)..(2283)
<223> OTHER INFORMATION: Transmembrane Domain
<220> FEATURE:
```

<221> NAME/KEY: misc_feature
<222> LOCATION: (2284)..(2418)
<223> OTHER INFORMATION: Cytoplasmic Domain

<400> SEQUENCE: 3

```
atgtcaagct cttcctggct ccttctcagc cttgttgctg taactgctgc tcagtccacc     60
attgaggaac aggccaagac atttttggac aagtttaacc acgaagccga agacctgttc    120
tatcaaagtt cacttgcttc ttggaattat aacaccaata ttactgaaga gaatgtccaa    180
aacatgaata atgctgggga caaatggtct gcctttttaa aggaacagtc cacacttgcc    240
caaatgtatc cactacaaga aattcagaat ctcacagtca agcttcagct gcaggctctt    300
cagcaaaatg ggtcttcagt gctctcagaa gacaagagca aacggttgaa cacaattcta    360
aatacaatga gcaccatcta cagtactgga aaagtttgta acccagataa tccacaagaa    420
tgcttattac ttgaaccagg tttgaatgaa ataatggcaa acagtttaga ctacaatgag    480
aggctctggg cttgggaaag ctggagatct gaggtcggca agcagctgag gccattatat    540
gaagagtatg tggtcttgaa aaatgagatg gcaagagcaa atcattatga ggactatggg    600
gattattgga gaggagacta tgaagtaaat ggggtagatg gctatgacta cagccgcggc    660
cagttgattg aagatgtgga acatacettt gaagagatta aaccattata tgaacatctt    720
catgcctatg tgagggcaaa gttgatgaat gcctatcctt cctatatcag tccaattgga    780
tgcctccctg ctcatttgct tggtgatatg tggggtagat ttggacaaa tctgtactct    840
ttgacagttc cctttggaca gaaaccaaac atagatgtta ctgatgcaat ggtggaccag    900
gcctgggatg cacagagaat attcaaggag gccgagaagt tctttgtatc tgttggtctt    960
cctaatatga ctcaaggatt ctgggaaaat tccatgctaa cggacccagg aaatgttcag   1020
aaagcagtct gccatcccac agcttgggac ctggggaagg gcgacttcag gatccttatg   1080
tgcacaaagg tgacaatgga cgacttcctg acagctcatc atgagatggg gcatatccag   1140
tatgatatgg catatgctgc acaacctttt ctgctaagaa atggagctaa tgaaggattc   1200
catgaagctg ttggggaaat catgtcactt tctgcagcca cacctaagca tttaaaatcc   1260
attggtcttc tgtcacccga ttttcaagaa gacaatgaaa cagaaataaa cttcctgctc   1320
aaacaagcac tcacgattgt tgggactctg ccatttactt acatgttaga gaagtggagg   1380
tggatggtct ttaaagggga aattcccaaa gaccagtgga tgaaaaagtg gtgggagatg   1440
aagcgagaga tagttggggt ggtggaacct gtgccccatg atgaaacata ctgtgacccc   1500
gcatctctgt tccatgtttc taatgattac tcattcattc gatattacac aaggaccctt   1560
taccaattcc agtttcaaga agcactttgt caagcagcta aacatgaagg ccctctgcac   1620
aaatgtgaca tctcaaactc tacagaagct ggacagaaac tgttcaatat gctgaggctt   1680
ggaaaatcag aaccctggac cctagcattg gaaaatgttg taggagcaaa gaacatgaat   1740
gtaaggccac tgctcaacta ctttgagccc ttatttacct ggctgaaaga ccagaacaag   1800
aattcttttg tgggatggag taccgactgg agtccatatg cagaccaaag catcaaagtg   1860
aggataagcc taaaatcagc tcttggagat aaagcatatg aatggaacga caatgaaatg   1920
tacctgttcc gatcatctgt tgcatatgct atgaggcagt actttttaaa agtaaaaaat   1980
cagatgattc tttttgggga ggaggatgtg cgagtggcta atttgaaacc aagaatctcc   2040
tttaatttct ttgtcactgc acctaaaaat gtgtctgata tcattcctag aactgaagtt   2100
gaaaaggcca tcaggatgtc ccggagccgt atcaatgatg ctttccgtct gaatgacaac   2160
agcctagagt ttctggggat acagccaaca cttggacctc ctaaccagcc ccctgtttcc   2220
```

```
atatggctga ttgtttttgg agttgtgatg ggagtgatag tggttggcat tgtcatcctg   2280

atcttcactg ggatcagaga tcggaagaag aaaaataaag caagaagtgg agaaaatcct   2340

tatgcctcca tcgatattag caaaggagaa aataatccag gattccaaaa cactgatgat   2400

gttcagacct cctttag                                                  2418


<210> SEQ ID NO 4
<211> LENGTH: 805
<212> TYPE: PRT
<213> ORGANISM: Homo sapiens
<220> FEATURE:
<221> NAME/KEY: SIGNAL
<222> LOCATION: (1)..(17)
<220> FEATURE:
<221> NAME/KEY: MISC_FEATURE
<222> LOCATION: (18)..(740)
<223> OTHER INFORMATION: Extracellular Domain
<220> FEATURE:
<221> NAME/KEY: MISC_FEATURE
<222> LOCATION: (741)..(761)
<223> OTHER INFORMATION: Transmembrane Domain
<220> FEATURE:
<221> NAME/KEY: MISC_FEATURE
<222> LOCATION: (762)..(805)
<223> OTHER INFORMATION: Cytoplasmic Domain

<400> SEQUENCE: 4

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255
```

```
Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525

Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670
```

```
Ala Asn Leu Lys Pro Arg Ile Ser Phe Asn Phe Phe Val Thr Ala Pro
        675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
            740                 745                 750

Ile Val Val Gly Ile Val Ile Leu Ile Phe Thr Gly Ile Arg Asp Arg
        755                 760                 765

Lys Lys Lys Asn Lys Ala Arg Ser Gly Glu Asn Pro Tyr Ala Ser Ile
    770                 775                 780

Asp Ile Ser Lys Gly Glu Asn Asn Pro Gly Phe Gln Asn Thr Asp Asp
785                 790                 795                 800

Val Gln Thr Ser Phe
                805
```

<210> SEQ ID NO 5
<211> LENGTH: 45619
<212> TYPE: DNA
<213> ORGANISM: Artificial Sequence
<220> FEATURE:
<223> OTHER INFORMATION: 7878 allele
<220> FEATURE:
<221> NAME/KEY: misc_feature
<222> LOCATION: (1)..(1377)
<223> OTHER INFORMATION: 5' Mouse Sequence
<220> FEATURE:
<221> NAME/KEY: misc_feature
<222> LOCATION: (1378)..(37630)
<223> OTHER INFORMATION: Human 36253 bp from CTD-3010D6
<220> FEATURE:
<221> NAME/KEY: misc_feature
<222> LOCATION: (37631)..(37636)
<223> OTHER INFORMATION: Xho1 restriction site
<220> FEATURE:
<221> NAME/KEY: misc_feature
<222> LOCATION: (37637)..(37670)
<223> OTHER INFORMATION: LoxP sequence
<220> FEATURE:
<221> NAME/KEY: misc_feature
<222> LOCATION: (37671)..(38357)
<223> OTHER INFORMATION: Prm
<220> FEATURE:
<221> NAME/KEY: misc_feature
<222> LOCATION: (38358)..(39498)
<223> OTHER INFORMATION: Crei
<220> FEATURE:
<221> NAME/KEY: misc_feature
<222> LOCATION: (39511)..(39740)
<223> OTHER INFORMATION: SV40 p(A)
<220> FEATURE:
<221> NAME/KEY: misc_feature
<222> LOCATION: (39795)..(41007)
<223> OTHER INFORMATION: hUbi
<220> FEATURE:
<221> NAME/KEY: misc_feature
<222> LOCATION: (41008)..(41074)
<223> OTHER INFORMATION: EM7
<220> FEATURE:
<221> NAME/KEY: misc_feature
<222> LOCATION: (41075)..(41878)
<223> OTHER INFORMATION: Neo
<220> FEATURE:
<221> NAME/KEY: misc_feature
<222> LOCATION: (41879)..(42363)
<223> OTHER INFORMATION: PGK p(A)
<220> FEATURE:

<221> NAME/KEY: misc_feature
<222> LOCATION: (42369)..(42402)
<223> OTHER INFORMATION: LoxP site
<220> FEATURE:
<221> NAME/KEY: misc_feature
<222> LOCATION: (42409)..(42434)
<223> OTHER INFORMATION: IceuI
<220> FEATURE:
<221> NAME/KEY: misc_feature
<222> LOCATION: (42435)..(42440)
<223> OTHER INFORMATION: NheI
<220> FEATURE:
<221> NAME/KEY: misc_feature
<222> LOCATION: (42441)..(42929)
<223> OTHER INFORMATION: Human equence 3'
<220> FEATURE:
<221> NAME/KEY: misc_feature
<222> LOCATION: (42930)..(45610)
<223> OTHER INFORMATION: Mouse sequence 3'

<400> SEQUENCE: 5
aggcccatga gccctgccat ttaaagtggc tcctctctta cactctggga atgaggacac 60
ggagccagct gctgaacttc accaggataa ccattaaaat tgctttggag ttcatatttc 120
cacgatccca tgcctatgga tgccaaggac ttgtcatgga tgcgctttgg atttcataat 180
gcagagtcat tattacttcc ttgagttctc agctgagttg taagcaggta agtgaaaggg 240
aaagaggcac ctgataaagt cagctgtagg actagagttt agcatgtctc ctgagaaata 300
gaaaatgact gcttgaaact ttaccaaagc cacacaggaa gcatcaaact ccctatggag 360
tggagaagag tcttataatt ttttaaatgg gcagagaaat gaatttattt ttaattttta 420
gagacagggt ttctttgtat agctctagct gtctttgatt ggtagacaaa gctgtcctca 480
aactcagaga tcttccttcc tttgtctcct gagtgctggg attaaaggca tggaccacca 540
ctgccctgcc ccattctctc cattaatttt aagtgaatgc ttgcaaaagc tcacttcttt 600
ggtgaacagc ttcctttaca aataagtacc tttgccttcg tttttatagg attcttaaaa 660
agaaaaaaaa gattcagcca ggtggttgtg gtgcacacct ttaatcccag cagtcaggag 720
gcagaggaaa gcagatctct tgagtttgag gctagcctag tctacagagg gagttccagg 780
acagccaagg ctacagagag gaactgtcta aaaacaccaa gaaagagaga aaggagagag 840
ggagaggatg gatagcttat tgatagaatt gtcagaaaag gctataagtt ccaatatgtg 900
tcccatgatt tctaagtcta gccctttctg ttatagtaaa atcatagtac accctcctcc 960
tccagtgtat ctttaacagc ttttaaggaa catattaact aaatgtccag gttttgattt 1020
ggccataaaa tgttagcaaa gctaaggttt tctaggatta atgaataaca tgtctttatt 1080
tagtttactt aaaaaaatca ttctaaaata tctgtttaca tatctgtcct ctccaggatt 1140
aacttcatat tggtccagca gcttgtttac tgttctcttc tgtttcttct tctgcttttt 1200
ttttcttctc ttctcagtgc ccaacccaag ttcaaaggct gatgagagag aaaaactcat 1260
gaagagattt tactctaggg aaagttgctc agtggatggg atcttggcgc acggggaaag 1320
atgtccagct cctcctggct ccttctcagc cttgttgctg ttactactgc tcagtccacc 1380
attgaggaac aggccaagac atttttggac aagtttaacc acgaagccga agacctgttc 1440
tatcaaagtt cacttgcttc ttggaattat aacaccaata ttactgaaga gaatgtccaa 1500
aacatggtga gttctcatgg ctctattggg ctatttgttg cctcttaaag attagattac 1560
tgcccgtgaa actgaaaagg gaaatcaaaa aaaatgctct gagttgtgag attggatgtt 1620
tgcctccata tccctgattt tggcgtcgac gataactaaa cttaattgac cctggggttc 1680
attcagaaaa ttgttacaaa ataattcact ggtctcaatc cagatgcttg gaaacaagag 1740

```
aatattcttt ataaagttac caccataatt ctcatcacag tcaggatttc aaagcatttc   1800
atggaaatgc cataagttat tgagttaata atttccttta gcctacaata tcaataggaa   1860
tatctaaaga ttctctacaa atgatatatt aactgaaaaa tgcaactgga ggcttagtga   1920
aagaactagt aattaagcta atcagggctt gggtgaggct ggacttggga attcctttcc   1980
tctttgtcac agacctccaa gggactccaa aaggtcacag aatccaggca gagccctcca   2040
aaacaaaaac aaaaacaaac aacaaaaaaa ctatgattaa accagttctg acaaatatca   2100
gaatgctctg ggaaagccag atgctttaac aagtgcaagg atttaggaat ttcttctctc   2160
acagatccca aaacagtatc cttaagtggt gatccttatg tcaagctgtg agaatatacc   2220
tcaaaataat agaaggcatc caaacttgat cagtatagtg tcataaagct gctgatgtag   2280
aagtgtggag aggtccatca gatagagata tggaaaaaaa agcttggtta aaacaggttt   2340
ccaaagttct ctccctttct ctgccattgt ggtatgtgtg gttgaccatt tctcatcatg   2400
ttttcttaca agactttcag gatcaagcaa ttcctcgcca aaaaacaaaa tcaaggacac   2460
gttgtagcta tttcttggtg agttaccaga agctgtgaag agagagcatg aggcccatac   2520
tttttttttt ttttgaaggg tctcgctctg ttgcccaggc tggaatggag tggcatgatc   2580
atgattcatt gcagcttgac ctcctgggct caaatgattc tctcgcatca tttaacattt   2640
tttttgtag agatgagatc tcactttgtc tcccaggctg gtcttgaact cctgggctca   2700
agtgatcctc ttgcctcagg ctcccaaagt gctgggatga caggcatgag ccactgcacc   2760
tagcctacca cacttactct ttgcgtggtc tctagagctt cttcagcccc cctgctgcca   2820
gggtccctag ggtcttgggc atgccccatt tctgaaccta ttcctgtctc cagggataga   2880
gtcacagtga actcagacca gggtaattct aaactgctat tctgtatata cccaaggaaa   2940
tttcatccct gtctctaatg agtctgtccc atgcccctta atacacatga acacctacac   3000
acaggtacaa gtcggggaag atcactgtgc agcacataaa ataaaattca ggggcgagca   3060
cttttttcc catgagataa agttaggaaa aaataaaaat gttcatacag attaaaaatt   3120
ttaaatgtta aaatattaaa cccccaatct aaaataaaga aaaaataatt tcttaaatcc   3180
taagcttgag ttatggaatt cacattctta taatttacat tacctatttt gttaaatgga   3240
agactttttt ttttaatatg caagtacctg ggcatattta gaaagtaacc aaggcagctt   3300
ttgtctttga acctgatgcg gttttgacag ctctatctgg aaattgagcc agcatatggg   3360
agccaagggt gaaagttttc ctgggagatt tgggctccaa ggtactggat agatgctaaa   3420
gattccattc agtttttcat tttctgtctt catggaactc tcacacctac aggggaagaa   3480
atggtttaga ggttactaaa agtatatagc ctggtttagg tgatagtgag ctatagaaaa   3540
agagaaaata agttgtcagt actttaaatc tcaaacaact tcttacaaaa ggattttaat   3600
agtttaaata caattatcac aagttgggta aagacaacca gacctatggc ctgataaatc   3660
atgtatttaa tttatgcata tagttagggc caaaaagagc agagtatctt tttgaatgtt   3720
ttaaaatata atctaggatt ttatgcctac agtccttgaa attacaaagg atctctctca   3780
agttgggaat atgctatcca ttgcagttac ggatgggatt tagagactgt tttaatttct   3840
tgtgattatc tcaaacaacg tgttccttac tcccaaaact cccttgtatg gctacagaaa   3900
ctgttgcagt tttagttgct tctcccctgc ctttgcccag aggtagtgtg gaatgccacc   3960
aattttatct gtaatggttc ctttcaagcc tggggctatg taagctgcta tatatgcttc   4020
attccattca tcattcagtc taaatatagc tatcaaccac taaattatct gataggtatg   4080
```

-continued

```
catgaactga ctgattcttt gcataactac taagctatct gttttattta ggcttgggag   4140
ccctagggta aggatacgga ataaattgta aatgatatta aaagaatagc ttggcaagga   4200
ataatacctc ctcaggggcc aaaatgcaag gcaacacaaa gtgatttttt tggtgatata   4260
attataacac atgtagtatg gtagtgataa ctaaaataaa attggatagc ctcaaaattc   4320
ctacatgtag tatgataaac aatgttctaa gactgaggcc tttgggaggt agtgagttat   4380
ttcctataga tagagagtaa aattattcct ataatttggt atgaaagttt taccagaaat   4440
tttgcttcac agtaaatcat ctggattggg tgaagccagg tagggattga gaagtgagtc   4500
aggtgggttg catagatgag tttgtgctgc agaccaaact cctcttccca tagctcactt   4560
cttcccactc ctgcatgtta gagagaagac tagaatgtgt caaatacaac ctataggata   4620
atagttcaga gcattagctt cggaagtaaa cactaggttg atgccctggt tcttctaatt   4680
tctagctgtg tgacctaggg aaagttacct gctgtgtgcc tcatttccct tatttgtaaa   4740
gttgagacaa taacaactcc ctcacaaggt tgttgtgaag attaatgaaa aagcagtttc   4800
tgagaggttg tgagtgttca gtaaagaaag aaattgcttt cctttttttt tttttttgag   4860
acagattctc attctgtcat tcaggctgga gtgcagtggc gcgatcatgg ctcactgcgc   4920
ctcgacttcc ccaagctcag gcaatcttcc cacctcagcc tcctgagtag ctgggactac   4980
aggtgcgagc caccacacct ggctagtttt tgtattattt gcagagatgg ggtctcgcct   5040
tgttgcccag gcttgtctca aacttctggg ctcaagcgat cttcccacct caacctccca   5100
aagtgctggg attacaggca tgaaccacta cacacagcct attttccatt ttcactgcca   5160
ttattttctc tgtctcttgt gtggctcatt actgccactt ctgtgcacca tttccatcat   5220
gtcacatgcg tagtcaaaac cctcagtgac tgcctaattc tcagagggta aaagtgaaat   5280
tccttggcct ggaaagtgca atcatgcctg aagttctacc tgtgggagct gtactagtta   5340
tctattgtgt aaaaagttac cacaagctta gcagattaaa acaacacata tttaatatcc   5400
cacagtatct gtgggctagg agtccaggca cagttcagct ggatcttctg cttctaagtc   5460
tcatatggtt gcattcaagg tgctggctag agctatggtc tcttctgagg cttgactggg   5520
gatggatata cttccaagcc aatgcaatta ctcagaggcc gtctttaatt atttgccatg   5580
tggccttttc catagggtag ctcacaacgt ggcatcttgc tgcaacaagt cagcaaagga   5640
gagagtcttc tatcaagatt aaagttaaaa tcttatgtaa cgtaaacatg acatcctgtc   5700
acctgtgttg tatgctattg gttgaaagta aatcacgggt ctgctcatac ttatggggag   5760
gggatcacac aagggtgtga ccaccaaagg cagagatcat gggagcattc ttagagtctg   5820
tctgccacag ggccaggatc aaatgctggt ggctgattgc cagctccact gtttatttct   5880
ctcagccgct ttctgtatgt acaaaaaagg agagagagtg attttctacc tcatagtgtt   5940
gttaagaaaa tcaaatgagg taaattattt tgcaaagtat tctctactca tctgactcct   6000
acctactttc aggtctgtct taagttgcaa cttctgcatg agggcttggc caagtatggt   6060
cacctgcatg aatttcctct ttcttgtaac agaaactgct tggcccactc ataatttata   6120
cattattata tactcttatg tttcattaat gaaacattta taatgcatat cttatctgtc   6180
tgataaaatg gaaagcaatc taaggacaat gacttttccc ctatacataa caaaatataa   6240
aataaatcat aacataataa ataataaata aataataaaa taactaacat ttgttgaatg   6300
attaggatgt gttaggcact cttgtaagca tttcattttt ttgttacttc ttcaaatcct   6360
tacaacagtc cttggaggta agtcctatta ttactttcat tttgcagata agacaactgt   6420
ggctcagaga ggctaaggta cttgagtcca ggagcagaat tcttactttc ctcaaacgtt   6480
```

```
atctcttttg tgtggtctag ggcagtacaa tataccaagt agttgctcat tttggtcttt   6540
ggtaaatgga aatgaatttg taagttgaga aaagactaca ctacagtagt ttggagaagt   6600
ccactttcca actgatgttc aagattcagg aggggggaa atgtgtcctg gcatcatcac   6660
ttgcttgatg atttcttttg ctggtagaaa atcaccatgg ctaccaatgg ccattttctg   6720
ggaagccttt tttgggaatc ctaacttaag atcaaaatcc ctgggctaag tcacggcagc   6780
taggaggtta ctgtgaaccg gttctcattt cttatggttt ccattgttat taggggggctg   6840
tattctcatt aagtccactc tgagctctac tggattctct ttttagagca ctcgtctttg   6900
aattcttggc caactcatct atgtcacagc actaaggcta taaattccag ggccccacaa   6960
tgtggattat ctgtgagaat tcatttccag ttctggggac aagacccttg ggaaaaccag   7020
gcaataggcc agagagagac agagagagag agagtggtca aaagtggcct ggtcactctt   7080
aacctaaacc ttgaccttca gcggagtaga ggactaaatc actcaggaaa tattaaatgt   7140
ttcaccagat attatttgga ctatatcttc tgttctatct cttcaagcaa tgccattcca   7200
acttcaattt tcttttctgt catttcagaa taatgctggg gacaaatggt ctgccttttt   7260
aaaggaacag tccacacttg cccaaatgta tccactacaa gaaattcaga atctcacagt   7320
caagcttcag ctgcaggctc ttcagcaaaa tgggtcttca gtgctctcag aagacaagag   7380
caaacgggta cgtttgtgaa cattttagca ttgatcccaa gagttgaaat atttgggaaa   7440
tattaaacat taatatcacc cacagcagct gcctttattt gaaaaaatag taatgctgat   7500
gttagaaaaa tctctctcta tgcctaggta aggtgtccat ataatttatt attcaaactg   7560
gaatctttga gagtgaaaga cactggtaat tattatattc aaacacagag ttaaactgag   7620
attgtccctg gcactgtggt gtgtatggac accccctagt gttaggtcac cttcctgaag   7680
gatcaggcag cctgaagaat acagttagtt tatgtcagtg gttctcaact gggggtgatt   7740
tagccctccg ggatatttg acaatgtctg gagacgtttt tggttgccac aaatggggat   7800
actgttgaca tctagtgggt agggatgctg cagaacattt cacaatgcat gggatggccc   7860
ccaacaacaa agaatgatct tgtccacaat gtcaacagca aacttttttt tctgtaaagg   7920
aacagatgac agtaaatatt ttaggttttg tgtatttagg tattgtctgt gttgcaacta   7980
gtcaactgtg ctgttgtatc aggaaatcag ctgtagctaa tatataaatg aacaagtatg   8040
gctgtgttca aataaaactt tacaaaaaca ggcagcagac aggatttggt ctgcagaaca   8100
cagtttgcag acctctgata tagcctattg aaatattttt aacctaaaat atttagctat   8160
ttaaaaagaa agtcttcttt ctcagttgct tgtcctctgg aactttgtat gttctaatct   8220
gtgaatataa aaataaaaat gcatcaaaaa ggcaaagata aaaccatgtg aaatgtatct   8280
ttctacaagt taacatttat ttttctgcat tctttgggtc caattatcca actaattatc   8340
aatgcacttt actttatcca ttctatgttt ctccattttt tcccccaaca aggacactat   8400
aagaaacctt gcccattcgc atatagacaa tctggtctag cctaggtgga acctagaaat   8460
tctatttttt aaaaaatccc cagataattc taatgtgtag ccaggactga aaaccactga   8520
aatgcatgta agagcttaaa gtgtttggga agaggaggga ctcaaggttg cttagatttg   8580
atggagagga agccgtggag attgaagaag agctggagag agaccatgag ggttttgtg   8640
ccatggtaag gaatttaggt ttgttccttt ggactatggg atcgtgtgga agttttaaac   8700
ataggatcta tttcatgttt taggatgact ctcaaggcag aaccaaaggg aaataggaga   8760
aggagaaaca gatcctttaa tccagtgctt cttaaatcaa tctgagggag agaaccattt   8820
```

```
ccttccttcc ttccttcctt tcttctcttc ttccttccct ccttctctcc tccctcccgt   8880
ctttcctttc tccctccttt attcctttat ttccaataca ttgcagatca atacttgctt   8940
aagttcattg attacatgct tagatgtcat ggaaatatca aattgttctc caaagtttat   9000
aaacttttat tctcttaatt cctgtactta tcacagaatg gaaacaaact gtcacttgca   9060
ctggtccacg gattacacct ggagtagcac tgcttcacta tatcaccttc actttatctg   9120
cagggtaaag tttaaaaact ttggtatggc atagacggtc cctcgtgatc tggcccctgc   9180
ttgtctctcc attctcatgt ctttcatttc ccctaatgaa caccattgct ccagtttcat   9240
tcaacatctc actgtcccct gagaatgcct tgtcttttcc aacctccttc catcttttag   9300
actcttccct ctacctccct tctctacatg accagtgcct acttcttctc caagacacag   9360
ctcttatctt cccttctctt tggacccatt cttgaatctc ctggttatta gttattaatt   9420
tctccctgct cctatactac cgcatcactt tttggtgaca gttatagcac ttgtcattct   9480
gttatgtatt aatagttatt gatttcatgg ctgcctcact gtcctatgac tttatggtct   9540
ttgacttgtt cacttcagaa ttgtcagagt gtaggacata ttccaggttc aataaatgct   9600
gaatgaaaca aaaaatgcac ctctctgtgt atgtgtggat aagaaaactt ctttgggttt   9660
tggtagatct ggttatttca attactccat atatatttat tatgtgctta tagtactttg   9720
tgctagtcga cagtggggaa acttaactgg gctattcctt ctccacatac agaaagatac   9780
atggcaaaga agtaaattgc tgtattttga gtaatcaaaa aatcatgtgg tcaaaaggat   9840
atctttatat tagcattctc ttcagcaaaa tttccattgt taacattgtt tattatcttt   9900
aatttgcagt tgaacacaat tctaaataca atgagcacca tctacagtac tggaaaagtt   9960
tgtaacccag ataatccaca agaatgctta ttacttgaac caggtaggct actaattttt  10020
agtagtgatt atgaaattta cttttctctc agattttaaa aatgattgca gatatgtgtg  10080
tttcaacaca tagatgctct tttaactttt agtaaaactt tcttgtaaat tgtatcacat  10140
ttacttaatt tgatcaagtc agtaagtaag tcatttcagt ggtttatttt ctctgcagac  10200
atattttgga actataaggg caaggacatg aatgaatcat gagattttat ttaaccactt  10260
tatgacctga tgtctgccaa ccttactttt aattctttaa agttcatgta gttctttaca  10320
aataaaattt ttacaaaggc atcttttctt gtctttgtgt gctttgggat aacaggtttg  10380
aatgaaataa tggcaaacag tttagactac aatgagaggc tctgggcttg ggaaagctgg  10440
agatctgagg tcggcaagca gctgaggcca ttatatgaag agtatgtggt cttgaaaaat  10500
gagatggcaa gagcaaatcg taagtttgct gatctgtaga ggtcctgaag ctctctgtgt  10560
ggccacgggg ctatttcttc tgcattacca agcctgccct ttgatatcag ggatacccct  10620
caattaacaa tcatgtcctc aacaattcag attacctgtt ttcaaaagaa attactgggg  10680
aaaaagaaaa ggtgcactgg cattctacaa ttcaagaagc tcaagaatga gactcaacta  10740
caaggcctaa agtaaattat ccaggaatta tgaattataa gtaatctagg aagatctcag  10800
gcccctaaaa gttcccgagg gagtctgggg attaaggggg ggaatcccat ttctcaggat  10860
gaaagacaga gtcactgcct tttgtctaaa gcccccacag ttcactttca aaggtcattt  10920
gtgtgtctac cttagggtga taccccagaa agaaaaaaata tcagattagt ttaggctgga  10980
aatgtattat tttctgcagt tgtaattata tctcagatta tgtggtcata aaaaatctta  11040
acataggaag gaatttccat atctcttaac ttattctctt ccctgaatag tgagctgaag  11100
tcatggaatc atgattcaca ttttgctttg atgatttact gcccactgag gttgagtaag  11160
gaagaatttt tttcccgcat ttgttgtttt aacatttctt tcactgccac ttaaattcag  11220
```

```
tattcttaag ccttaggcaa gctggagaca atagcttatc accattttta aaacaatatc  11280
ctgcatgtcc tttcatccaa atatttattt ctctcctcat cttcctgatc attaattgcc  11340
aatgtgaatg taaaaataaa aattattaaa ttatgtttac aaactttatt agctaatatc  11400
ctaacacaag cttgtgtttt ctgatggtga gatactaaag gaagcacata gaaacatgct  11460
attgatacat ataatttgca aacaaacaca ggttcactgt ggcaaagtct aagatgagtt  11520
gggtctgatc taaaaataaa aggccatgaa caaaagaaga atttaaaaac ttagagatcc  11580
agtcacatat tttaaagcta aagatacaaa ctgatgtatc aagagagtac acacccaggg  11640
ttaagagact aggaatgtgc ttctttcgct taccagctgt gtgatcttgg acaagtgatt  11700
taaccactct aagcacaggt tgttggtggg aatataaact ggtgaagctg ttatggaaaa  11760
atagtatgag gattcctaaa taaattaaaa atagaattac cgtatgatcc agcaatccct  11820
cttctgggta tatacctaaa ttagatgaaa ttaccccttc ataaagatat ctacactgcc  11880
atgttcactg cagcattatt cgcaatagcc aagataggga aacaacctaa gtgtttgtca  11940
agggatgaat gaataaagaa accgtggtag gtatatggaa tgggatatta ttcagcctta  12000
aaaaagagga gatcctgtca tttgcctcaa catggataga cctggaggac attatgctaa  12060
gtgaaataat ccagacataa aaagaaaaat atggcatcat ctcactcaaa agtggattct  12120
acaaaaaaat caaatataca gagatagagt aatagtgatt accaggggtg aggtggagcg  12180
gggtgggata tggggagaag tgggttaaag gatacaaagt agcagatatg caggatgaac  12240
aagtctaaag atctaatgta caacataagg actgtagtta gtaataatgt tttgtattca  12300
ggatttttgc aaaatgagta gattttagct gctcttccat ggggggggata atgcttaact  12360
atgtgagatg atggatatgt taatttgttt tactatagta accattttat tatataagta  12420
tctcataaca tcatgttgta caccttaaat atacacaata aaatttattt aaaaataaac  12480
ataggctgtt actctgcaca gtgggagtta taataatgac aatcttgtat ggttcttgtg  12540
cttattaaat aaaataatac atttaaactc ctggcacaga gcaagtgctt aaacagagat  12600
tacttaatgt tattattcat ttgcatccct ttgagttgat gtttatcaca ataaaaatgt  12660
gataagcctt taaatttctt ttaacctccc agcaaggcta atctgtgtat tttgtgcttt  12720
ctctctttct ttcccttatg ttcttccctt tctctttaaa aaaaaaaaca aacagattat  12780
gaggactatg gggattattg gagaggagac tatgaagtaa atggggtaga tggctatgac  12840
tacagccgcg gccagttgat tgaagatgtg gaacatacct ttgaagaggt aagcaaggaa  12900
ctgtacacac aaacagttgt ggggcagtgt atgggaaaga gggacagtga ctaaaggcat  12960
tctggctcat tcttaacaca ttggtcagcc attcccaggc ctcataaagt tatggaatat  13020
tagagtttga aagattttag agaataatag gacagcccct acagatgatc agaattgcgc  13080
tgctttcctc cttctttcag tcactgacca ttaattacca atagaaagac tataagaatg  13140
aaatattata agaacaaatg gtcctttaga ttataagtag gaatgatctt cttgagctac  13200
ctggggctgg cactgtcttc ctgtgttagc agagctatgg actttgcttt cttcctcagg  13260
acaattgata ctattacttt gagtaagcta gtcttcatag ggaagagaga gttttgtgaa  13320
cagaaatgtc ccatggatgt tttccttca ttttggcccc atgcctcccc tttacgtgaa  13380
ccttcaaact tctgatgtga gttaccttgt cacagccata gtttggcaga gctatcaaaa  13440
atggaagtaa gacaaacaac tccccaaaaa ggaaatggga agaagacttg aataagtaca  13500
tcatcaaaga aattacacaa atggcaaata ggcaaataaa aagttattag ggaaatgcaa  13560
```

```
attaaagcta tgatgaaaat ccactccaca cccaccagga tagctatgat taaaaagatg  13620
gacaatacca agtattgggg agaatgtgga gacactggag ccctcttaca gtgcaggaag  13680
aaatgtaaaa tggggcagtc actttggaaa acagtttggc gatttcttaa aaagttaaac  13740
acacacttac catgactctt aggtttctat atgaaataaa tgaaaacatg tgtccttatc  13800
catagaaaga catacacaaa tgttcatagc agcaatattc ataatagccc caaactggaa  13860
aacccagctg tccttcaact agtgaatgaa taaacagact ctgatatact caaagtagcc  13920
ggagatagga gtggaactga ctacaagaaa ccttttgtgg ttatagaaat attaaaaaac  13980
tagatagtgg tgatggtttc ccggtagttt taatttattg aaactcatgg aactacacac  14040
ttgaaaatgg gtggctttta tagtatgtaa attatacctc aatgtaaaaa caaaggaagt  14100
aggtaacaat cttaaaaatg aatatatatt ttttgcatct gcttttattt tgggacctgt  14160
gttctcccaa gtatgtttat tggtttatgc agtggagtta tcatcaagtt ctaggaagaa  14220
ggaatacttt taaattttcc agaaatttga gagaagaaga attataattt ggggaaattc  14280
tacttgttta aagaatctcc tatttctagt gttgtggaat ggaaattaga attggttact  14340
ctttgtctta aactttcttc ctgggctttt cagattaaac cattatatga acatcttcat  14400
gcctatgtga gggcaaagtt gatgaatgcc tatccttcct atatcagtcc aattggatgc  14460
ctccctgctc atttgcttgg taagaagccc catgaattct tcgtgtactt ggctctttgt  14520
tatttctaac aataaaattg ccttttttgag tgagccttaa cataaaactt ttgaaaaatt  14580
ctgtaagtgg ttagtaacat tgtagaaatc gcattttgaa agcattttct tcaaccaaaa  14640
gtctatttta aacaattctc tattgtatta cttttttttgt acataaagag ttattatttt  14700
ggctgcaatt caaatgataa aggggttatt taagataact agagaaagaa ttacaggctc  14760
aaatgagagt ggaaatgggg aaaataattt ttagtattca agttgattgg ctaagctctt  14820
aaggtggaat ttgagatttt agtatcatat tgtcagagct tggttggctg ggggtggtca  14880
ggggtaacag aaggttatag cttgagcgaa agcttcctaa gttcattcta gacttcacca  14940
attactcttg ctgaaaagtg cttggcttgg aatcgtataa gtgaagaatg aatgaaagtg  15000
accatcttcc cctctcccac cgcagcagct gaggccaaat aaaatataaa tatttgaaaa  15060
tttcatgcca tgcatatata gcatttctac tgtagtcaaa ctaagttgct ggaagctaat  15120
ctcctccaca gccatacctc gtgtctgtca gcaggagaga atgcggagaa aggacctgtg  15180
gaggctttta actctaaagt aatatggaaa tccttcctac aatgtcaatg gcaagcagta  15240
tttagtaatt cagtttctgc ttaaacctgt ctggtgtgat gggataattt cttcattcca  15300
atatagacta atttactgct acatggaacc aatgtaatac aattctacct tatgtggaac  15360
ttaagcaaca cccctctgat gccttccatt cattagccct atttccatgc tatgaggtta  15420
cccagaatgt caattcctat tctacaagat gaccttccag atattcataa agaaccatca  15480
tataagatat agcatagtac ctggtgcaat acattttagt gactattatt gttattgtca  15540
tgtttaccct attttctttt gtcaagttaa atatcttata cattatcaac cattccttaa  15600
aacctcactt ttctataatt gttctccttt caatgagctg tactttgtca atgtccctcc  15660
tcaattatca tgcttagaga tgaacagtta ctccagatga ggtttgacca acataaagaa  15720
agacatggta ccatgactac ctttgttcta gacactatac ttctattgat ttagctcaag  15780
ttcacattta tgctttagaa gccaggtcat actgtttgtt ggctcatttt tggtctttta  15840
catgtggact gtgctttagc ctgatgtcac atatatgttt ttatgatgga taggtttttc  15900
tttaaaattt aagcatagga cttcacatgt atcactacta aattttatgt tttaaaatat  15960
```

-continued

```
aagtttaggg agtactttta ttttttcag agtctcgctc tgtcgcctag gctggagtgc  16020
agtggctgat ctcagctcac cgcaacctct gcctcctggg ttcaagcgat tctcctgctt  16080
cagcctcctg agtagctggg attacaggct caagccgcca tgcccagcta atttttgtat  16140
ttttagtaga gacagggctt caccatgttg gccaggctgg tctcgaactc ctgatctcaa  16200
gtgatctgcc tgcttcagct ctgcaaagtg ctgggattac aggagtactc ttcatgaagt  16260
ttgttgcccc attttttgg caccaggatt ctggtcctgc tcttggattg actttttcta  16320
gatacatctt cttttttatg gtccctggcc ttggaataca acttaacatt tgtttgagat  16380
gtttacaaag tcaccaagtt aagtacacga atataggaat aaaagtggaa tttagttacc  16440
agttagtaga agttcctgaa tgatgatctt atatgatctc ttttgaagcc aacactagga  16500
attactaaca gcttaatttg taatattttg taccatggat ggtagattat agaaatctct  16560
ttctaattta cagtgtcaat gatggtccat atatttaata aattatgtct acatttctgc  16620
tgtgttgtca tatactaaca gattcttttt taaatatagg tgatatgtgg ggtagatttt  16680
ggacaaatct gtactctttg acagttccct ttggacagaa accaaacata gatgttactg  16740
atgcaatggt ggaccaggta ggaaaaagag cccttaaaaa ctaaatctaa attctcaact  16800
tcatttattt ttatgtcatc cttctatttt tatttttatg tgaaaccatg taaataaaaa  16860
atttaagcta attgaaattt atttcttatg tagctatagt ttcatggaaa agcagtttac  16920
aatggcctca gataacttga attgcaggtg tagtattgat ctcattgaaa ggtatttgaa  16980
atggagatta cctgagtttt ccattaagcg gtaagatgta gaattgtcaa ctggttggta  17040
tcactcattc caaagtttgt cattgctaag taaccagcca gtaatctcta tggatagtaa  17100
aaacaagaat attatgaggg gatttttgca tatttaaaaa attattagtg ttaaaaatat  17160
tacaagaatc tttaaaacaa ttttaagtaa catctttatt actactttgg tttaattatt  17220
taaatgtgct aggttcctca aaacacaagt aagtacatag cccatggacc caataaagca  17280
actacacaat cgagactaca aagcaaccag ctaacaacag catgacagga acgcttcacc  17340
taacagacag agagtggcaa attggagaga aaaacaaaac ctaaccttct actgtcttcg  17400
agattcatct cacgtgtaat gacacccatg ggctcaaagt aaagtgatgc agaaagatct  17460
atcatgcaaa tagaaaacaa aaaagagcag ggggctgcta ttcttgtatc agataaaaca  17520
gactttaaac caacaacagt aaaaaaggac aaagagggtc attacataat gataaagggt  17580
tcaatttaac aagaagactt aattatccta aatatatatg cacccaacat tggagtatcc  17640
agattcataa acatagcact tttagaccta ggaaaagact tagacatcca gaaaataata  17700
gtgggggact tcatcacccc actgacagtg ttatacagat cattgaggca gaaaactaac  17760
aaagaaattc tggaaattct ggacttaaac ttgacacttg accaattgaa cctaagagac  17820
atctatagaa tattccaccc aacagctatg gaatatacat tcttctcatc tgtatacgaa  17880
acatactcta agactggcaa catgctcagt cataaagcaa gtcttaataa attcaaaaaa  17940
ttaaaattat gccaaacata ttctcagacc acagtagaat aaaaatagaa atcaatacca  18000
ggaggaactc tcaaaaccat gaaataacct ggaaactgaa caacttattg ctgaatgact  18060
tttgagtaaa caatgaaatt aaggcagata tcaaaaaatt ctttgaaaca aatgaaaaca  18120
gagacacagc ataccaacaa catatctggg atgtggcaaa agcaatgtta agaggaatgt  18180
ttatagtgct aaatgcctac atcaagaacc tagaaagata tcaaattaat aatctaacac  18240
cacacttaaa ggaactagaa aaacaagaac aaactagttc caaagctaga aaaaaagaga  18300
```

```
taactaaaat cagggcagaa ttaatgaaat tgagacctaa aaaatcatac aaaggatcaa  18360
caaaatgaaa agtcagtttt ttaaaaggat aaacaagatg gaaagacctc tagctagatt  18420
aacagagaaa gagagaagat ccaaataagc acaatcagaa atgacaaagg tgacattgca  18480
actgatccca cagaagtaca aaccttccta ttgagtacta tgttcatatc tggttgatag  18540
gaccaataga aacccaacgt cagtatcaca caatataccc ttgtaacaaa cctgcacatg  18600
tactccctga atttaaaatt aaaattaaaa ttaaagttaa aaaattatca ggccgggcac  18660
ggtggctcac agctgtaatc ccagcacttt gggaggccga ggtgggtgga tcacgaggtc  18720
aggagatcga gaccagcctg gccaacatgg tgaaaccccg tctctactaa aaatacaaaa  18780
aaaaaaaaaa aattagctgg gcatagtggt gtgcgcctgt agtcccagct atttaggagg  18840
ctgaggcagg agaatcactt gaactcggga ggcagaggtt gcagtgagcc gagatcatgc  18900
cactgcactc cagcctgggt gacaaagtga gactctgtct caaaaaaaaa aattctctgt  18960
gttcccttct gttgatgaaa tggtattata gttataatta tgtatatttg ttcattcaac  19020
taaaattcta cgtttctgag tagaatatct aatcatattt ctatttgcct tataaaattt  19080
attcagataa ttgcaccata atttactatt tgtgcattgc tgaacctttg cttgttaata  19140
gttttacatc tgtaagaagc aatgcaatga acatcttcac atacataaca tactcctggg  19200
aaaagtccac tgcagaataa aaagtgaaac tgcaagggcc tctaaactct tgtagctgtt  19260
gtagctccac tttgaagttg agcagcagta tagggccatc ttgatgtaga tttttagtct  19320
ttctaaaggg tttttacacc cgtctcttct attgtcatct ctgactcagg ataggtattg  19380
tgacagctcc atgctatagg tgaggaaact gaggctcagg taaatgattt gcccaaagtc  19440
acaaatcaca cagcctcatt ctttctgttt tttttgtacc aattaaccat cctcacctgc  19500
ccctgccacc ttcccactac tctttccagc ctctggtaac catccttcca ctctgtatgt  19560
ccatgagttc aactcttttg atttttagat gccataaata agtgagaaca tgtaatgttt  19620
gtctttctgt gcctggctta tttcacttaa tataatgacc ttcagttcca tctacgttgt  19680
tgcaaatggc aggatttcgt ttttttatgg ctgaatagta ttccaatttg tatgtgtacc  19740
acattttctt tatccattca tctactgatg gacacttagg ttgtttccaa atcttggtta  19800
ttgtgaatag tgctgcaaca aacatgggag tgcagatatc tcttcaaaat actgatttcc  19860
tttcttttgg gtatataccc agcagtggaa ttgttggatc atatggtagc tctattttta  19920
ctttttttgag gaacctccaa actgttttcc atagtggttg tactaactta cattccttcc  19980
aacagtgtag gagggttccc ttttctccac accctcatca gcatttgtta ttgcctgtct  20040
tttggatata aaccaaaaaa tttttcataa atataatttg ggtggctgca cattattcta  20100
tttttcaaag gtatcattat ttatttaacc attctgatgg tcgtttcaac tttttctcta  20160
ttaaaaataa ttctcaatgt aattgttgaa tctaatttct gataattttt taggttagtt  20220
ccttagagac agcattactg agacaaagag aagaatttca aatgctatcc gtgtgtgtta  20280
tcaaattacc ttttggaaag gttatgccaa tgtatatatc caacagaaat aatgctgcta  20340
ttttaaaaat gacattagca ctttttttcca ttttaaaatt ttattgtaaa ttgacattta  20400
ttattgtata tatttatggg gtacaaggtg atttcatgat ttatgaatac aatgaaaaat  20460
aattaaataa agctaattaa catatcaatt acttcacata cttttttttgc agtgagaaca  20520
tttgaaattt actctcttag caatttcaaa atgtacaatg ttctattatt aactatattt  20580
actatgctgt gcagtagatc tcaaaaaaat aaaaccaact tattcatcct gtttgagact  20640
ttgtacgctt tgaccatcat ctccccgttg cccccacccc atagcctctg taaccaccat  20700
```

```
tctactctct gcttctacca gttccattgt tttagattcc acacataagt gagaacatgt  20760
ggtatttgtt tttcggtgcc tggcttattt aatttaagaa tgctgttgtt ttgatgctgg  20820
aattaatact gttctctttt cccaggcctg ggatgcacag agaatattca aggaggccga  20880
gaagttcttt gtatctgttg gtcttcctaa tatgactcaa ggattctggg aaaattccat  20940
gctaacggac ccaggaaatg ttcagaaagc agtctgccat cccacagctt gggacctggg  21000
gaagggcgac ttcaggtagt ggggctgata cttacacaac tgatactaaa tgggagacaa  21060
cagaggcagg ctgaagttta acttgaattc tttctctgct tttctgagca cagaaaagat  21120
aagttaattc tccttgaact aaggctggga gtccaggaga gcacatttgg gttttcccag  21180
gaaaagagga ttgccagcag gctctaactt gaacctgtgg acaatctgct ttcttggaaa  21240
tatcatgcat ccattggcgt tgtatggtaa tggggatggt tgcacccata tcaggaaaga  21300
tttggtgcta agatttttgg aagatggaca tatgaatcac acattgatct tcccctccat  21360
gtttcactct tgtgaatgag acagaatagg tgaataaata cgcttggatc gaagggagaa  21420
agtggtacat gtcgtaagag agacacaggg catgctctat ggagaactgg aagaaaactg  21480
accacatttg caataggaga taggatcaga ccgtgcttta caagtgggat ttgaattagg  21540
tttggaaaga caagaaggat tcagatacac agagtcggga ggaggaccca agctgtgaga  21600
acagcaggat caaatacaga gaggcaggac ctgacctgca tactgaagtc ggcaagttag  21660
gctagaatga gaaataagtg aaggagagtt tgtgtaatgt ggcagaatga gcacaggctt  21720
cagaatccta ggtgtgtcac ttaatgacta tgcaaccttg gacaaggtat ttaactttct  21780
ttggtttcag tttccttatt ttataaagta gaatagtaat tcccaggttg caggcttgtg  21840
agagccttag gttggattcc ctagcttgaa aaggagatcg ttttacaagt gcttcattga  21900
ggagagctct gaggcagagg ggaatgaggg aagcaggctg ggacaaagga gggaggtaag  21960
taagaatgtg atctttactg gaaacttggc ctcagcctta tcccatgaag ctctctggag  22020
cataacttga gccacagact aggccacacc tcaagacaag ggggctagcc ttttatatca  22080
ggcagtcttt ggctgtggac tgccccagag tatgggggag cataaccccc atttagccaa  22140
aggcagtgaa gggagcagct gtaggccctt atcagctgtg actcaggcag ctaggggatg  22200
gtggataaag tcttggcagg cccgcaccag cattgactag ggtagggatt ggatctacag  22260
tccttttctg taaagggcca gatagtaaat agtttaagct ttgcagatct ctgttacaac  22320
tactcagctc tgcccttgtg acatgaaaac agccatagac aatacacaaa ccaatggatg  22380
tggctgtgtg ccaataaaaa tttatttata aaaacaatgg ctggccagca ggccatagtt  22440
tactgatgcc agtactagag tgaggcttaa aaatgagaaa gtataagtaa gttttcaagc  22500
acagaatctt acatacagta ggcagtaaat atatagtagt tatttttata attatttcaa  22560
aagagaatag agagaaacca aattagaaaa gtaggttggg gttgtgaaag gaaaatagat  22620
ttactgagca tgagatgaat acataactga atatttcctt accttccccc tttctcttgc  22680
aatgtgtgaa ttaccatgcc ctcccactat cctctccagc tcacttttct cctataaatg  22740
ttgaagccct caaaattatt tttggagaaa ggcacaaacc acagactgtt tctataaatt  22800
ctgtgttctt ttcttctggg catgttctta accttggcaa aataaacttg tgaattgatt  22860
gagacctatc tcaaatagtt tttggtttac agggtcatat tggtgtataa aaggtggctg  22920
agtttattct tgagcaatga ggaggcctcg caggatattg gagggggtgg tgacatgatc  22980
caagtggtat gaaatacatt taggaatcta ctgatgtatg acccctacac ccatctgaat  23040
```

```
gaaaatgctc ttgctaagtt aaaaaggacc accatctcat tgccaaatgc agttcttatc  23100
ccactgggct atagcagcat ttgacaagat ttacaagttg tctttcaaat gctttttttt  23160
tttaaccgac ttccacattg tcattctttt ccagatttcc ttgacctctc tgattgtact  23220
ttctccgtct cccctgaata atcttcctct ccccactcct taggtacttg gaccttctaa  23280
aggtttatct ttggtcctct tttcttgcat tctatacctg ttccatggcc catcatatct  23340
atttcccaac ttacatgcta atgattccca agtttcaatt tgcagcccct tctactattt  23400
ctctatcctg gcaataccaa acagcgtgca gtgtcctgaa tgccacattt ccacccccct  23460
gcccctaagc ctttctcatt gagcactaga acgtcaactt ccatgtcatc taccgggcaa  23520
actcctgcac attgattaag gtccaaattg ctcattgtat cctcagtcat gcccttcttg  23580
gtgcttctag ggaactgtgc ctacattcac tcatttttac gctcaaggct gtgtgtactg  23640
atcacttata gagtacttgc ctcagagttc ttgtagcgga gaactctgct tatctgtctt  23700
cctgttagtc tatgagcaag agaacaggat tcagctgtgc ccattgcttt atattgagca  23760
actagtattg tctctaggac ataagaggtg ggtactcaag attcactggt gaataaatct  23820
tggaaagatg attcatgcta ccaaaacccc atacaactcc actgtaatgg ttaaatgaaa  23880
gtcagtgaga ttcattttca tcttgtccat tttcatgcag gatccttatg tgcacaaagg  23940
tgacaatgga cgacttcctg acagctcatc atgagatggg gcatatccag tatgatatgg  24000
catatgctgc acaacctttt ctgctaagaa atggagctaa tgaaggattc catgaagctg  24060
ttggggaaat catgtcactt tctgcagcca cacctaagca tttaaaatcc attggtcttc  24120
tgtcacccga ttttcaagaa gacaatggta tggacatttt ctcatggctt gttttggagg  24180
ttctttaatc tgatatggga aaaggtattt attatcttat gtaggaaata tttacttttt  24240
gccacataag gtatgaggta tttatgggta actggaaatt actactggtg aaaaaattta  24300
agtatatatc agaacatgtc aacttttggt tttgtattat tgaaaaggga ataagagagg  24360
taactgaatg aatggacttg ggatcctgtg aaatatctaa cagaagtttt tttcttaaag  24420
atgatgaaac agtctcacag aactgaaatg gcttgtccaa ttagtgtcag cattctaact  24480
agacccctct ggttctaggt aaaaacttcc caaaacttta gagttggaat atattctaaa  24540
aaccatttta tagaggagta aactgaagac aagagaggga aagtagcccg aagtcaaaac  24600
gcaatgtagt ggcggaacca gaacaagagc cctaatctaa agtcttttcc ataatattat  24660
gcaaagcaaa gtgtagcttt aaattttgga attcttaaag aacaggtgtt taatatcaag  24720
attagaaggg attgaaacat tttgttcatc ctgctgaagc gtgaatttcc cctgtaacat  24780
ccccttagat ctgtgctatc cttcaacatt tctgcctgag gcagcccatt tccttttaga  24840
tgccttggac ttgatggaac atgacaaatg ttcaggagat ccaatttctt cagtgaggat  24900
gccatggctt ttgattcttc ctcataaatg gaggacaaat agagcctaat accttcttct  24960
cttctgtata ttctctcccc tatttttagt tatttgtgac ataaagatca gctcctctgt  25020
ctggagcatt tggtcgatga ggtcaaggtc atgagctcca tccttgagta gacaattcac  25080
tttgccttga tctctggttc cagatacttg gtgatcccac aagggcctgg gagtgagcca  25140
gtgtaaagcc tatcatcatg tttgaaatag ttactgtaag cacagtccta gtggattaca  25200
gaccagtagc agcatcctcc catgaagaca gtaacaaaca aaggtagtta acagtaacca  25260
tacctgcttc ctaattttaa aatatcatta attcaagtca atgaacagat attttattat  25320
ttttaaatat tccctgacag caggtaaaaa tggttgatga ctatgtttct taagatgata  25380
ttagatcagt gatgaaataa tctgtacaac aaaccccatg acacgagttt acctatataa  25440
```

```
taaacctgga cacatacccc taaacctaaa ataaaagctt tttttgtttt tttttataaa  25500
aaagatagta ttagacatgg ttaaaccacc ggtttggaaa actcctgctt tttttcttga  25560
ctctgcccct gatttgtgaa taatgttaaa taaattcctt tattccttcc attcctccct  25620
ccctctttct ctttctttct tcttccaaac atatttatcg agcacatact gtgtgcaaga  25680
catttttcta gacactggag acacagtgat gtgaaaagta gataacatcc cctgcttaca  25740
tttcaatgca tttccttcat acactagaga tgaactccac tgcctcttta tgtcactaat  25800
aaaggataaa atgaaataac atgatttgtt aaagcatttt aaattcttgg taaggaagat  25860
atccttacat ttaaagtaca ttgtactttt caccatccag tggatagtgc cctccaggag  25920
ggctcttttg tttcatttcc cctccctggt ttacaggctt ttcactgaat ctgtttagta  25980
tttgtttatt taacaaagac tcacagaagg catcacgtag cagacatggg actaagttat  26040
acagtcttaa atgagacatt aacagtcact gacttcatgg agctttccag aataaacagt  26100
gtgactggga aagtggatga aatagctcta atgaactctg ataagaggta tttaagggag  26160
gaaactgaaa ctaatgaaga aaatgaggat tagaagtaac tttgggtttt atttacctgt  26220
tctgttccag ggcttcaacc tactccaaat cccttagctg agaaaataaa tatatacata  26280
tcattatgaa tactgtcaat ttttctcatg tatccttata gtaagtacat cttgaggaat  26340
aatattttga ggttaggaaa attctcttta acacaaaaca tccactgtca tcttcatcgt  26400
aatatttatc cttttctatt ttactttcag aaacagaaat aaacttcctg ctcaaacaag  26460
cactcacgat tgttgggact ctgccattta cttacatgtt agagaagtgg aggtggatgg  26520
tctttaaagg ggaaattccc aaagaccagt ggatgaaaaa gtggtgggag atgaagtaag  26580
tcaatgaata tgcaatcagt aaaatgtttt ctaatgagtt tgctgtgtat ttaaaagcat  26640
ttgactggcg tgtacacaca cacacagagg cacacattaa ctaactactt tttgtatttt  26700
tagtttgtta tattttatat tttagtctcc atttggatac catctcctca gataaaattt  26760
ccttgggtca ggtgacacta cttcatactc tatattctta agtattggct tactcattaa  26820
actatgatat tatgttgaaa gtgatcaatt tattcatttt acatattctt ttatccagcc  26880
ttttaaacaa aacggtgacc ccacatttta ggcaaagcac tggggatcca atgttaataa  26940
tttcaggtat ggtcctcaac cccaaaaaac gtttagttta tggcaggatg tggaaaatta  27000
aaccactgca atttgtagtg ttgtgatggg agggtacagg gtccgttagc gtccagggga  27060
gatccaaagc ccaactgggg gtgtcagatg aggagaggca tttaagccct gagaaaggtg  27120
tgggtgtaga ggggaacaca gagaattcca agctagagag aacctgacac atttgggcaa  27180
cagtgaccat ttccatggtt gcagcactac gttacttatt gctgtgtcac aagtgcctca  27240
cactgtgcct gtcacatgca agtatgaaat aaataggttt ttggaggaag gaattataag  27300
agaaaaagaa aaagaaggaa aaaaagaaag gagagaggga gggagagaat ggaaacaaga  27360
aagaaatcta tcttcttttt accatcatag accctggtca attatttctt tctttatttt  27420
tcttatattt tctttttgaa gtgaagaact catgtgtaac aagcagttcc acatgcacag  27480
gtttaaaaca gtacacttct tctgtcaaga ttctctctgt taacataaat cgtacttggg  27540
aggaaagacg cagcacctat aagaactgtt gccagtgttt aaatattact gaagttatgt  27600
ctacaatgat cctgcaattt taaaggaaaa atgtattcca tttaatcaaa gccaaataca  27660
tgattttgct accttttttt ctggttggat taatcttttg acccctctta gcttatttta  27720
aaggcacatg gaatcagatc cttagagtga ttcattaatg catcaattgt tcctttgttc  27780
```

```
agtaaatata aattaattct ttctgtagtg tcaggcacca tgtttgacac tggaattaga  27840
gagaagacca agacacagcc ccaccctcta ggagctcaag tctctagggc aggaagttac  27900
tatagttgaa taactacaaa acggggagat aaatggcaaa ggaggcacaa ctagagaagg  27960
ctaaaggaga ttgaggggtt aattctgcca gaaggtggat gggatcaggg ccaggcttca  28020
cagaggaggg aacacttgag ctaggtaggc gtggagaata agtaagattt caattttatt  28080
aaattctctc tgccaggagt acatgaagtg tggtgcctga gaggaattat tagggctttc  28140
actgtacatt tttggccatg caatgcactt tatgaatgtt attaaattag tcttttgaag  28200
acatagctat tttccaaggg tatattctgg ctgaattaat taaaactaag agataactac  28260
ataatgagct ttactgtctg attttttaaa aatttttatt tattttttat ttttgtaggt  28320
gatttttttt tacattgttt ctatttcacc caacaaccat ttctaatgta aataccattg  28380
attggctgga cacggtggca cctgtaattc cagcattttg ggaggccgag gtgggcagat  28440
cacttgaggc caggagttcg agaccagcct ggccaacatg gtgaaaccct gtctctatta  28500
aaaatacaca aattagttag atgtggtggt gcacacctat aaaccaagct acttgggagg  28560
ctgagatggg agaatcgctt gaacctggga ggcggaggtt gcagtgagcc aagatcgtgc  28620
cactgcacta cagcctgggt gacggagtga gaccctgtct caaaaaaaaa aaaaaaaaat  28680
ttgattgatg aaactgcact agttatgccc acctgcttgt gatgcttgtg atgggtgatc  28740
cacagctaat gtattgtttt cttttctccc caaaggcgag agatagttgg ggtggtggaa  28800
cctgtgcccc atgatgaaac atactgtgac cccgcatctc tgttccatgt ttctaatgat  28860
tactcattca ttcggtaaat tacagttttc ttgtttctgt ttaacttcta gggtttgtgg  28920
acagctgtgc taataacgac aaaaagtagg gataaatgaa gtgataatta taatttttct  28980
atttccaccc ataactacca agctcaatac agatgctcct tgctttacaa tggggttaca  29040
tcccaataaa ctcatcataa gttgaaaata ccttaagaat gcgctgaata cacctaacct  29100
atggtacacc aaagcatagc ctagtctacc ctaaacatgc tcagaacact cacattagcc  29160
tactgttggg caaaatcatc taacacaaac cttattttat aataaagtgt tcaatatctc  29220
atgtaattat ttaatactgt gctgaaagtg aaaaactttg ggtacttacc attaacatat  29280
acagctgaaa gcgctattgt aaagtcgaaa aatcaaaagt ccaaccgttg taagttggga  29340
actgtctgta tagatgatca atttcaattc aatttaaact aacacaattt attgggttaa  29400
attaaacttg tgtaagatct tgtccccgtc atcagcaatc aatagtatca ttgggagaaa  29460
taaaaagtag ttttgtcttc ttgttactgg cagtttattg tacattgtga tagagaattt  29520
ttaacttgaa gtccaaaaac atatgttctt cacctactaa ccccagtcct tgaatttgct  29580
ggagctcagt ttatttgtaa aatgaaaata atattatcga cctgttataa ggatggattt  29640
gcatcattta tgtgaaaggg ctattaatct gtaaaacaca aaacaaatgt tagctaacat  29700
ttaacagagt aatattgcca tgtttatcaa cagatacata aaacacaaat aggttatgat  29760
gagtgtagag ttcatgtctg gagaaagaga tttcagagat ttgatcagta tctctttggt  29820
tacttgggct ccagatttaa atatatgccc taatctataa ctctaagaca gtaagtaaac  29880
acgggactgc ttttttgttg ctttgtctcc tgtgcagata ttacacaagg accctttacc  29940
aattccagtt tcaagaagca ctttgtcaag cagctaaaca tgaaggccct ctgcacaaat  30000
gtgacatctc aaactctaca gaagctggac agaaactgtt gtaagaaata cctcaaaatg  30060
ttgaacctct cctagtattc agtattactc atttccatgc ctaggtttgt atttgatttc  30120
tttgttctaa aaagaaaatt ttatggcctc aaaatgtcct catttacaaa ccaaacattt  30180
```

```
aatttgtggt cagacaggaa cctagaccat acaacaattg ggtgggccac ctcttttctc  30240
cctatcataa ctacagccct ctcttcctgg taattggaag gaaagagcgg tttagggtgg  30300
aatatatctg ttaatatgca ttcttttctt atctgccaga agcaaattta gccaagtcaa  30360
agagaagaaa ccatagatca tagatgtaaa tatatgtaca tctggaaccc ctcaaaaggc  30420
cctgaacccc ctttttttgt gtagcaatat gctgaggctt ggaaaatcag aaccctggac  30480
cctagcattg gaaaatgttg taggagcaaa gaacatgaat gtaaggccac tgctcaacta  30540
ctttgagccc ttatttacct ggctgaaaga ccagaacaag aattcttttg tgggatggag  30600
taccgactgg agtccatgtg agtacaccca gttgacaagt ttcacaccca ttccttgtct  30660
acttcgtcta gtctcctttg gccccagtct catgaggact tgtgacacag ctgagaatgt  30720
ttctttctct atagtacctg cttctttctc tgctatggtg acagctgcca ttttatggga  30780
gaaaaatcac aactgttgag cacctatgta tgagacatag tgaaagcaac tgtacagaca  30840
aacacacaca gatgcatgca catgtgtgca tacacataca agagtgtgta ctctttcaag  30900
tctgttttat tagtctcatc tttaaaatac atattataac tgtctccaac caactgtact  30960
cgaatcctgc tttccaaaga caaatacttt ttttaaaaca attttaatgc tattatctct  31020
tctttctggc agtcactttc atatttctaa ataattttct tatattgcta ttttgttatt  31080
gctcagtttt aaaccttcgt tttggtctac tcttccactt ccatttcttg ctcttccaat  31140
aaggccttat aatgattttt agtaaaacag ttatcaatgt ttacatcact atgcctgaag  31200
agccaagtaa tgtattattt tgtgtccttt cttatgtggc ttgttgtttg tctcaaagtt  31260
tctacttgcc tgaatttttc ggcttaccta atttgctatc tacgttgtat ttgtttttct  31320
cccaaatatt tcaacatatc tattcttttc agtctcattt tttttcccta gagacttccc  31380
tcttggagtc ttatattctc ctttcccaac atttgttgtt ctcctgggtt gaatccactg  31440
cttcctagat tccatgtctt ctttcttgga ttacctcttg tttttctgga gcatagcctc  31500
ccacagactg tccaagcagg ggcacaaggg gtaggaggat caactgttct ccaaagtggt  31560
tttaaccaca ccctgacttc cattcctctt cttttcagcc cagtattatt ttcccaccct  31620
cacctgtgct tgaattccaa acctcttttg gatttttttgg ctctttgtgg gtctgtgcct  31680
cctctgtgta caaattaggt catggcttcc tgtccctgag aaagcagtta cccctgtctc  31740
atcatttctc gttttccaaa agcctgttga tacctttaaa agatcccttt actatcactt  31800
tagtgggatc tttggaggaa aaggaaataa gcacatgtgg gcaatctgtt gtctgtaacc  31860
agcagtctgc tatttctctt taatcagatg cagaccaaag catcaaagtg aggataagcc  31920
taaaatcagc tcttggagat aaagcagtga gtattctgga cagtgaattg attatttttg  31980
agtgcacagt cttcacttaa ataggacaca ataaacccat ttcagtgtga actgaaagaa  32040
gagaggccat gtggttcttt tcaaaactat aagttccaga ttctggcctt tgcctttggg  32100
tttttaaagt aacctattcc ttattggata agctattcct acttcttatt gccttgaagg  32160
tgttatgaac ttcaatgaga aaatatctgt atcaatcctt aaatatcaga taccaatcct  32220
ttcaattgac tctcgtcacc attactttta ttctagaaag agaatatggt tatattttga  32280
aaggtagttt gtttttagaa gcggtacagt taggtttttt tagtttgttt tgttttagtc  32340
aatcacctgt atcctggctt cactcagagt gtggcccatg gtccagcagc atttgaatca  32400
cctggaagct tgttaaaaat gcgtaatttc aagcctagcc ctggaccact taatcagaat  32460
ctgcatttta gcaagcctcc aggtgatttg tacgtacaat caagactggg aagctctaat  32520
```

```
ttagaacact gcttctcaaa cttggctgca cagtggaatc acatgggaag tttaaaaaat  32580
attaatgcct aggttataca cctccagaga ttctgattta attgttctgg ggtatggagt  32640
caagagttgg gcatcaagag tgtttaaagc tccccaggtg attctagtca cagcaaagtt  32700
tgagaaccac ttatttaggg aaatgcattt tgggggtaac aaaatatttt acaggaaatt  32760
atgttattta caccttaatg tgaattattt acttagctat tgctctgtcg ttaacacctg  32820
tctcagatga tccagtctga ggaagtggta gctttgattg ggaaagagga gaggaaagag  32880
tagtctcggg tagatggggc tcaaaagcct gagagtgggt atgacaccct gaaggctttg  32940
cagggttaga agtcaatctg ggactattgg ataaaatggt ccaagatgct acagcaaatt  33000
gttgtctgca ttggatagat ccaaagattg tgtttctacc cccttacctt tcctgaaaag  33060
ttaaacattg tccaagattc aataacactt ttagtataat tttcatagtt aagacatcaa  33120
aacataaata actcaggagt aaaaagatga acattcaaga aagaaaaaat gaaaatggaa  33180
gtgcatttct ttccaatcat taagagttca agttcctatt tcataataat cattgggtga  33240
ttgtgggact atttctctgt catattttta ttagctcttc cttggcttaa tacattttaa  33300
ttagtctcgg cagatcagga tattttcaat tatctttttt cttgacattt atactcatcc  33360
tctttccatg cagtgagggt tggtaaatag tgttcaggga gtttgattct gtaatgttct  33420
gaggccaatt cactgagcaa caatctgttt tgatgaaacg agatcatata tttagtgcat  33480
ctacacaaca gggtcagaat atctgctcag ttcaaactat ttcatggtga attccaatgg  33540
atctatggca ttattttgag aactcagcct ttaaaatctt ttatatttta tatttataga  33600
gatagtagcc agactgttat tagtaacaat attaataata ttattactat taaaggaact  33660
cctctaaacc tcggtgaaac caagctgaag tgaatgtaac aattcttttg tgaaatatta  33720
taattttta aagggaaagg agaaacatac aactagtgcc attcattgat tcctactgcc  33780
agctactgga ggaaagagtg aatgctttct tttaagtctt taaaagctat gcaaacataa  33840
gctatttgtt tagcactgga aaacaagaac aaacagatta gcttgctgtt tacaaagtgt  33900
tatttttcat ttgaacgtca agtttttctt ttacacttat agataagtac atttctgaga  33960
acgtaccata aaaatagtaa aaactgattt tgtccacaag gtacagacat tttgctacaa  34020
aacccacaac ttttgtttga ctcccatcgg taaacctaca ctcaaggtgt taatttcagt  34080
ttacatcaaa ctaaagtaaa aggacccgtg aacccaatgg ttcctaaagc atggttgcct  34140
gaccagcagc attaccacca cctgggagtt tgttagagat gtaaattatt gggtttcatc  34200
tcgggcttcc tgaatcagac gctctagggg tggacccagc actcagtgtt gtaactaacc  34260
cttcaggtga tacggatgca cacttacatt gaaggtcact gacttaatga atagcaagaa  34320
tctctggaat attaagaata attcttgagg agtatcagat tataaatgtg tcttacgagt  34380
ccctctgagc agtgtctttc ttctgaattt gcagtatgaa tggaacgaca atgaaatgta  34440
cctgttccga tcatctgttg catatgctat gaggcagtac tttttaaaag taaaaaatca  34500
gatgattctt tttgggtgag ttgatttgct gggttctcaa attactccaa ctaggatttc  34560
tcttactctt gagtctgagg agatactctg cctaaacttt tcttcaagtg aaattgataa  34620
aaatctccta gtaacttata cttctttggt attgtggaat ttgggtgact ccatagaggg  34680
ctgatcgtgc cttatttgac tggtaaattg caagagtatt gttcttacta aacagctgtc  34740
actctcttct cagaatgctc tcatacaccc tcagcactga aagaaaaaaa aggcagaact  34800
tcctgccttc attgacctat attctagtat gtatgttgtg tatgtgtcta tgtgtgtaat  34860
atgtaagtga aatatagagt tacaaggtac taagtgctag gagaaaaata taaaagggtc  34920
```

```
tggggagggc tggtgtgtgt gtgtgtgtgt tgggcagggg gtaggtcaat tttaaccaaa  34980
atggtcagaa aagacgtcac taatacttga acaagtatat gaagcaggag agagrgagmg  35040
agagagcgag agagcgagag agcgagagcg agagccagca atgcagacaa tggggaaagt  35100
gtctcagctg ggggaaacag caggtgcaga ccctgaggaa ggaatatcct cagcctgtta  35160
aaggaacagc aaggaggcca gtgtggctgg agcagattag aagacaagtg gagacatggc  35220
caggacgatg ttagggcata gaggaaggag ggagagacaa aaggtcatgt gggccttgaa  35280
ggccattcta aggactttgg cttttattct gagttagatg agtagtcact caagggctat  35340
gagccacatg atctacctta ttttgtgcta ggatcgcttg acagctgtga gagcacagtc  35400
ctgtcacatc atatggtaga ccccactcat taccttcatc catgggtgca acacgacgtt  35460
ttctgctggg taggaccagg ttgtgggtgt aaatccgtgt gtggtactca gccatttctg  35520
cccaccacat tgtttgccac aatcctgggc caccgattat tccttgttga ttctcctgct  35580
gttttcagtt tggaaatttt ctataattga aaaagatgtg ggttttatat aaaggcagaa  35640
caaatagtgc caaaacttga tatcacaatt tttatgtagt tgatttcatg tgctttgggc  35700
agcattaatg ttttttttga caattacatc ctctcattgt ttgccctccc ccatgtctct  35760
ctatcctgtg attctctctc taatctcctt ttcaccagca ggggaagtct tcattctctt  35820
gattgtgtcc tctgtgccac aagtgaagat gtttgttttg tttctctaca gggaggagga  35880
tgtgcgagtg gctaatttga aaccaagaat ctcctttaat ttctttgtca ctgcacctaa  35940
aaatgtgtct gatatcattc ctagaactga agttgaaaag gccatcaggt gacattttac  36000
tttcatctaa gggtgagggg gttaccaaat acaacaacaa taaccagtat tttgtgtgtt  36060
cttcctgtgt gccaagcatt attctgagtc atttacatgt gttacctcat gctacaaact  36120
ccacgtaatt ccagaaggat cccacagcag gggaataatc ttgatttgag ttccgccaga  36180
tgtaggctct tacaaaaggg aagaaaaact atagattaca tgttatcaag caagttacca  36240
ctatgggcaa ctagagctca gtcctgctgg gaaatgtgga gagactgtgt agaatgtgca  36300
cctgaattgt cccatcagag ggctgaggaa gctggggtat ttatttacca cctcccatca  36360
gttattggct gagaactgct tccaggtggc attaattccc cagcatttca gccctgcagg  36420
cagggcagat cttgtggtct gagaatgctc tctggtaaag gggagcaggt gctggttgaa  36480
gaaagtctgg ctagaactca tggaaaatag taagtgcaga agggacgtgg acaggtattg  36540
ccatcatttg ctctcaggac tttgatgtag gattcattta actgcccaaa tcctgaaaca  36600
aggtaggcaa gtacaggatt ccttacatat tgcttggcct ctatgctagg tgagggactt  36660
gcaatgaatg tttagaagaa acagtttgtc caatttgcct caattgtttc ccacaacaga  36720
cagcaggagc gaagaatgga ttgaccttgc agatggtttc ctgtcattat aaaaaggctt  36780
aatataccta ctgcttctgg gcagctcact aggtggccct ctcgagctgc gtcagagtcc  36840
tgtttaactt cggaagcaga tctaagacct gctgggcagg gtgtgcctag aaaatctggc  36900
ttggttggag tgtatgaccc aactgtgccc agagactcac tcacttcctc cagaagactt  36960
gtgtctgtct tgggaaaaac ttctggctga gatctttatg aaaaagctca gccttcctgg  37020
atactcagct gcaagctaca ggggacctca gactctctgt ttccaggatg actcttttca  37080
gatcttttct ggctgaggtt gccaggggtt acctgactaa ttctgcgttg atctctctct  37140
ctctctctgg tggactctga cctcctgacc tgggctatac ccaagggtag gaagatgaga  37200
tgccagacac tttggtcttt gatccagaat gttctccata tcattgtttt tttttttctt  37260
```

```
taaacaatct ttatcctttt gcctccataa aagtaagcca tttcccatcc cagtgctgaa  37320
gaaactggca aaggtccctt tcttatgtgc ctccccagtg ctacctccaa atgccaatac  37380
cttttatttg gaaaatatta ctatagagac ttggtcatag gacctgattc atttgtataa  37440
tagaagaggt gtatccaatt atccgtttcc attatttgat ataaagtcat tgtagatgta  37500
ctctgacaga agggaaattc ttgccaaata tgataacttt gcccttaaac acagcagtca  37560
caaatgaata aatgccaacc atttatacat ttccacactt acaactcaat tttccaatgg  37620
agctgttgat gaacctaatc tcgagataac ttcgtataat gtatgctata cgaagttata  37680
tgcatgccag tagcagcacc cacgtccacc ttctgtctag taatgtccaa cacctccctc  37740
agtccaaaca ctgctctgca tccatgtggc tcccatttat acctgaagca cttgatgggg  37800
cctcaatgtt ttactagagc ccaccccccct gcaactctga gaccctctgg atttgtctgt  37860
cagtgcctca ctggggcgtt ggataatttc ttaaaaggtc aagttccctc agcagcattc  37920
tctgagcagt ctgaagatgt gtgcttttca cagttcaaat ccatgtggct gtttcaccca  37980
cctgcctggc cttgggttat ctatcaggac ctagcctaga agcaggtgtg tggcacttaa  38040
cacctaagct gagtgactaa ctgaacactc aagtggatgc catctttgtc acttcttgac  38100
tgtgacacaa gcaactcctg atgccaaagc cctgcccacc cctctcatgc ccatatttgg  38160
acatggtaca ggtcctcact ggccatggtc tgtgaggtcc tggtcctctt tgacttcata  38220
attcctaggg gccactagta tctataagag gaagagggtg ctggctccca ggccacagcc  38280
cacaaaattc cacctgctca caggttggct ggctcgaccc aggtggtgtc ccctgctctg  38340
agccagctcc cggccaagcc agcaccatgg gaacccccaa gaagaagagg aaggtgcgta  38400
ccgatttaaa ttccaattta ctgaccgtac accaaaattt gcctgcatta ccggtcgatg  38460
caacgagtga tgaggttcgc aagaacctga tggacatgtt cagggatcgc caggcgtttt  38520
ctgagcatac ctggaaaatg cttctgtccg tttgccggtc gtgggcggca tggtgcaagt  38580
tgaataaccg gaaatggttt cccgcagaac ctgaagatgt tcgcgattat cttctatatc  38640
ttcaggcgcg cggtctggca gtaaaaacta tccagcaaca tttgggccag ctaaacatgc  38700
ttcatcgtcg gtccgggctg ccacgaccaa gtgacagcaa tgctgtttca ctggttatgc  38760
ggcggatccg aaaagaaaac gttgatgccg gtgaacgtgc aaaacaggta aatataaaat  38820
ttttaagtgt ataatgatgt taaactactg attctaattg tttgtgtatt ttaggctcta  38880
gcgttcgaac gcactgattt cgaccaggtt cgttcactca tggaaaatag cgatcgctgc  38940
caggatatac gtaatctggc atttctgggg attgcttata acaccctgtt acgtatagcc  39000
gaaattgcca ggatcagggt taaagatatc tcacgtactg acggtgggag aatgttaatc  39060
catattggca gaacgaaaac gctggttagc accgcaggtg tagagaaggc acttagcctg  39120
ggggtaacta aactggtcga gcgatggatt tccgtctctg gtgtagctga tgatccgaat  39180
aactacctgt tttgccgggt cagaaaaaat ggtgttgccg cgccatctgc caccagccag  39240
ctatcaactc gcgccctgga agggattttt gaagcaactc atcgattgat ttacggcgct  39300
aaggatgact ctggtcagag atacctggcc tggtctggac acagtgcccg tgtcggagcc  39360
gcgcgagata tggcccgcgc tggagtttca ataccggaga tcatgcaagc tggtggctgg  39420
accaatgtaa atattgtcat gaactatatc cgtaacctgg atagtgaaac aggggcaatg  39480
gtgcgcctgc tggaagatgg cgattaggcg gccggccgct aatcagccat accacatttg  39540
tagaggtttt acttgcttta aaaaacctcc cacacctccc cctgaacctg aaacataaaa  39600
tgaatgcaat tgttgttgtt aacttgttta ttgcagctta taatggttac aaataaagca  39660
```

```
atagcatcac aaatttcaca aataaagcat ttttttcact gcattctagt tgtggtttgt  39720
ccaaactcat caatgtatct tatcatgtct ggatcccccg gctagagttt aaacactaga  39780
actagtggat cccccgggat catggcctcc gcgccgggtt ttggcgcctc ccgcgggcgc  39840
ccccctcctc acggcgagcg ctgccacgtc agacgaaggg cgcagcgagc gtcctgatcc  39900
ttccgcccgg acgctcagga cagcggcccg ctgctcataa gactcggcct tagaacccca  39960
gtatcagcag aaggacattt taggacggga cttgggtgac tctagggcac tggttttctt  40020
tccagagagc ggaacaggcg aggaaaagta gtcccttctc ggcgattctg cggagggatc  40080
tccgtggggc ggtgaacgcc gatgattata taaggacgcg ccgggtgtgg cacagctagt  40140
tccgtcgcag ccgggatttg ggtcgcggtt cttgtttgtg gatcgctgtg atcgtcactt  40200
ggtgagtagc gggctgctgg gctggccggg gctttcgtgg ccgccgggcc gctcggtggg  40260
acggaagcgt gtggagagac cgccaagggc tgtagtctgg gtccgcgagc aaggttgccc  40320
tgaactgggg gttgggggga gcgcagcaaa atggcggctg ttcccgagtc ttgaatggaa  40380
gacgcttgtg aggcgggctg tgaggtcgtt gaaacaaggt ggggggcatg gtgggcggca  40440
agaacccaag gtcttgaggc cttcgctaat gcgggaaagc tcttattcgg gtgagatggg  40500
ctggggcacc atctggggac cctgacgtga agtttgtcac tgactggaga actcggtttg  40560
tcgtctgttg cgggggcggc agttatggcg gtgccgttgg gcagtgcacc cgtacctttg  40620
ggagcgcgcg ccctcgtcgt gtcgtgacgt cacccgttct gttggcttat aatgcagggt  40680
ggggccacct gccggtaggt gtgcggtagg cttttctccg tcgcaggacg cagggttcgg  40740
gcctagggta ggctctcctg aatcgacagg cgccggacct ctggtgaggg gagggataag  40800
tgaggcgtca gtttctttgg tcggttttat gtacctatct tcttaagtag ctgaagctcc  40860
ggttttgaac tatgcgctcg gggttggcga gtgtgttttg tgaagttttt taggcacctt  40920
ttgaaatgta atcatttggg tcaatatgta attttcagtg ttagactagt aaattgtccg  40980
ctaaattctg gccgtttttg gctttttgt tagacgtgtt gacaattaat catcggcata  41040
gtatatcggc atagtataat acgacaaggt gaggaactaa accatgggat cggccattga  41100
acaagatgga ttgcacgcag gttctccggc cgcttgggtg gagaggctat tcggctatga  41160
ctgggcacaa cagacaatcg gctgctctga tgccgccgtg ttccggctgt cagcgcaggg  41220
gcgcccggtt ctttttgtca agaccgacct gtccggtgcc ctgaatgaac tgcaggacga  41280
ggcagcgcgg ctatcgtggc tggccacgac gggcgttcct tgcgcagctg tgctcgacgt  41340
tgtcactgaa gcgggaaggg actggctgct attgggcgaa gtgccggggc aggatctcct  41400
gtcatctcac cttgctcctg ccgagaaagt atccatcatg gctgatgcaa tgcggcggct  41460
gcatacgctt gatccggcta cctgcccatt cgaccaccaa gcgaaacatc gcatcgagcg  41520
agcacgtact cggatggaag ccggtcttgt cgatcaggat gatctggacg aagagcatca  41580
ggggctcgcg ccagccgaac tgttcgccag gctcaaggcg cgcatgcccg acggcgatga  41640
tctcgtcgtg acccatggcg atgcctgctt gccgaatatc atggtggaaa atggccgctt  41700
ttctggattc atcgactgtg gccggctggg tgtggcggac cgctatcagg acatagcgtt  41760
ggctacccgt gatattgctg aagagcttgg cggcgaatgg gctgaccgct tcctcgtgct  41820
ttacggtatc gccgctcccg attcgcagcg catcgccttc tatcgccttc ttgacgagtt  41880
cttctgaggg gatccgctgt aagtctgcag aaattgatga tctattaaac aataaagatg  41940
tccactaaaa tggaagtttt tcctgtcata ctttgttaag aagggtgaga acagagtacc  42000
```

```
tacattttga atggaaggat tggagctacg ggggtggggg tggggtggga ttagataaat  42060
gcctgctctt tactgaaggc tctttactat tgctttatga taatgtttca tagttggata  42120
tcataattta aacaagcaaa accaaattaa gggccagctc attcctccca ctcatgatct  42180
atagatctat agatctctcg tgggatcatt gtttttctct tgattcccac tttgtggttc  42240
taagtactgt ggtttccaaa tgtgtcagtt tcatagcctg aagaacgaga tcagcagcct  42300
ctgttccaca tacacttcat tctcagtatt gttttgccaa gttctaattc catcagacct  42360
cgacctgcag cccctagata acttcgtata atgtatgcta tacgaagtta tgctaggtaa  42420
ctataacggt cctaaggtag cgagctagcc taggttgcaa ggcatgaaag atgcataatt  42480
gtcaaagact tatatcttta attagaccta tttactttgc tcttatgatt ttaggtgtat  42540
attccttttt tttttttttg aaacagagtc ttgctctgtc acctaggcta gagggcagtg  42600
gcacaatctc ggctcactgc aacctctgcc tcccgggttc aagcgattct cctgcctcag  42660
cctcccaagt agctgggact acagacatgc gccaccatgc ctggctaggt gtatattctt  42720
atgataagct ctattatatc ctttcaggaa caatgatata aacagtaaat aactacacac  42780
aattttattt tgtctaagtg tccccttttgc tgtttttttgc ttttgcaaat aggatgtccc  42840
ggagccgtat caatgatgct ttccgtctga atgacaacag cctagagttt ctggggatac  42900
agccaacact tggacctcct aaccagcccc ctgtttccat atggctgatt atttttggtg  42960
ttgtgatggc actggtagtg gttggcatca tcatcctgat tgtcactggg atcaaaggtc  43020
gaaagaagtg agtatccttt cctagattta tctgtctttt tagaatgcat gaattggaaa  43080
ttttgcaaca aataacactg tatccacaca ggataattac ttacttggac atttatctcc  43140
ctaaatattc tgatatatcc catagaatct tgtcagatgc tagcagtacc ttaccttact  43200
agcaagctca catattatag atgtctagcc tgaggtttat tgggatgctg tagtcaagtg  43260
catcctatcc acagtggcat agccagactg caaactcagt aaggcattgt tctcactcat  43320
gactcttgct tcatccacag agactgacat ggagcacaaa gtgtaatgtc atctaagaat  43380
gaggtgcttc aaactactac tctttagtta ctttcattcc tccttgggaa actcaaattt  43440
atcatttgag ttcatgggca ggcacccttt aatttgttct agagctgagt tgattgaggg  43500
ctttaatcac cagggactga cttctagctc ctgtcttgag aaagtattaa ctcttgttgg  43560
tctgttcaaa taacttagta ttttgtatca ctctgacaac attatctgca tgttttcagt  43620
tgtttaaaca tactctcagt tgaatcttta cacaaattag tttattttat ttaattttct  43680
ttactataga gatctctcga ttctaccaaa taacttcatt tgaaaaagca aggctgtgga  43740
gatgggtaaa atcacctgcc ccacaagcat gaggacctga ctttgaatcc ccagagccca  43800
tatataaagc agatacagga ggcaagcatc tataatccca gcactcctcc agggagatgg  43860
aaggcagagg caggaaagtc cccagaagtc tgtaggccac tcagcctggt gtacacagca  43920
gaggcaacag accccatctc aatcacaatg ggtgttgaga atcaacactg gatattgctg  43980
tctgatcccc acgtgtgcaa tgtagcatac acacttacac acatgcacat gtgtacgcat  44040
acacagatgt gcacaaagca ctttctaggt agtgcagtca acatggttac aatgttcaaa  44100
aatacaaggg ggtcatagag ttccgttacc attctttgtt tctgagtttc cttttaacca  44160
aagttatcag tttttagtaa aatgaactat gcactacata ttcttattta ccaactagta  44220
tgttttagag gtatttccag atttttcaaa aaattcccaa gcaatatatt ttagagattc  44280
tttcagattg gctatgtaaa gcacttccat ttgcctggta atgtagttgc ccactttgta  44340
gcaaatgggt actcccatgg ttaccaaatg tttgtgtcta tttaaaaaat acaacaattt  44400
```

caaataggca atttcctgtg catgctaaag taggtgcaag atatgtccca gcaggtaaaa 44460
ggctaggtta aaatcatcat gaattctaat tttaattaat acttctgaac tgttctcata 44520
ggggcagaat taatgtacaa acagcaccag cttatgaaag ctctcctttt ctccaactca 44580
gcatccttag cacagggtgc catcagactt tttgacagtt atcctttggg tcagtgtaag 44640
taagtgtctt tctaccatca ctttaataag gagactttgt tttatttgac aggaaaaatg 44700
aaacaaaaag agaagagaac ccttatgact cgatggacat tggaaaagga gaaagcaatg 44760
caggattcca aaacagtgat gatgctcaga cttcctttta gcaaagcact tgtcatcttc 44820
ctgtatgtaa atgctaactt catagtacac aaaatatgag agtatacaca tgtcattagc 44880
tatcaaaact atgatctgtt cagtaaacgt tgtccaaaga gcatcagact tgagtggaca 44940
tcttcactga cattgctttc agtatttatt tctgcctaag gatttgacat ctcttctgtt 45000
tattaataga gatgtttatc ttagcataaa agagggaaat gtgcctttgg cctcacagtc 45060
tatccagggt gatatggttg ggtaactgga gttagaagat gagatgatgt ctcttggggg 45120
caagtgttgg cttcggtgtg gcatctgggc tgtgaactgg tgggactgtt gaggttgaga 45180
atggtgctcg ctggtcactt gaatccaagt gtgacgtcat gctctgtggc ttctgccttc 45240
acacttctca cttcaagtac tgtaggaatt tgttcacagt aatacttgaa atggactgtc 45300
ccttctttgg aggtgcagtt caacggagaa agaagccaga catcaggtag agaccatgac 45360
cttttctctt ccaaacttga tcaacatctc tctaacaaga cacagctagc acaggaaact 45420
ccacgaaccc agagcatgcc tgtcagaaac tacttccatt attctcccat tgtggagtaa 45480
gggaaaattc cagatgaatg ctcgatctgt gagatgggtg cccagtctct gaaattgttt 45540
gtattttctc acagggtctg agcaatggtg aacacaaagc cgacctcaat aaatacttat 45600
tagatttaga cactcctct 45619

<210> SEQ ID NO 6
<211> LENGTH: 23
<212> TYPE: DNA
<213> ORGANISM: Artificial Sequence
<220> FEATURE:
<223> OTHER INFORMATION: 7878mTU Fwd

<400> SEQUENCE: 6
cccagatggc taaattcaat tga 23

<210> SEQ ID NO 7
<211> LENGTH: 16
<212> TYPE: DNA
<213> ORGANISM: Artificial Sequence
<220> FEATURE:
<223> OTHER INFORMATION: 7878mTU Probe (MBG)

<400> SEQUENCE: 7
ttcatctgga aaattg 16

<210> SEQ ID NO 8
<211> LENGTH: 24
<212> TYPE: DNA
<213> ORGANISM: Artificial Sequence
<220> FEATURE:
<223> OTHER INFORMATION: 7878mTU Rev

<400> SEQUENCE: 8
ggaatctggg caaataattc attc 24

<210> SEQ ID NO 9
<211> LENGTH: 19
<212> TYPE: DNA
<213> ORGANISM: Artificial Sequence
<220> FEATURE:
<223> OTHER INFORMATION: 7878mTD Fwd

<400> SEQUENCE: 9
gggccgcatc aatgatgtc 19

<210> SEQ ID NO 10
<211> LENGTH: 24
<212> TYPE: DNA
<213> ORGANISM: Artificial Sequence
<220> FEATURE:
<223> OTHER INFORMATION: 7878mTD Probe (BHQ)

<400> SEQUENCE: 10
tggcctgaat gataacagcc tgga 24

<210> SEQ ID NO 11
<211> LENGTH: 23
<212> TYPE: DNA
<213> ORGANISM: Artificial Sequence
<220> FEATURE:
<223> OTHER INFORMATION: 7878mTD Rev

<400> SEQUENCE: 11
gtggctcaag tgttgggtga atc 23

<210> SEQ ID NO 12
<211> LENGTH: 20
<212> TYPE: DNA
<213> ORGANISM: Artificial Sequence
<220> FEATURE:
<223> OTHER INFORMATION: 7878hTU Fwd

<400> SEQUENCE: 12
gtgaggctgg acttgggaat 20

<210> SEQ ID NO 13
<211> LENGTH: 26
<212> TYPE: DNA
<213> ORGANISM: Artificial Sequence
<220> FEATURE:
<223> OTHER INFORMATION: 7878hTU Probe BHQ

<400> SEQUENCE: 13
cctttcctct ttgtcacaga cctcca 26

<210> SEQ ID NO 14
<211> LENGTH: 19
<212> TYPE: DNA
<213> ORGANISM: Artificial Sequence
<220> FEATURE:
<223> OTHER INFORMATION: 7878hTU Rev

<400> SEQUENCE: 14
ggagggctct gcctggatt 19

<210> SEQ ID NO 15
<211> LENGTH: 23
<212> TYPE: DNA
<213> ORGANISM: Artificial Sequence
<220> FEATURE:
<223> OTHER INFORMATION: 7878hTD Fwd

<400> SEQUENCE: 15
gcaaaggtcc ctttcttatg tgc 23

<210> SEQ ID NO 16
<211> LENGTH: 23
<212> TYPE: DNA
<213> ORGANISM: Artificial Sequence
<220> FEATURE:
<223> OTHER INFORMATION: 7878hTD Probe (BHQ)

<400> SEQUENCE: 16
cccagtgcta cctccaaatg cca 23

<210> SEQ ID NO 17
<211> LENGTH: 23
<212> TYPE: DNA
<213> ORGANISM: Artificial Sequence
<220> FEATURE:
<223> OTHER INFORMATION: 7878hTD Rev

<400> SEQUENCE: 17
caggtcctat gaccaagtct cta 23

<210> SEQ ID NO 18
<211> LENGTH: 120
<212> TYPE: DNA
<213> ORGANISM: Artificial Sequence
<220> FEATURE:
<223> OTHER INFORMATION: 7878 5'mouse/5'human

<400> SEQUENCE: 18
aagatgtcca gctcctcctg gctccttctc agccttgttg ctgttactac tgctcagtcc 60
accattgagg aacaggccaa gacatttttg gacaagttta accacgaagc cgaagacctg 120

<210> SEQ ID NO 19
<211> LENGTH: 160
<212> TYPE: DNA
<213> ORGANISM: Artificial Sequence
<220> FEATURE:
<223> OTHER INFORMATION: 7878 human//xho//loxP

<400> SEQUENCE: 19
catttataca tttccacact tacaactcaa ttttccaatg gagctgttga tgaacctaat 60
ctcgagataa cttcgtataa tgtatgctat acgaagttat atgcatgcca gtagcagcac 120
ccacgtccac cttctgtcta gtaatgtcca acacctccct 160

<210> SEQ ID NO 20
<211> LENGTH: 192
<212> TYPE: DNA
<213> ORGANISM: Artificial Sequence
<220> FEATURE:
<223> OTHER INFORMATION: 7878 (loxP)/ICEUI//NheI//human

<400> SEQUENCE: 20
cattctcagt attgttttgc caagttctaa ttccatcaga cctcgacctg cagcccctag 60
ataacttcgt ataatgtatg ctatacgaag ttatgctagg taactataac ggtcctaagg 120
tagcgagcta gcctaggttg caaggcatga aagatgcata attgtcaaag acttatatct 180
ttaattagac ct 192

<210> SEQ ID NO 21

<211> LENGTH: 120
<212> TYPE: DNA
<213> ORGANISM: Artificial Sequence
<220> FEATURE:
<223> OTHER INFORMATION: 7878 3'mouse/3'human

<400> SEQUENCE: 21
agcctagagt ttctggggat acagccaaca cttggacctc ctaaccagcc ccctgtttcc 60
atatggctga ttatttttgg tgttgtgatg gcactggtag tggttggcat catcatcctg 120

<210> SEQ ID NO 22
<211> LENGTH: 40887
<212> TYPE: DNA
<213> ORGANISM: Artificial Sequence
<220> FEATURE:
<223> OTHER INFORMATION: 7679 allele
<220> FEATURE:
<221> NAME/KEY: misc_feature
<222> LOCATION: (1)..(1377)
<223> OTHER INFORMATION: Mouse sequence
<220> FEATURE:
<221> NAME/KEY: misc_feature
<222> LOCATION: (1378)..(37630)
<223> OTHER INFORMATION: Human sequence
<220> FEATURE:
<221> NAME/KEY: misc_feature
<222> LOCATION: (37631)..(37636)
<223> OTHER INFORMATION: XhoI
<220> FEATURE:
<221> NAME/KEY: misc_feature
<222> LOCATION: (37637)..(37670)
<223> OTHER INFORMATION: LoxP
<220> FEATURE:
<221> NAME/KEY: misc_feature
<222> LOCATION: (37677)..(37702)
<223> OTHER INFORMATION: Iceu1
<220> FEATURE:
<221> NAME/KEY: misc_feature
<222> LOCATION: (37703)..(37708)
<223> OTHER INFORMATION: NheI
<220> FEATURE:
<221> NAME/KEY: misc_feature
<222> LOCATION: (37709)..(38198)
<223> OTHER INFORMATION: Human sequence
<220> FEATURE:
<221> NAME/KEY: misc_feature
<222> LOCATION: (38199)..(40878)
<223> OTHER INFORMATION: Mouse Sequence

<400> SEQUENCE: 22
aggcccatga gccctgccat ttaaagtggc tcctctctta cactctggga atgaggacac 60
ggagccagct gctgaacttc accaggataa ccattaaaat tgctttggag ttcatatttc 120
cacgatccca tgcctatgga tgccaaggac ttgtcatgga tgcgctttgg atttcataat 180
gcagagtcat tattacttcc ttgagttctc agctgagttg taagcaggta agtgaaaggg 240
aaagaggcac ctgataaagt cagctgtagg actagagttt agcatgtctc ctgagaaata 300
gaaaatgact gcttgaaact ttaccaaagc cacacaggaa gcatcaaact ccctatggag 360
tggagaagag tcttataatt ttttaaatgg gcagagaaat gaatttattt ttaattttta 420
gagacagggt ttctttgtat agctctagct gtctttgatt ggtagacaaa gctgtcctca 480
aactcagaga tcttccttcc tttgtctcct gagtgctggg attaaaggca tggaccacca 540
ctgccctgcc ccattctctc cattaatttt aagtgaatgc ttgcaaaagc tcacttcttt 600
ggtgaacagc ttcctttaca aataagtacc tttgccttcg tttttatagg attcttaaaa 660
agaaaaaaaa gattcagcca ggtggttgtg gtgcacacct ttaatcccag cagtcaggag 720
gcagaggaaa gcagatctct tgagtttgag gctagcctag tctacagagg gagttccagg 780

-continued

```
acagccaagg ctacagagag gaactgtcta aaaacaccaa gaaagagaga aaggagagag    840
ggagaggatg gatagcttat tgatagaatt gtcagaaaag gctataagtt ccaatatgtg    900
tcccatgatt tctaagtcta gccctttctg ttatagtaaa atcatagtac accctcctcc    960
tccagtgtat ctttaacagc ttttaaggaa catattaact aaatgtccag gttttgattt   1020
ggccataaaa tgttagcaaa gctaaggttt tctaggatta atgaataaca tgtctttatt   1080
tagtttactt aaaaaaatca ttctaaaata tctgtttaca tatctgtcct ctccaggatt   1140
aacttcatat tggtccagca gcttgtttac tgttctcttc tgtttcttct tctgcttttt   1200
ttttcttctc ttctcagtgc ccaacccaag ttcaaaggct gatgagagag aaaaactcat   1260
gaagagattt tactctaggg aaagttgctc agtggatggg atcttggcgc acggggaaag   1320
atgtccagct cctcctggct ccttctcagc cttgttgctg ttactactgc tcagtccacc   1380
attgaggaac aggccaagac atttttggac aagtttaacc acgaagccga agacctgttc   1440
tatcaaagtt cacttgcttc ttggaattat aacaccaata ttactgaaga gaatgtccaa   1500
aacatggtga gttctcatgg ctctattggg ctatttgttg cctcttaaag attagattac   1560
tgcccgtgaa actgaaaagg gaaatcaaaa aaaatgctct gagttgtgag attggatgtt   1620
tgcctccata tccctgattt tggcgtcgac gataactaaa cttaattgac cctggggttc   1680
attcagaaaa ttgttacaaa ataattcact ggtctcaatc cagatgcttg gaaacaagag   1740
aatattcttt ataaagttac caccataatt ctcatcacag tcaggatttc aaagcatttc   1800
atggaaatgc cataagttat tgagttaata atttccttta gcctacaata tcaataggaa   1860
tatctaaaga ttctctacaa atgatatatt aactgaaaaa tgcaactgga ggcttagtga   1920
aagaactagt aattaagcta atcagggctt gggtgaggct ggacttggga attcctttcc   1980
tctttgtcac agacctccaa gggactccaa aaggtcacag aatccaggca gagccctcca   2040
aaacaaaaac aaaaacaaac aacaaaaaaa ctatgattaa accagttctg acaaatatca   2100
gaatgctctg ggaaagccag atgctttaac aagtgcaagg atttaggaat ttcttctctc   2160
acagatccca aaacagtatc cttaagtggt gatccttatg tcaagctgtg agaatatacc   2220
tcaaaataat agaaggcatc caaacttgat cagtatagtg tcataaagct gctgatgtag   2280
aagtgtggag aggtccatca gatagagata tggaaaaaaa agcttggtta aaacaggttt   2340
ccaaagttct ctccctttct ctgccattgt ggtatgtgtg gttgaccatt tctcatcatg   2400
ttttcttaca agactttcag gatcaagcaa ttcctcgcca aaaaacaaaa tcaaggacac   2460
gttgtagcta tttcttggtg agttaccaga agctgtgaag agagagcatg aggcccatac   2520
tttttttttt ttttgaaggg tctcgctctg ttgcccaggc tggaatggag tggcatgatc   2580
atgattcatt gcagcttgac ctcctgggct caaatgattc tctcgcatca tttaacattt   2640
ttttttgtag agatgagatc tcactttgtc tcccaggctg gtcttgaact cctgggctca   2700
agtgatcctc ttgcctcagg ctcccaaagt gctgggatga caggcatgag ccactgcacc   2760
tagcctacca cacttactct ttgcgtggtc tctagagctt cttcagcccc cctgctgcca   2820
gggtccctag ggtcttgggc atgccccatt tctgaaccta ttcctgtctc cagggataga   2880
gtcacagtga actcagacca gggtaattct aaactgctat tctgtatata cccaaggaaa   2940
tttcatccct gtctctaatg agtctgtccc atgcccctta atacacatga acacctacac   3000
acaggtacaa gtcggggaag atcactgtgc agcacataaa ataaaattca ggggcgagca   3060
cttttttttcc catgagataa agttaggaaa aaataaaaat gttcatacag attaaaaatt   3120
```

```
ttaaatgtta aaatattaaa cccccaatct aaaataaaga aaaaataatt tcttaaatcc   3180
taagcttgag ttatggaatt cacattctta taatttacat tacctatttt gttaaatgga   3240
agactttttt ttttaatatg caagtacctg ggcatattta gaaagtaacc aaggcagctt   3300
ttgtctttga acctgatgcg gttttgacag ctctatctgg aaattgagcc agcatatggg   3360
agccaagggt gaaagttttc ctgggagatt tgggctccaa ggtactggat agatgctaaa   3420
gattccattc agtttttcat tttctgtctt catggaactc tcacacctac aggggaagaa   3480
atggtttaga ggttactaaa agtatatagc ctggtttagg tgatagtgag ctatagaaaa   3540
agagaaaata agttgtcagt actttaaatc tcaaacaact tcttacaaaa ggattttaat   3600
agtttaaata caattatcac aagttgggta aagacaacca gacctatggc ctgataaatc   3660
atgtatttaa tttatgcata tagttagggc caaaaagagc agagtatctt tttgaatgtt   3720
ttaaaatata atctaggatt ttatgcctac agtccttgaa attacaaagg atctctctca   3780
agttgggaat atgctatcca ttgcagttac ggatgggatt tagagactgt tttaatttct   3840
tgtgattatc tcaaacaacg tgttccttac tcccaaaact cccttgtatg gctacagaaa   3900
ctgttgcagt tttagttgct tctcccctgc ctttgcccag aggtagtgtg gaatgccacc   3960
aattttatct gtaatggttc ctttcaagcc tggggctatg taagctgcta tatatgcttc   4020
attccattca tcattcagtc taaatatagc tatcaaccac taaattatct gataggtatg   4080
catgaactga ctgattcttt gcataactac taagctatct gttttattta ggcttgggag   4140
ccctagggta aggatacgga ataaattgta aatgatatta aaagaatagc ttggcaagga   4200
ataatacctc ctcaggggcc aaaatgcaag gcaacacaaa gtgatttttt tggtgatata   4260
attataacac atgtagtatg gtagtgataa ctaaaataaa attggatagc ctcaaaattc   4320
ctacatgtag tatgataaac aatgttctaa gactgaggcc tttgggaggt agtgagttat   4380
ttcctataga tagagagtaa aattattcct ataatttggt atgaaagttt taccagaaat   4440
tttgcttcac agtaaatcat ctggattggg tgaagccagg tagggattga gaagtgagtc   4500
aggtgggttg catagatgag tttgtgctgc agaccaaact cctcttccca tagctcactt   4560
cttcccactc ctgcatgtta gagagaagac tagaatgtgt caaatacaac ctataggata   4620
atagttcaga gcattagctt cggaagtaaa cactaggttg atgccctggt tcttctaatt   4680
tctagctgtg tgacctaggg aaagttacct gctgtgtgcc tcatttccct tatttgtaaa   4740
gttgagacaa taacaactcc ctcacaaggt tgttgtgaag attaatgaaa aagcagtttc   4800
tgagaggttg tgagtgttca gtaaagaaag aaattgcttt cctttttttt ttttttgag    4860
acagattctc attctgtcat tcaggctgga gtgcagtggc gcgatcatgg ctcactgcgc   4920
ctcgacttcc ccaagctcag gcaatcttcc cacctcagcc tcctgagtag ctgggactac   4980
aggtgcgagc caccacacct ggctagtttt tgtattattt gcagagatgg ggtctcgcct   5040
tgttgcccag gcttgtctca aacttctggg ctcaagcgat cttcccacct caacctccca   5100
aagtgctggg attacaggca tgaaccacta cacacagcct attttccatt ttcactgcca   5160
ttattttctc tgtctcttgt gtggctcatt actgccactt ctgtgcacca tttccatcat   5220
gtcacatgcg tagtcaaaac cctcagtgac tgcctaattc tcagagggta aaagtgaaat   5280
tccttggcct ggaaagtgca atcatgcctg aagttctacc tgtgggagct gtactagtta   5340
tctattgtgt aaaaagttac cacaagctta gcagattaaa acaacacata tttaatatcc   5400
cacagtatct gtgggctagg agtccaggca cagttcagct ggatcttctg cttctaagtc   5460
tcatatggtt gcattcaagg tgctggctag agctatggtc tcttctgagg cttgactggg   5520
```

```
gatggatata cttccaagcc aatgcaatta ctcagaggcc gtctttaatt atttgccatg   5580
tggccttttc catagggtag ctcacaacgt ggcatcttgc tgcaacaagt cagcaaagga   5640
gagagtcttc tatcaagatt aaagttaaaa tcttatgtaa cgtaaacatg acatcctgtc   5700
acctgtgttg tatgctattg gttgaaagta aatcacgggt ctgctcatac ttatggggag   5760
gggatcacac aagggtgtga ccaccaaagg cagagatcat gggagcattc ttagagtctg   5820
tctgccacag ggccaggatc aaatgctggt ggctgattgc cagctccact gtttatttct   5880
ctcagccgct ttctgtatgt acaaaaaagg agagagagtg attttctacc tcatagtgtt   5940
gttaagaaaa tcaaatgagg taaattattt tgcaaagtat tctctactca tctgactcct   6000
acctactttc aggtctgtct taagttgcaa cttctgcatg agggcttggc caagtatggt   6060
cacctgcatg aatttcctct ttcttgtaac agaaactgct tggcccactc ataatttata   6120
cattattata tactcttatg tttcattaat gaaacattta taatgcatat cttatctgtc   6180
tgataaaatg gaaagcaatc taaggacaat gacttttccc ctatacataa caaaatataa   6240
aataaatcat aacataataa ataataaata aataataaaa taactaacat ttgttgaatg   6300
attaggatgt gttaggcact cttgtaagca tttcattttt ttgttacttc ttcaaatcct   6360
tacaacagtc cttggaggta agtcctatta ttactttcat tttgcagata agacaactgt   6420
ggctcagaga ggctaaggta cttgagtcca ggagcagaat tcttactttc ctcaaacgtt   6480
atctcttttg tgtggtctag ggcagtacaa tataccaagt agttgctcat tttggtcttt   6540
ggtaaatgga aatgaatttg taagttgaga aaagactaca ctacagtagt ttggagaagt   6600
ccactttcca actgatgttc aagattcagg aggggggaa atgtgtcctg gcatcatcac   6660
ttgcttgatg atttcttttg ctggtagaaa atcaccatgg ctaccaatgg ccattttctg   6720
ggaagccttt tttgggaatc ctaacttaag atcaaaatcc ctgggctaag tcacggcagc   6780
taggaggtta ctgtgaaccg gttctcattt cttatggttt ccattgttat tagggggctg   6840
tattctcatt aagtccactc tgagctctac tggattctct ttttagagca ctcgtctttg   6900
aattcttggc caactcatct atgtcacagc actaaggcta taaattccag ggccccacaa   6960
tgtggattat ctgtgagaat tcatttccag ttctggggac aagacccttg ggaaaaccag   7020
gcaataggcc agagagagac agagagagag agagtggtca aaagtggcct ggtcactctt   7080
aacctaaacc ttgaccttca gcggagtaga ggactaaatc actcaggaaa tattaaatgt   7140
ttcaccagat attatttgga ctatatcttc tgttctatct cttcaagcaa tgccattcca   7200
acttcaattt tcttttctgt catttcagaa taatgctggg gacaaatggt ctgccttttt   7260
aaaggaacag tccacacttg cccaaatgta tccactacaa gaaattcaga atctcacagt   7320
caagcttcag ctgcaggctc ttcagcaaaa tgggtcttca gtgctctcag aagacaagag   7380
caaacgggta cgtttgtgaa cattttagca ttgatcccaa gagttgaaat atttgggaaa   7440
tattaaacat taatatcacc cacagcagct gcctttattt gaaaaaatag taatgctgat   7500
gttagaaaaa tctctctcta tgcctaggta aggtgtccat ataatttatt attcaaactg   7560
gaatctttga gagtgaaaga cactggtaat tattatattc aaacacagag ttaaactgag   7620
attgtccctg gcactgtggt gtgtatggac acccccctagt gttaggtcac cttcctgaag   7680
gatcaggcag cctgaagaat acagttagtt tatgtcagtg gttctcaact gggggtgatt   7740
tagccctccg ggatatttg acaatgtctg gagacgtttt tggttgccac aaatggggat   7800
actgttgaca tctagtgggt agggatgctg cagaacattt cacaatgcat gggatggccc   7860
```

```
ccaacaacaa agaatgatct tgtccacaat gtcaacagca aacttttttt tctgtaaagg   7920
aacagatgac agtaaatatt ttaggttttg tgtatttagg tattgtctgt gttgcaacta   7980
gtcaactgtg ctgttgtatc aggaaatcag ctgtagctaa tatataaatg aacaagtatg   8040
gctgtgttca aataaaactt tacaaaaaca ggcagcagac aggatttggt ctgcagaaca   8100
cagtttgcag acctctgata tagcctattg aaatattttt aacctaaaat atttagctat   8160
ttaaaaagaa agtcttcttt ctcagttgct tgtcctctgg aactttgtat gttctaatct   8220
gtgaatataa aaataaaaat gcatcaaaaa ggcaaagata aaaccatgtg aaatgtatct   8280
ttctacaagt taacatttat ttttctgcat tctttgggtc caattatcca actaattatc   8340
aatgcacttt actttatcca ttctatgttt ctccattttt tcccccaaca aggacactat   8400
aagaaacctt gcccattcgc atatagacaa tctggtctag cctaggtgga acctagaaat   8460
tctatttttt aaaaaatccc cagataattc taatgtgtag ccaggactga aaaccactga   8520
aatgcatgta agagcttaaa gtgtttggga agaggaggga ctcaaggttg cttagatttg   8580
atggagagga agccgtggag attgaagaag agctggagag agaccatgag ggttttgtg   8640
ccatggtaag gaatttaggt ttgttccttt ggactatggg atcgtgtgga agttttaaac   8700
ataggatcta tttcatgttt taggatgact ctcaaggcag aaccaaaggg aaataggaga   8760
aggagaaaca gatcctttaa tccagtgctt cttaaatcaa tctgagggag agaaccattt   8820
ccttccttcc ttccttcctt tcttctcttc ttccttccct ccttctctcc tccctcccgt   8880
ctttcctttc tccctccttt attcctttat ttccaataca ttgcagatca atacttgctt   8940
aagttcattg attacatgct tagatgtcat ggaaatatca aattgttctc caaagtttat   9000
aaacttttat tctcttaatt cctgtactta tcacagaatg gaaacaaact gtcacttgca   9060
ctggtccacg gattacacct ggagtagcac tgcttcacta tatcaccttc actttatctg   9120
cagggtaaag tttaaaaact ttggtatggc atagacggtc cctcgtgatc tggcccctgc   9180
ttgtctctcc attctcatgt ctttcatttc ccctaatgaa caccattgct ccagtttcat   9240
tcaacatctc actgtcccct gagaatgcct tgtcttttcc aacctccttc catcttttag   9300
actcttccct ctacctccct tctctacatg accagtgcct acttcttctc caagacacag   9360
ctcttatctt cccttctctt tggacccatt cttgaatctc ctggttatta gttattaatt   9420
tctccctgct cctatactac cgcatcactt tttggtgaca gttatagcac ttgtcattct   9480
gttatgtatt aatagttatt gatttcatgg ctgcctcact gtcctatgac tttatggtct   9540
ttgacttgtt cacttcagaa ttgtcagagt gtaggacata ttccaggttc aataaatgct   9600
gaatgaaaca aaaaatgcac ctctctgtgt atgtgtggat aagaaaactt ctttgggttt   9660
tggtagatct ggttatttca attactccat atatatttat tatgtgctta tagtactttg   9720
tgctagtcga cagtggggaa acttaactgg gctattcctt ctccacatac agaaagatac   9780
atggcaaaga agtaaattgc tgtattttga gtaatcaaaa aatcatgtgg tcaaaaggat   9840
atctttatat tagcattctc ttcagcaaaa tttccattgt taacattgtt tattatcttt   9900
aatttgcagt tgaacacaat tctaaataca atgagcacca tctacagtac tggaaaagtt   9960
tgtaacccag ataatccaca agaatgctta ttacttgaac caggtaggct actaattttt  10020
agtagtgatt atgaaattta cttttctctc agattttaaa aatgattgca gatatgtgtg  10080
tttcaacaca tagatgctct tttaactttt agtaaaactt tcttgtaaat tgtatcacat  10140
ttacttaatt tgatcaagtc agtaagtaag tcatttcagt ggtttatttt ctctgcagac  10200
atattttgga actataaggg caaggacatg aatgaatcat gagattttat ttaaccactt  10260
```

```
tatgacctga tgtctgccaa ccttactttt aattctttaa agttcatgta gttctttaca  10320
aataaaattt ttacaaaggc atcttttctt gtctttgtgt gctttgggat aacaggtttg  10380
aatgaaataa tggcaaacag tttagactac aatgagaggc tctgggcttg ggaaagctgg  10440
agatctgagg tcggcaagca gctgaggcca ttatatgaag agtatgtggt cttgaaaaat  10500
gagatggcaa gagcaaatcg taagtttgct gatctgtaga ggtcctgaag ctctctgtgt  10560
ggccacgggg ctatttcttc tgcattacca agcctgccct ttgatatcag ggatacccct  10620
caattaacaa tcatgtcctc aacaattcag attacctgtt ttcaaaagaa attactgggg  10680
aaaaagaaaa ggtgcactgg cattctacaa ttcaagaagc tcaagaatga gactcaacta  10740
caaggcctaa agtaaattat ccaggaatta tgaattataa gtaatctagg aagatctcag  10800
gcccctaaaa gttcccgagg gagtctgggg attaaggggg ggaatcccat ttctcaggat  10860
gaaagacaga gtcactgcct tttgtctaaa gcccccacag ttcactttca aaggtcattt  10920
gtgtgtctac cttagggtga taccccagaa agaaaaaaata tcagattagt ttaggctgga  10980
aatgtattat tttctgcagt tgtaattata tctcagatta tgtggtcata aaaaatctta  11040
acataggaag gaatttccat atctcttaac ttattctctt ccctgaatag tgagctgaag  11100
tcatggaatc atgattcaca ttttgctttg atgatttact gcccactgag gttgagtaag  11160
gaagaatttt tttcccgcat ttgttgtttt aacatttctt tcactgccac ttaaattcag  11220
tattcttaag ccttaggcaa gctggagaca atagcttatc accattttta aaacaatatc  11280
ctgcatgtcc tttcatccaa atatttattt ctctcctcat cttcctgatc attaattgcc  11340
aatgtgaatg taaaaataaa aattattaaa ttatgtttac aaactttatt agctaatatc  11400
ctaacacaag cttgtgtttt ctgatggtga gatactaaag gaagcacata gaaacatgct  11460
attgatacat ataatttgca aacaaacaca ggttcactgt ggcaaagtct aagatgagtt  11520
gggtctgatc taaaaataaa aggccatgaa caaaagaaga atttaaaaac ttagagatcc  11580
agtcacatat tttaaagcta aagatacaaa ctgatgtatc aagagagtac acacccaggg  11640
ttaagagact aggaatgtgc ttctttcgct taccagctgt gtgatcttgg acaagtgatt  11700
taaccactct aagcacaggt tgttggtggg aatataaact ggtgaagctg ttatggaaaa  11760
atagtatgag gattcctaaa taaattaaaa atagaattac cgtatgatcc agcaatccct  11820
cttctgggta tatacctaaa ttagatgaaa ttaccccttc ataaagatat ctacactgcc  11880
atgttcactg cagcattatt cgcaatagcc aagataggga aacaacctaa gtgtttgtca  11940
agggatgaat gaataaagaa accgtggtag gtatatggaa tgggatatta ttcagcctta  12000
aaaaagagga gatcctgtca tttgcctcaa catggataga cctggaggac attatgctaa  12060
gtgaaataat ccagacataa aaagaaaaat atggcatcat ctcactcaaa agtggattct  12120
acaaaaaaat caaatataca gagatagagt aatagtgatt accaggggtg aggtggagcg  12180
gggtgggata tggggagaag tgggttaaag gatacaaagt agcagatatg caggatgaac  12240
aagtctaaag atctaatgta caacataagg actgtagtta gtaataatgt tttgtattca  12300
ggatttttgc aaaatgagta gattttagct gctcttccat ggggggggata atgcttaact  12360
atgtgagatg atggatatgt taatttgttt tactatagta accattttat tatataagta  12420
tctcataaca tcatgttgta caccttaaat atacacaata aaatttattt aaaaataaac  12480
ataggctgtt actctgcaca gtgggagtta taataatgac aatcttgtat ggttcttgtg  12540
cttattaaat aaaataatac atttaaactc ctggcacaga gcaagtgctt aaacagagat  12600
```

-continued

```
tacttaatgt tattattcat ttgcatccct ttgagttgat gtttatcaca ataaaaatgt  12660
gataagcctt taaatttctt ttaacctccc agcaaggcta atctgtgtat tttgtgcttt  12720
ctctctttct ttcccttatg ttcttccctt tctctttaaa aaaaaaaaca aacagattat  12780
gaggactatg ggattattg gagaggagac tatgaagtaa atggggtaga tggctatgac  12840
tacagccgcg gccagttgat tgaagatgtg gaacatacct ttgaagaggt aagcaaggaa  12900
ctgtacacac aaacagttgt ggggcagtgt atgggaaaga gggacagtga ctaaaggcat  12960
tctggctcat tcttaacaca ttggtcagcc attcccaggc ctcataaagt tatggaatat  13020
tagagtttga aagattttag agaataatag gacagcccct acagatgatc agaattgcgc  13080
tgctttcctc cttctttcag tcactgacca ttaattacca atagaaagac tataagaatg  13140
aaatattata agaacaaatg gtcctttaga ttataagtag gaatgatctt cttgagctac  13200
ctggggctgg cactgtcttc ctgtgttagc agagctatgg actttgcttt cttcctcagg  13260
acaattgata ctattacttt gagtaagcta gtcttcatag ggaagagaga gttttgtgaa  13320
cagaaatgtc ccatggatgt ttttccttca ttttggcccc atgcctcccc tttacgtgaa  13380
ccttcaaact tctgatgtga gttaccttgt cacagccata gtttggcaga gctatcaaaa  13440
atggaagtaa gacaaacaac tccccaaaaa ggaaatggga agaagacttg aataagtaca  13500
tcatcaaaga aattacacaa atggcaaata ggcaaataaa aagttattag ggaaatgcaa  13560
attaaagcta tgatgaaaat ccactccaca cccaccagga tagctatgat taaaaagatg  13620
gacaatacca agtattgggg agaatgtgga gacactggag ccctcttaca gtgcaggaag  13680
aaatgtaaaa tggggcagtc actttggaaa acagtttggc gatttcttaa aaagttaaac  13740
acacacttac catgactctt aggtttctat atgaaataaa tgaaaacatg tgtccttatc  13800
catagaaaga catacacaaa tgttcatagc agcaatattc ataatagccc caaactggaa  13860
aacccagctg tccttcaact agtgaatgaa taaacagact ctgatatact caaagtagcc  13920
ggagatagga gtggaactga ctacaagaaa ccttttgtgg ttatagaaat attaaaaaac  13980
tagatagtgg tgatggtttc ccggtagttt taatttattg aaactcatgg aactacacac  14040
ttgaaaatgg gtggctttta tagtatgtaa attatacctc aatgtaaaaa caaaggaagt  14100
aggtaacaat cttaaaaatg aatatatatt ttttgcatct gcttttattt tgggacctgt  14160
gttctcccaa gtatgtttat tggtttatgc agtggagtta tcatcaagtt ctaggaagaa  14220
ggaatacttt taaattttcc agaaatttga gagaagaaga attataattt ggggaaattc  14280
tacttgttta aagaatctcc tatttctagt gttgtggaat ggaaattaga attggttact  14340
ctttgtctta aactttcttc ctgggctttt cagattaaac cattatatga acatcttcat  14400
gcctatgtga gggcaaagtt gatgaatgcc tatccttcct atatcagtcc aattggatgc  14460
ctccctgctc atttgcttgg taagaagccc catgaattct tcgtgtactt ggctctttgt  14520
tatttctaac aataaaattg cctttttgag tgagccttaa cataaaactt ttgaaaaatt  14580
ctgtaagtgg ttagtaacat tgtagaaatc gcattttgaa agcattttct tcaaccaaaa  14640
gtctatttta aacaattctc tattgtatta cttttttgt acataaagag ttattatttt  14700
ggctgcaatt caaatgataa aggggttatt taagataact agagaaagaa ttacaggctc  14760
aaatgagagt ggaaatgggg aaaataattt ttagtattca agttgattgg ctaagctctt  14820
aaggtggaat ttgagatttt agtatcatat tgtcagagct tggttggctg ggggtggtca  14880
ggggtaacag aaggttatag cttgagcgaa agcttcctaa gttcattcta gacttcacca  14940
attactcttg ctgaaaagtg cttggcttgg aatcgtataa gtgaagaatg aatgaaagtg  15000
```

```
accatcttcc cctctcccac cgcagcagct gaggccaaat aaaatataaa tatttgaaaa  15060
tttcatgcca tgcatatata gcatttctac tgtagtcaaa ctaagttgct ggaagctaat  15120
ctcctccaca gccatacctc gtgtctgtca gcaggagaga atgcggagaa aggacctgtg  15180
gaggctttta actctaaagt aatatggaaa tccttcctac aatgtcaatg gcaagcagta  15240
tttagtaatt cagtttctgc ttaaacctgt ctggtgtgat gggataattt cttcattcca  15300
atatagacta atttactgct acatggaacc aatgtaatac aattctacct tatgtggaac  15360
ttaagcaaca cccctctgat gccttccatt cattagccct atttccatgc tatgaggtta  15420
cccagaatgt caattcctat tctacaagat gaccttccag atattcataa agaaccatca  15480
tataagatat agcatagtac ctggtgcaat acattttagt gactattatt gttattgtca  15540
tgtttaccct attttctttt gtcaagttaa atatcttata cattatcaac cattccttaa  15600
aacctcactt ttctataatt gttctccttt caatgagctg tactttgtca atgtccctcc  15660
tcaattatca tgcttagaga tgaacagtta ctccagatga ggtttgacca acataaagaa  15720
agacatggta ccatgactac ctttgttcta gacactatac ttctattgat ttagctcaag  15780
ttcacattta tgctttagaa gccaggtcat actgtttgtt ggctcatttt tggtctttta  15840
catgtggact gtgctttagc ctgatgtcac atatatgttt ttatgatgga taggtttttc  15900
tttaaaattt aagcatagga cttcacatgt atcactacta aattttatgt tttaaaatat  15960
aagtttaggg agtactttta ttttttttcag agtctcgctc tgtcgcctag gctggagtgc  16020
agtggctgat ctcagctcac cgcaacctct gcctcctggg ttcaagcgat tctcctgctt  16080
cagcctcctg agtagctggg attacaggct caagccgcca tgcccagcta atttttgtat  16140
ttttagtaga gacagggctt caccatgttg gccaggctgg tctcgaactc ctgatctcaa  16200
gtgatctgcc tgcttcagct ctgcaaagtg ctgggattac aggagtactc ttcatgaagt  16260
ttgttgcccc attttttttgg caccaggatt ctggtcctgc tcttggattg actttttcta  16320
gatacatctt ctttttttatg gtccctggcc ttggaataca acttaacatt tgtttgagat  16380
gtttacaaag tcaccaagtt aagtacacga atataggaat aaaagtggaa tttagttacc  16440
agttagtaga agttcctgaa tgatgatctt atatgatctc ttttgaagcc aacactagga  16500
attactaaca gcttaatttg taatattttg taccatggat ggtagattat agaaatctct  16560
ttctaattta cagtgtcaat gatggtccat atatttaata aattatgtct acatttctgc  16620
tgtgttgtca tatactaaca gattcttttt taaatatagg tgatatgtgg ggtagatttt  16680
ggacaaatct gtactctttg acagttccct ttggacagaa accaaacata gatgttactg  16740
atgcaatggt ggaccaggta ggaaaaagag cccttaaaaa ctaaatctaa attctcaact  16800
tcatttattt ttatgtcatc cttctatttt tattttttatg tgaaaccatg taaataaaaa  16860
atttaagcta attgaaattt atttcttatg tagctatagt ttcatggaaa agcagtttac  16920
aatggcctca gataacttga attgcaggtg tagtattgat ctcattgaaa ggtatttgaa  16980
atggagatta cctgagtttt ccattaagcg gtaagatgta gaattgtcaa ctggttggta  17040
tcactcattc caaagtttgt cattgctaag taaccagcca gtaatctcta tggatagtaa  17100
aaacaagaat attatgaggg gatttttgca tatttaaaaa attattagtg ttaaaaatat  17160
tacaagaatc tttaaaacaa ttttaagtaa catctttatt actactttgg tttaattatt  17220
taaatgtgct aggttcctca aaacacaagt aagtacatag cccatggacc caataaagca  17280
actacacaat cgagactaca aagcaaccag ctaacaacag catgacagga acgcttcacc  17340
```

-continued

```
taacagacag agagtggcaa attggagaga aaaacaaaac ctaaccttct actgtcttcg  17400
agattcatct cacgtgtaat gacacccatg ggctcaaagt aaagtgatgc agaaagatct  17460
atcatgcaaa tagaaaacaa aaaagagcag ggggctgcta ttcttgtatc agataaaaca  17520
gactttaaac caacaacagt aaaaaaggac aaagagggtc attacataat gataaagggt  17580
tcaatttaac aagaagactt aattatccta aatatatatg cacccaacat tggagtatcc  17640
agattcataa acatagcact tttagaccta ggaaaagact tagacatcca gaaaataata  17700
gtgggggact tcatcacccc actgacagtg ttatacagat cattgaggca gaaaactaac  17760
aaagaaattc tggaaattct ggacttaaac ttgacacttg accaattgaa cctaagagac  17820
atctatagaa tattccaccc aacagctatg gaatatacat tcttctcatc tgtatacgaa  17880
acatactcta agactggcaa catgctcagt cataaagcaa gtcttaataa attcaaaaaa  17940
ttaaaattat gccaaacata ttctcagacc acagtagaat aaaaatagaa atcaatacca  18000
ggaggaactc tcaaaaccat gaaataacct ggaaactgaa caacttattg ctgaatgact  18060
tttgagtaaa caatgaaatt aaggcagata tcaaaaaatt ctttgaaaca aatgaaaaca  18120
gagacacagc ataccaacaa catatctggg atgtggcaaa agcaatgtta agaggaatgt  18180
ttatagtgct aaatgcctac atcaagaacc tagaaagata tcaaattaat aatctaacac  18240
cacacttaaa ggaactagaa aaacaagaac aaactagttc caaagctaga aaaaaagaga  18300
taactaaaat cagggcagaa ttaatgaaat tgagacctaa aaaatcatac aaaggatcaa  18360
caaaatgaaa agtcagtttt ttaaaaggat aaacaagatg gaaagacctc tagctagatt  18420
aacagagaaa gagagaagat ccaaataagc acaatcagaa atgacaaagg tgacattgca  18480
actgatccca cagaagtaca aaccttccta ttgagtacta tgttcatatc tggttgatag  18540
gaccaataga aacccaacgt cagtatcaca caatataccc ttgtaacaaa cctgcacatg  18600
tactccctga atttaaaatt aaaattaaaa ttaaagttaa aaaattatca ggccgggcac  18660
ggtggctcac agctgtaatc ccagcacttt gggaggccga ggtgggtgga tcacgaggtc  18720
aggagatcga gaccagcctg gccaacatgg tgaaaccccg tctctactaa aaatacaaaa  18780
aaaaaaaaaa aattagctgg gcatagtggt gtgcgcctgt agtcccagct atttaggagg  18840
ctgaggcagg agaatcactt gaactcggga ggcagaggtt gcagtgagcc gagatcatgc  18900
cactgcactc cagcctgggt gacaaagtga gactctgtct caaaaaaaaa aattctctgt  18960
gttcccttct gttgatgaaa tggtattata gttataatta tgtatatttg ttcattcaac  19020
taaaattcta cgtttctgag tagaatatct aatcatattt ctatttgcct tataaaattt  19080
attcagataa ttgcaccata atttactatt tgtgcattgc tgaacctttg cttgttaata  19140
gttttacatc tgtaagaagc aatgcaatga acatcttcac atacataaca tactcctggg  19200
aaaagtccac tgcagaataa aaagtgaaac tgcaagggcc tctaaactct tgtagctgtt  19260
gtagctccac tttgaagttg agcagcagta tagggccatc ttgatgtaga tttttagtct  19320
ttctaaaggg tttttacacc cgtctcttct attgtcatct ctgactcagg ataggtattg  19380
tgacagctcc atgctatagg tgaggaaact gaggctcagg taaatgattt gcccaaagtc  19440
acaaatcaca cagcctcatt ctttctgttt tttttgtacc aattaaccat cctcacctgc  19500
ccctgccacc ttcccactac tctttccagc ctctggtaac catccttcca ctctgtatgt  19560
ccatgagttc aactcttttg atttttagat gccataaata agtgagaaca tgtaatgttt  19620
gtctttctgt gcctggctta tttcacttaa tataatgacc ttcagttcca tctacgttgt  19680
tgcaaatggc aggatttcgt ttttttatgg ctgaatagta ttccaatttg tatgtgtacc  19740
```

```
acattttctt tatccattca tctactgatg gacacttagg ttgtttccaa atcttggtta  19800
ttgtgaatag tgctgcaaca aacatgggag tgcagatatc tcttcaaaat actgatttcc  19860
tttcttttgg gtatataccc agcagtggaa ttgttggatc atatggtagc tctattttta  19920
ctttttgag gaacctccaa actgttttcc atagtggttg tactaactta cattccttcc  19980
aacagtgtag gagggttccc ttttctccac accctcatca gcatttgtta ttgcctgtct  20040
tttggatata aaccaaaaaa tttttcataa atataatttg ggtggctgca cattattcta  20100
tttttcaaag gtatcattat ttatttaacc attctgatgg tcgtttcaac tttttctcta  20160
ttaaaaataa ttctcaatgt aattgttgaa tctaatttct gataattttt taggttagtt  20220
ccttagagac agcattactg agacaaagag aagaatttca aatgctatcc gtgtgtgtta  20280
tcaaattacc ttttggaaag gttatgccaa tgtatatatc caacagaaat aatgctgcta  20340
ttttaaaaat gacattagca ctttttttcca ttttaaaatt ttattgtaaa ttgacattta  20400
ttattgtata tatttatggg gtacaaggtg atttcatgat ttatgaatac aatgaaaaat  20460
aattaaataa agctaattaa catatcaatt acttcacata cttttttgc agtgagaaca  20520
tttgaaattt actctcttag caatttcaaa atgtacaatg ttctattatt aactatattt  20580
actatgctgt gcagtagatc tcaaaaaaat aaaaccaact tattcatcct gtttgagact  20640
ttgtacgctt tgaccatcat ctccccgttg cccccacccc atagcctctg taaccaccat  20700
tctactctct gcttctacca gttccattgt tttagattcc acacataagt gagaacatgt  20760
ggtatttgtt tttcggtgcc tggcttattt aatttaagaa tgctgttgtt ttgatgctgg  20820
aattaatact gttctctttt cccaggcctg ggatgcacag agaatattca aggaggccga  20880
gaagttcttt gtatctgttg gtcttcctaa tatgactcaa ggattctggg aaaattccat  20940
gctaacggac ccaggaaatg ttcagaaagc agtctgccat cccacagctt gggacctggg  21000
gaagggcgac ttcaggtagt ggggctgata cttacacaac tgatactaaa tgggagacaa  21060
cagaggcagg ctgaagttta acttgaattc tttctctgct tttctgagca cagaaaagat  21120
aagttaattc tccttgaact aaggctggga gtccaggaga gcacatttgg gttttcccag  21180
gaaaagagga ttgccagcag gctctaactt gaacctgtgg acaatctgct ttcttggaaa  21240
tatcatgcat ccattggcgt tgtatggtaa tggggatggt tgcacccata tcaggaaaga  21300
tttggtgcta agatttttgg aagatggaca tatgaatcac acattgatct tcccctccat  21360
gtttcactct tgtgaatgag acagaatagg tgaataaata cgcttggatc gaagggagaa  21420
agtggtacat gtcgtaagag agacacaggg catgctctat ggagaactgg aagaaaactg  21480
accacatttg caataggaga taggatcaga ccgtgcttta caagtgggat ttgaattagg  21540
tttggaaaga caagaaggat tcagatacac agagtcggga ggaggaccca agctgtgaga  21600
acagcaggat caaatacaga gaggcaggac ctgacctgca tactgaagtc ggcaagttag  21660
gctagaatga gaaataagtg aaggagagtt tgtgtaatgt ggcagaatga gcacaggctt  21720
cagaatccta ggtgtgtcac ttaatgacta tgcaaccttg gacaaggtat ttaactttct  21780
ttggtttcag tttccttatt ttataaagta gaatagtaat tcccaggttg caggcttgtg  21840
agagccttag gttggattcc ctagcttgaa aaggagatcg ttttacaagt gcttcattga  21900
ggagagctct gaggcagagg ggaatgaggg aagcaggctg ggacaaagga gggaggtaag  21960
taagaatgtg atctttactg gaaacttggc ctcagcctta tcccatgaag ctctctggag  22020
cataacttga gccacagact aggccacacc tcaagacaag gggctagcc ttttatatca  22080
```

-continued ggcagtcttt ggctgtggac tgccccagag tatgggggag cataaccccc atttagccaa 22140
aggcagtgaa gggagcagct gtaggccctt atcagctgtg actcaggcag ctaggggatg 22200
gtggataaag tcttggcagg cccgcaccag cattgactag ggtagggatt ggatctacag 22260
tccttttctg taaagggcca gatagtaaat agtttaagct ttgcagatct ctgttacaac 22320
tactcagctc tgcccttgtg acatgaaaac agccatagac aatacacaaa ccaatggatg 22380
tggctgtgtg ccaataaaaa tttatttata aaaacaatgg ctggccagca ggccatagtt 22440
tactgatgcc agtactagag tgaggcttaa aaatgagaaa gtataagtaa gttttcaagc 22500
acagaatctt acatacagta ggcagtaaat atatagtagt tatttttata attatttcaa 22560
aagagaatag agagaaacca aattagaaaa gtaggttggg gttgtgaaag gaaaatagat 22620
ttactgagca tgagatgaat acataactga atatttcctt accttccccc tttctcttgc 22680
aatgtgtgaa ttaccatgcc ctcccactat cctctccagc tcacttttct cctataaatg 22740
ttgaagccct caaaattatt tttggagaaa ggcacaaacc acagactgtt tctataaatt 22800
ctgtgttctt ttcttctggg catgttctta accttggcaa aataaacttg tgaattgatt 22860
gagacctatc tcaaatagtt tttggtttac agggtcatat tggtgtataa aaggtggctg 22920
agtttattct tgagcaatga ggaggcctcg caggatattg gagggggtgg tgacatgatc 22980
caagtggtat gaaatacatt taggaatcta ctgatgtatg acccctacac ccatctgaat 23040
gaaaatgctc ttgctaagtt aaaaaggacc accatctcat tgccaaatgc agttcttatc 23100
ccactgggct atagcagcat ttgacaagat ttacaagttg tctttcaaat gctttttttt 23160
tttaaccgac ttccacattg tcattctttt ccagatttcc ttgacctctc tgattgtact 23220
ttctccgtct cccctgaata atcttcctct ccccactcct taggtacttg gaccttctaa 23280
aggtttatct ttggtcctct tttcttgcat tctatacctg ttccatggcc catcatatct 23340
atttcccaac ttacatgcta atgattccca agtttcaatt tgcagcccct tctactattt 23400
ctctatcctg gcaataccaa acagcgtgca gtgtcctgaa tgccacattt ccaccccccct 23460 gcccctaagc ctttctcatt gagcactaga acgtcaactt ccatgtcatc taccgggcaa 23520
actcctgcac attgattaag gtccaaattg ctcattgtat cctcagtcat gcccttcttg 23580
gtgcttctag ggaactgtgc ctacattcac tcatttttac gctcaaggct gtgtgtactg 23640
atcacttata gagtacttgc ctcagagttc ttgtagcgga gaactctgct tatctgtctt 23700
cctgttagtc tatgagcaag agaacaggat tcagctgtgc ccattgcttt atattgagca 23760
actagtattg tctctaggac ataagaggtg ggtactcaag attcactggt gaataaatct 23820
tggaaagatg attcatgcta ccaaaacccc atacaactcc actgtaatgg ttaaatgaaa 23880
gtcagtgaga ttcattttca tcttgtccat tttcatgcag gatccttatg tgcacaaagg 23940
tgacaatgga cgacttcctg acagctcatc atgagatggg gcatatccag tatgatatgg 24000
catatgctgc acaacctttt ctgctaagaa atggagctaa tgaaggattc catgaagctg 24060
ttggggaaat catgtcactt tctgcagcca cacctaagca tttaaaatcc attggtcttc 24120
tgtcacccga ttttcaagaa gacaatggta tggacatttt ctcatggctt gttttggagg 24180
ttctttaatc tgatatggga aaaggtattt attatcttat gtaggaaata tttacttttt 24240
gccacataag gtatgaggta tttatgggta actggaaatt actactggtg aaaaaattta 24300
agtatatatc agaacatgtc aacttttggt tttgtattat tgaaaaggga ataagagagg 24360
taactgaatg aatggacttg ggatcctgtg aaatatctaa cagaagtttt tttcttaaag 24420
atgatgaaac agtctcacag aactgaaatg gcttgtccaa ttagtgtcag cattctaact 24480

```
agacccctct ggttctaggt aaaaacttcc caaaacttta gagttggaat atattctaaa  24540
aaccatttta tagaggagta aactgaagac aagagaggga aagtagcccg aagtcaaaac  24600
gcaatgtagt ggcggaacca gaacaagagc cctaatctaa agtcttttcc ataatattat  24660
gcaaagcaaa gtgtagcttt aaattttgga attcttaaag aacaggtgtt taatatcaag  24720
attagaaggg attgaaacat tttgttcatc ctgctgaagc gtgaatttcc cctgtaacat  24780
ccccttagat ctgtgctatc cttcaacatt tctgcctgag gcagcccatt tccttttaga  24840
tgccttggac ttgatggaac atgacaaatg ttcaggagat ccaatttctt cagtgaggat  24900
gccatggctt ttgattcttc ctcataaatg gaggacaaat agagcctaat accttcttct  24960
cttctgtata ttctctcccc tatttttagt tatttgtgac ataaagatca gctcctctgt  25020
ctggagcatt tggtcgatga ggtcaaggtc atgagctcca tccttgagta gacaattcac  25080
tttgccttga tctctggttc cagatacttg gtgatcccac aagggcctgg gagtgagcca  25140
gtgtaaagcc tatcatcatg tttgaaatag ttactgtaag cacagtccta gtggattaca  25200
gaccagtagc agcatcctcc catgaagaca gtaacaaaca aaggtagtta acagtaacca  25260
tacctgcttc ctaattttaa aatatcatta attcaagtca atgaacagat attttattat  25320
ttttaaatat tccctgacag caggtaaaaa tggttgatga ctatgtttct taagatgata  25380
ttagatcagt gatgaaataa tctgtacaac aaaccccatg acacgagttt acctatataa  25440
taaacctgga cacatacccc taaacctaaa ataaaagctt tttttgtttt tttttataaa  25500
aaagatagta ttagacatgg ttaaaccacc ggtttggaaa actcctgctt tttttcttga  25560
ctctgcccct gatttgtgaa taatgttaaa taaattcctt tattccttcc attcctccct  25620
ccctctttct ctttctttct tcttccaaac atatttatcg agcacatact gtgtgcaaga  25680
catttttcta gacactggag acacagtgat gtgaaaagta gataacatcc cctgcttaca  25740
tttcaatgca tttccttcat acactagaga tgaactccac tgcctcttta tgtcactaat  25800
aaaggataaa atgaaataac atgatttgtt aaagcatttt aaattcttgg taaggaagat  25860
atccttacat ttaaagtaca ttgtactttt caccatccag tggatagtgc cctccaggag  25920
ggctcttttg tttcatttcc cctccctggt ttacaggctt ttcactgaat ctgtttagta  25980
tttgtttatt taacaaagac tcacagaagg catcacgtag cagacatggg actaagttat  26040
acagtcttaa atgagacatt aacagtcact gacttcatgg agctttccag aataaacagt  26100
gtgactggga aagtggatga aatagctcta atgaactctg ataagaggta tttaagggag  26160
gaaactgaaa ctaatgaaga aaatgaggat tagaagtaac tttgggtttt atttacctgt  26220
tctgttccag ggcttcaacc tactccaaat ccccttagctg agaaaataaa tatatacata  26280
tcattatgaa tactgtcaat ttttctcatg tatccttata gtaagtacat cttgaggaat  26340
aatattttga ggttaggaaa attctcttta acacaaaaca tccactgtca tcttcatcgt  26400
aatatttatc cttttctatt ttactttcag aaacagaaat aaacttcctg ctcaaacaag  26460
cactcacgat tgttgggact ctgccattta cttacatgtt agagaagtgg aggtggatgg  26520
tctttaaagg ggaaattccc aaagaccagt ggatgaaaaa gtggtgggag atgaagtaag  26580
tcaatgaata tgcaatcagt aaaatgtttt ctaatgagtt tgctgtgtat ttaaaagcat  26640
ttgactggcg tgtacacaca cacacagagg cacacattaa ctaactactt tttgtatttt  26700
tagtttgtta tattttatat tttagtctcc atttggatac catctcctca gataaaattt  26760
ccttgggtca ggtgacacta cttcatactc tatattctta agtattggct tactcattaa  26820
```

```
actatgatat tatgttgaaa gtgatcaatt tattcatttt acatattctt ttatccagcc  26880
ttttaaacaa aacggtgacc ccacatttta ggcaaagcac tggggatcca atgttaataa  26940
tttcaggtat ggtcctcaac cccaaaaaac gtttagttta tggcaggatg tggaaaatta  27000
aaccactgca atttgtagtg ttgtgatggg agggtacagg gtccgttagc gtccagggga  27060
gatccaaagc ccaactgggg gtgtcagatg aggagaggca tttaagccct gagaaaggtg  27120
tgggtgtaga ggggaacaca gagaattcca agctagagag aacctgacac atttgggcaa  27180
cagtgaccat ttccatggtt gcagcactac gttacttatt gctgtgtcac aagtgcctca  27240
cactgtgcct gtcacatgca agtatgaaat aaataggttt ttggaggaag gaattataag  27300
agaaaaagaa aaagaaggaa aaaaagaaag gagagaggga gggagagaat ggaaacaaga  27360
aagaaatcta tcttcttttt accatcatag accctggtca attatttctt tctttatttt  27420
tcttatattt tctttttgaa gtgaagaact catgtgtaac aagcagttcc acatgcacag  27480
gtttaaaaca gtacacttct tctgtcaaga ttctctctgt taacataaat cgtacttggg  27540
aggaaagacg cagcacctat aagaactgtt gccagtgttt aaatattact gaagttatgt  27600
ctacaatgat cctgcaattt taaaggaaaa atgtattcca tttaatcaaa gccaaataca  27660
tgattttgct accttttttt ctggttggat taatcttttg acccctctta gcttatttta  27720
aaggcacatg gaatcagatc cttagagtga ttcattaatg catcaattgt tcctttgttc  27780
agtaaatata aattaattct ttctgtagtg tcaggcacca tgtttgacac tggaattaga  27840
gagaagacca agacacagcc ccaccctcta ggagctcaag tctctagggc aggaagttac  27900
tatagttgaa taactacaaa acggggagat aaatggcaaa ggaggcacaa ctagagaagg  27960
ctaaaggaga ttgaggggtt aattctgcca gaaggtggat gggatcaggg ccaggcttca  28020
cagaggaggg aacacttgag ctaggtaggc gtggagaata agtaagattt caattttatt  28080
aaattctctc tgccaggagt acatgaagtg tggtgcctga gaggaattat tagggctttc  28140
actgtacatt tttggccatg caatgcactt tatgaatgtt attaaattag tcttttgaag  28200
acatagctat tttccaaggg tatattctgg ctgaattaat taaaactaag agataactac  28260
ataatgagct ttactgtctg attttttaaa aatttttatt tattttttat ttttgtaggt  28320
gatttttttt tacattgttt ctatttcacc caacaaccat ttctaatgta aataccattg  28380
attggctgga cacggtggca cctgtaattc cagcattttg ggaggccgag gtgggcagat  28440
cacttgaggc caggagttcg agaccagcct ggccaacatg gtgaaaccct gtctctatta  28500
aaaatacaca aattagttag atgtggtggt gcacacctat aaaccaagct acttgggagg  28560
ctgagatggg agaatcgctt gaacctggga ggcggaggtt gcagtgagcc aagatcgtgc  28620
cactgcacta cagcctgggt gacggagtga gaccctgtct caaaaaaaaa aaaaaaaaat  28680
ttgattgatg aaactgcact agttatgccc acctgcttgt gatgcttgtg atgggtgatc  28740
cacagctaat gtattgtttt cttttctccc caaaggcgag agatagttgg ggtggtggaa  28800
cctgtgcccc atgatgaaac atactgtgac cccgcatctc tgttccatgt ttctaatgat  28860
tactcattca ttcggtaaat tacagttttc ttgtttctgt ttaacttcta gggtttgtgg  28920
acagctgtgc taataacgac aaaaagtagg gataaatgaa gtgataatta taatttttct  28980
atttccaccc ataactacca agctcaatac agatgctcct tgctttacaa tggggttaca  29040
tcccaataaa ctcatcataa gttgaaaata ccttaagaat gcgctgaata cacctaacct  29100
atggtacacc aaagcatagc ctagtctacc ctaaacatgc tcagaacact cacattagcc  29160
tactgttggg caaaatcatc taacacaaac cttattttat aataaagtgt tcaatatctc  29220
```

```
atgtaattat ttaatactgt gctgaaagtg aaaaactttg ggtacttacc attaacatat  29280

acagctgaaa gcgctattgt aaagtcgaaa aatcaaaagt ccaaccgttg taagttggga  29340

actgtctgta tagatgatca atttcaattc aatttaaact aacacaattt attgggttaa  29400

attaaacttg tgtaagatct tgtccccgtc atcagcaatc aatagtatca ttgggagaaa  29460

taaaaagtag ttttgtcttc ttgttactgg cagtttattg tacattgtga tagagaattt  29520

ttaacttgaa gtccaaaaac atatgttctt cacctactaa ccccagtcct tgaatttgct  29580

ggagctcagt ttatttgtaa aatgaaaata atattatcga cctgttataa ggatggattt  29640

gcatcattta tgtgaaaggg ctattaatct gtaaaacaca aaacaaatgt tagctaacat  29700

ttaacagagt aatattgcca tgtttatcaa cagatacata aaacacaaat aggttatgat  29760

gagtgtagag ttcatgtctg gagaaagaga tttcagagat ttgatcagta tctctttggt  29820

tacttgggct ccagatttaa atatatgccc taatctataa ctctaagaca gtaagtaaac  29880

acgggactgc tttttgttg ctttgtctcc tgtgcagata ttacacaagg accctttacc  29940

aattccagtt tcaagaagca ctttgtcaag cagctaaaca tgaaggccct ctgcacaaat  30000

gtgacatctc aaactctaca gaagctggac agaaactgtt gtaagaaata cctcaaaatg  30060

ttgaacctct cctagtattc agtattactc atttccatgc ctaggtttgt atttgatttc  30120

tttgttctaa aaagaaaatt ttatggcctc aaaatgtcct catttacaaa ccaaacattt  30180

aatttgtggt cagacaggaa cctagaccat acaacaattg ggtgggccac ctcttttctc  30240

cctatcataa ctacagccct ctcttcctgg taattggaag gaaagagcgg tttagggtgg  30300

aatatatctg ttaatatgca ttcttttctt atctgccaga agcaaattta gccaagtcaa  30360

agagaagaaa ccatagatca tagatgtaaa tatatgtaca tctggaaccc ctcaaaaggc  30420

cctgaacccc cttttttgt gtagcaatat gctgaggctt ggaaaatcag aaccctggac  30480

cctagcattg gaaaatgttg taggagcaaa gaacatgaat gtaaggccac tgctcaacta  30540

ctttgagccc ttatttacct ggctgaaaga ccagaacaag aattcttttg tgggatggag  30600

taccgactgg agtccatgtg agtacaccca gttgacaagt ttcacaccca ttccttgtct  30660

acttcgtcta gtctcctttg gccccagtct catgaggact tgtgacacag ctgagaatgt  30720

ttctttctct atagtacctg cttctttctc tgctatggtg acagctgcca ttttatggga  30780

gaaaaatcac aactgttgag cacctatgta tgagacatag tgaaagcaac tgtacagaca  30840

aacacacaca gatgcatgca catgtgtgca tacacataca agagtgtgta ctctttcaag  30900

tctgttttat tagtctcatc tttaaaatac atattataac tgtctccaac caactgtact  30960

cgaatcctgc tttccaaaga caaatacttt ttttaaaaca attttaatgc tattatctct  31020

tctttctggc agtcactttc atatttctaa ataattttct tatattgcta ttttgttatt  31080

gctcagtttt aaaccttcgt tttggtctac tcttccactt ccatttcttg ctcttccaat  31140

aaggccttat aatgattttt agtaaaacag ttatcaatgt ttacatcact atgcctgaag  31200

agccaagtaa tgtattattt tgtgtccttt cttatgtggc ttgttgtttg tctcaaagtt  31260

tctacttgcc tgaatttttc ggcttaccta atttgctatc tacgttgtat ttgtttttct  31320

cccaaatatt tcaacatatc tattcttttc agtctcattt tttttcccta gagacttccc  31380

tcttggagtc ttatattctc ctttcccaac atttgttgtt ctcctgggtt gaatccactg  31440

cttcctagat tccatgtctt ctttcttgga ttacctcttg tttttctgga gcatagcctc  31500

ccacagactg tccaagcagg ggcacaaggg gtaggaggat caactgttct ccaaagtggt  31560
```

```
tttaaccaca ccctgacttc cattcctctt cttttcagcc cagtattatt ttcccaccct  31620
cacctgtgct tgaattccaa acctcttttg gatttttttgg ctctttgtgg gtctgtgcct  31680
cctctgtgta caaattaggt catggcttcc tgtccctgag aaagcagtta cccctgtctc  31740
atcatttctc gttttccaaa agcctgttga tacctttaaa agatcccttt actatcactt  31800
tagtgggatc tttggaggaa aaggaaataa gcacatgtgg gcaatctgtt gtctgtaacc  31860
agcagtctgc tatttctctt taatcagatg cagaccaaag catcaaagtg aggataagcc  31920
taaaatcagc tcttggagat aaagcagtga gtattctgga cagtgaattg attatttttg  31980
agtgcacagt cttcacttaa ataggacaca ataaacccat ttcagtgtga actgaaagaa  32040
gagaggccat gtggttcttt tcaaaactat aagttccaga ttctggcctt tgcctttggg  32100
tttttaaagt aacctattcc ttattggata agctattcct acttcttatt gccttgaagg  32160
tgttatgaac ttcaatgaga aaatatctgt atcaatcctt aaatatcaga taccaatcct  32220
ttcaattgac tctcgtcacc attactttta ttctagaaag agaatatggt tatattttga  32280
aaggtagttt gtttttagaa gcggtacagt taggtttttt tagtttgttt tgttttagtc  32340
aatcacctgt atcctggctt cactcagagt gtggcccatg gtccagcagc atttgaatca  32400
cctggaagct tgttaaaaat gcgtaatttc aagcctagcc ctggaccact taatcagaat  32460
ctgcatttta gcaagcctcc aggtgatttg tacgtacaat caagactggg aagctctaat  32520
ttagaacact gcttctcaaa cttggctgca cagtggaatc acatgggaag tttaaaaaat  32580
attaatgcct aggttataca cctccagaga ttctgattta attgttctgg ggtatggagt  32640
caagagttgg gcatcaagag tgtttaaagc tccccaggtg attctagtca cagcaaagtt  32700
tgagaaccac ttatttaggg aaatgcattt tgggggtaac aaaatatttt acaggaaatt  32760
atgttattta caccttaatg tgaattattt acttagctat tgctctgtcg ttaacacctg  32820
tctcagatga tccagtctga ggaagtggta gctttgattg ggaaagagga gaggaaagag  32880
tagtctcggg tagatggggc tcaaaagcct gagagtgggt atgacaccct gaaggctttg  32940
cagggttaga agtcaatctg ggactattgg ataaaatggt ccaagatgct acagcaaatt  33000
gttgtctgca ttggatagat ccaaagattg tgtttctacc ccctacctt tcctgaaaag  33060
ttaaacattg tccaagattc aataacactt ttagtataat tttcatagtt aagacatcaa  33120
aacataaata actcaggagt aaaaagatga acattcaaga aagaaaaaat gaaaatggaa  33180
gtgcatttct ttccaatcat taagagttca agttcctatt tcataataat cattgggtga  33240
ttgtgggact atttctctgt catattttta ttagctcttc cttggcttaa tacattttaa  33300
ttagtctcgg cagatcagga tattttcaat tatctttttt cttgacattt atactcatcc  33360
tctttccatg cagtgagggt tggtaaatag tgttcaggga gtttgattct gtaatgttct  33420
gaggccaatt cactgagcaa caatctgttt tgatgaaacg agatcatata tttagtgcat  33480
ctacacaaca gggtcagaat atctgctcag ttcaaactat ttcatggtga attccaatgg  33540
atctatggca ttattttgag aactcagcct ttaaaatctt ttatatttta tatttataga  33600
gatagtagcc agactgttat tagtaacaat attaataata ttattactat taaaggaact  33660
cctctaaacc tcggtgaaac caagctgaag tgaatgtaac aattcttttg tgaaatatta  33720
taattttttta aagggaaagg agaaacatac aactagtgcc attcattgat tcctactgcc  33780
agctactgga ggaaagagtg aatgctttct tttaagtctt taaaagctat gcaaacataa  33840
gctatttgtt tagcactgga aaacaagaac aaacagatta gcttgctgtt tacaaagtgt  33900
tatttttcat ttgaacgtca agtttttcttt ttacacttat agataagtac atttctgaga  33960
```

```
acgtaccata aaaatagtaa aaactgattt tgtccacaag gtacagacat tttgctacaa  34020
aacccacaac ttttgtttga ctcccatcgg taaacctaca ctcaaggtgt taatttcagt  34080
ttacatcaaa ctaaagtaaa aggacccgtg aacccaatgg ttcctaaagc atggttgcct  34140
gaccagcagc attaccacca cctgggagtt tgttagagat gtaaattatt gggtttcatc  34200
tcgggcttcc tgaatcagac gctctagggg tggacccagc actcagtgtt gtaactaacc  34260
cttcaggtga tacggatgca cacttacatt gaaggtcact gacttaatga atagcaagaa  34320
tctctggaat attaagaata attcttgagg agtatcagat tataaatgtg tcttacgagt  34380
ccctctgagc agtgtctttc ttctgaattt gcagtatgaa tggaacgaca atgaaatgta  34440
cctgttccga tcatctgttg catatgctat gaggcagtac tttttaaaag taaaaaatca  34500
gatgattctt tttgggtgag ttgatttgct gggttctcaa attactccaa ctaggatttc  34560
tcttactctt gagtctgagg agatactctg cctaaacttt tcttcaagtg aaattgataa  34620
aaatctccta gtaacttata cttctttggt attgtggaat ttgggtgact ccatagaggg  34680
ctgatcgtgc cttatttgac tggtaaattg caagagtatt gttcttacta aacagctgtc  34740
actctcttct cagaatgctc tcatacaccc tcagcactga aagaaaaaaa aggcagaact  34800
tcctgccttc attgacctat attctagtat gtatgttgtg tatgtgtcta tgtgtgtaat  34860
atgtaagtga aatatagagt tacaaggtac taagtgctag gagaaaaata taaaagggtc  34920
tggggagggc tggtgtgtgt gtgtgtgtgt tgggcagggg gtaggtcaat tttaaccaaa  34980
atggtcagaa aagacgtcac taatacttga acaagtatat gaagcaggag agagrgagmg  35040
agagagcgag agagcgagag agcgagagcg agagccagca atgcagacaa tggggaaagt  35100
gtctcagctg ggggaaacag caggtgcaga ccctgaggaa ggaatatcct cagcctgtta  35160
aaggaacagc aaggaggcca gtgtggctgg agcagattag aagacaagtg gagacatggc  35220
caggacgatg ttagggcata gaggaaggag ggagagacaa aaggtcatgt gggccttgaa  35280
ggccattcta aggactttgg cttttattct gagttagatg agtagtcact caagggctat  35340
gagccacatg atctacctta ttttgtgcta ggatcgcttg acagctgtga gagcacagtc  35400
ctgtcacatc atatggtaga ccccactcat taccttcatc catgggtgca acacgacgtt  35460
ttctgctggg taggaccagg ttgtgggtgt aaatccgtgt gtggtactca gccatttctg  35520
cccaccacat tgtttgccac aatcctgggc caccgattat tccttgttga ttctcctgct  35580
gttttcagtt tggaaatttt ctataattga aaaagatgtg ggttttatat aaaggcagaa  35640
caaatagtgc caaaacttga tatcacaatt tttatgtagt tgatttcatg tgctttgggc  35700
agcattaatg ttttttttga caattacatc ctctcattgt ttgccctccc ccatgtctct  35760
ctatcctgtg attctctctc taatctcctt ttcaccagca ggggaagtct tcattctctt  35820
gattgtgtcc tctgtgccac aagtgaagat gtttgttttg tttctctaca gggaggagga  35880
tgtgcgagtg gctaatttga aaccaagaat ctcctttaat ttctttgtca ctgcacctaa  35940
aaatgtgtct gatatcattc ctagaactga agttgaaaag gccatcaggt gacattttac  36000
tttcatctaa gggtgagggg gttaccaaat acaacaacaa taaccagtat tttgtgtgtt  36060
cttcctgtgt gccaagcatt attctgagtc atttacatgt gttacctcat gctacaaact  36120
ccacgtaatt ccagaaggat cccacagcag gggaataatc ttgatttgag ttccgccaga  36180
tgtaggctct tacaaaaggg aagaaaaact atagattaca tgttatcaag caagttacca  36240
ctatgggcaa ctagagctca gtcctgctgg gaaatgtgga gagactgtgt agaatgtgca  36300
```

```
cctgaattgt cccatcagag ggctgaggaa gctggggtat ttatttacca cctcccatca  36360
gttattggct gagaactgct tccaggtggc attaattccc cagcatttca gccctgcagg  36420
cagggcagat cttgtggtct gagaatgctc tctggtaaag gggagcaggt gctggttgaa  36480
gaaagtctgg ctagaactca tggaaaatag taagtgcaga agggacgtgg acaggtattg  36540
ccatcatttg ctctcaggac tttgatgtag gattcattta actgcccaaa tcctgaaaca  36600
aggtaggcaa gtacaggatt ccttacatat tgcttggcct ctatgctagg tgagggactt  36660
gcaatgaatg tttagaagaa acagtttgtc caatttgcct caattgtttc ccacaacaga  36720
cagcaggagc gaagaatgga ttgaccttgc agatggtttc ctgtcattat aaaaaggctt  36780
aatataccta ctgcttctgg gcagctcact aggtggccct ctcgagctgc gtcagagtcc  36840
tgtttaactt cggaagcaga tctaagacct gctgggcagg gtgtgcctag aaaatctggc  36900
ttggttggag tgtatgaccc aactgtgccc agagactcac tcacttcctc cagaagactt  36960
gtgtctgtct tgggaaaaac ttctggctga gatctttatg aaaaagctca gccttcctgg  37020
atactcagct gcaagctaca ggggacctca gactctctgt ttccaggatg actcttttca  37080
gatcttttct ggctgaggtt gccaggggtt acctgactaa ttctgcgttg atctctctct  37140
ctctctctgg tggactctga cctcctgacc tgggctatac ccaagggtag gaagatgaga  37200
tgccagacac tttggtcttt gatccagaat gttctccata tcattgtttt tttttttctt  37260
taaacaatct ttatcctttt gcctccataa aagtaagcca tttcccatcc cagtgctgaa  37320
gaaactggca aaggtccctt tcttatgtgc ctccccagtg ctacctccaa atgccaatac  37380
cttttatttg gaaaatatta ctatagagac ttggtcatag gacctgattc atttgtataa  37440
tagaagaggt gtatccaatt atccgtttcc attatttgat ataaagtcat tgtagatgta  37500
ctctgacaga agggaaattc ttgccaaata tgataacttt gcccttaaac acagcagtca  37560
caaatgaata aatgccaacc atttatacat ttccacactt acaactcaat tttccaatgg  37620
agctgttgat gaacctaatc tcgagataac ttcgtataat gtatgctata cgaagttatg  37680
ctaggtaact ataacggtcc taaggtagcg agctagccta ggttgcaagg catgaaagat  37740
gcataattgt caaagactta tatctttaat tagacctatt tactttgctc ttatgatttt  37800
aggtgtatat tccttttttt tttttttgaa acagagtctt gctctgtcac ctaggctaga  37860
gggcagtggc acaatctcgg ctcactgcaa cctctgcctc ccgggttcaa gcgattctcc  37920
tgcctcagcc tcccaagtag ctgggactac agacatgcgc caccatgcct ggctaggtgt  37980
atattcttat gataagctct attatatcct ttcaggaaca atgatataaa cagtaaataa  38040
ctacacacaa ttttattttg tctaagtgtc ccctttgctg ttttttgctt ttgcaaatag  38100
gatgtcccgg agccgtatca atgatgcttt ccgtctgaat gacaacagcc tagagtttct  38160
ggggatacag ccaacacttg gacctcctaa ccagccccct gtttccatat ggctgattat  38220
ttttggtgtt gtgatggcac tggtagtggt tggcatcatc atcctgattg tcactgggat  38280
caaaggtcga aagaagtgag tatcctttcc tagatttatc tgtcttttta gaatgcatga  38340
attggaaatt ttgcaacaaa taacactgta tccacacagg ataattactt acttggacat  38400
ttatctccct aaatattctg atatatccca tagaatcttg tcagatgcta gcagtacctt  38460
accttactag caagctcaca tattatagat gtctagcctg aggtttattg ggatgctgta  38520
gtcaagtgca tcctatccac agtggcatag ccagactgca aactcagtaa ggcattgttc  38580
tcactcatga ctcttgcttc atccacagag actgacatgg agcacaaagt gtaatgtcat  38640
ctaagaatga ggtgcttcaa actactactc tttagttact ttcattcctc cttgggaaac  38700
```

```
tcaaatttat catttgagtt catgggcagg caccctttaa tttgttctag agctgagttg  38760
attgagggct ttaatcacca gggactgact tctagctcct gtcttgagaa agtattaact  38820
cttgttggtc tgttcaaata acttagtatt ttgtatcact ctgacaacat tatctgcatg  38880
ttttcagttg tttaaacata ctctcagttg aatctttaca caaattagtt tattttattt  38940
aattttcttt actatagaga tctctcgatt ctaccaaata acttcatttg aaaaagcaag  39000
gctgtggaga tgggtaaaat cacctgcccc acaagcatga ggacctgact ttgaatcccc  39060
agagcccata tataaagcag atacaggagg caagcatcta taatcccagc actcctccag  39120
ggagatggaa ggcagaggca ggaaagtccc cagaagtctg taggccactc agcctggtgt  39180
acacagcaga ggcaacagac cccatctcaa tcacaatggg tgttgagaat caacactgga  39240
tattgctgtc tgatccccac gtgtgcaatg tagcatacac acttacacac atgcacatgt  39300
gtacgcatac acagatgtgc acaaagcact ttctaggtag tgcagtcaac atggttacaa  39360
tgttcaaaaa tacaaggggg tcatagagtt ccgttaccat tctttgtttc tgagtttcct  39420
tttaaccaaa gttatcagtt tttagtaaaa tgaactatgc actacatatt cttatttacc  39480
aactagtatg ttttagaggt atttccagat ttttcaaaaa attcccaagc aatatatttt  39540
agagattctt tcagattggc tatgtaaagc acttccattt gcctggtaat gtagttgccc  39600
actttgtagc aaatgggtac tcccatggtt accaaatgtt tgtgtctatt taaaaaatac  39660
aacaatttca aataggcaat ttcctgtgca tgctaaagta ggtgcaagat atgtcccagc  39720
aggtaaaagg ctaggttaaa atcatcatga attctaattt taattaatac ttctgaactg  39780
ttctcatagg ggcagaatta atgtacaaac agcaccagct tatgaaagct ctccttttct  39840
ccaactcagc atccttagca cagggtgcca tcagactttt tgacagttat cctttgggtc  39900
agtgtaagta agtgtctttc taccatcact ttaataagga gactttgttt tatttgacag  39960
gaaaaatgaa acaaaaagag aagagaaccc ttatgactcg atggacattg gaaaaggaga  40020
aagcaatgca ggattccaaa acagtgatga tgctcagact tccttttagc aaagcacttg  40080
tcatcttcct gtatgtaaat gctaacttca tagtacacaa aatatgagag tatacacatg  40140
tcattagcta tcaaaactat gatctgttca gtaaacgttg tccaaagagc atcagacttg  40200
agtggacatc ttcactgaca ttgctttcag tatttatttc tgcctaagga tttgacatct  40260
cttctgttta ttaatagaga tgtttatctt agcataaaag agggaaatgt gcctttggcc  40320
tcacagtcta tccagggtga tatggttggg taactggagt tagaagatga gatgatgtct  40380
cttgggggca agtgttggct tcggtgtggc atctgggctg tgaactggtg ggactgttga  40440
ggttgagaat ggtgctcgct ggtcacttga atccaagtgt gacgtcatgc tctgtggctt  40500
ctgccttcac acttctcact tcaagtactg taggaatttg ttcacagtaa tacttgaaat  40560
ggactgtccc ttctttggag gtgcagttca acggagaaag aagccagaca tcaggtagag  40620
accatgacct tttctcttcc aaacttgatc aacatctctc taacaagaca cagctagcac  40680
aggaaactcc acgaacccag agcatgcctg tcagaaacta cttccattat tctcccattg  40740
tggagtaagg gaaaattcca gatgaatgct cgatctgtga gatgggtgcc cagtctctga  40800
aattgtttgt attttctcac agggtctgag caatggtgaa cacaaagccg acctcaataa  40860
atacttatta gatttagaca ctcctct                                      40887
```

<210> SEQ ID NO 23
<211> LENGTH: 199
<212> TYPE: DNA

<213> ORGANISM: Artificial Sequence
<220> FEATURE:
<223> OTHER INFORMATION: Human //XhoI/ (loxP)/ICEUI//NheI// Human

<400> SEQUENCE: 23
catttataca tttccacact tacaactcaa ttttccaatg gagctgttga tgaacctaat 60
ctcgaataac ttcgtataat gtatgctata cgaagttatg ctaggtaact ataacggtcc 120
taaggtagcg agctagccta ggttgcaagg catgaaagat gcataattgt caaagactta 180
tatctttaat tagacctat 199

<210> SEQ ID NO 24
<211> LENGTH: 805
<212> TYPE: PRT
<213> ORGANISM: Artificial Sequence
<220> FEATURE:
<223> OTHER INFORMATION: 24. Humanized human/mouse ACE2 protein
<220> FEATURE:
<221> NAME/KEY: SIGNAL
<222> LOCATION: (1)..(17)
<223> OTHER INFORMATION: Signal sequence of chimeric human/mouse ACE2 protein
<220> FEATURE:
<221> NAME/KEY: MISC_FEATURE
<222> LOCATION: (1)..(19)
<223> OTHER INFORMATION: Mouse portion of chimeric human/mouse ACE2 protein
<220> FEATURE:
<221> NAME/KEY: MISC_FEATURE
<222> LOCATION: (18)..(740)
<223> OTHER INFORMATION: Extracellular Domain of chimeric human/mouse ACE2 protein
<220> FEATURE:
<221> NAME/KEY: MISC_FEATURE
<222> LOCATION: (20)..(740)
<223> OTHER INFORMATION: Human portion of chimeric human/mouse ACE2 protein
<220> FEATURE:
<221> NAME/KEY: MISC_FEATURE
<222> LOCATION: (741)..(805)
<223> OTHER INFORMATION: Mouse portion of chimeric human/mouse ACE2 protein
<220> FEATURE:
<221> NAME/KEY: MISC_FEATURE
<222> LOCATION: (741)..(761)
<223> OTHER INFORMATION: Transmembrane domain of chimeric human/mouse ACE2 protein
<220> FEATURE:
<221> NAME/KEY: MISC_FEATURE
<222> LOCATION: (762)..(805)
<223> OTHER INFORMATION: Cytoplasmic Domain of chimeric human/mouse ACE2 protein

<400> SEQUENCE: 24

```
Met Ser Ser Ser Ser Trp Leu Leu Leu Ser Leu Val Ala Val Thr Thr
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110
```

```
Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                165                 170                 175

Arg Pro Leu Tyr Glu Glu Tyr Val Val Leu Lys Asn Glu Met Ala Arg
            180                 185                 190

Ala Asn His Tyr Glu Asp Tyr Gly Asp Tyr Trp Arg Gly Asp Tyr Glu
        195                 200                 205

Val Asn Gly Val Asp Gly Tyr Asp Tyr Ser Arg Gly Gln Leu Ile Glu
    210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                245                 250                 255

Ser Pro Ile Gly Cys Leu Pro Ala His Leu Leu Gly Asp Met Trp Gly
            260                 265                 270

Arg Phe Trp Thr Asn Leu Tyr Ser Leu Thr Val Pro Phe Gly Gln Lys
        275                 280                 285

Pro Asn Ile Asp Val Thr Asp Ala Met Val Asp Gln Ala Trp Asp Ala
    290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                325                 330                 335

Gly Asn Val Gln Lys Ala Val Cys His Pro Thr Ala Trp Asp Leu Gly
            340                 345                 350

Lys Gly Asp Phe Arg Ile Leu Met Cys Thr Lys Val Thr Met Asp Asp
        355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                405                 410                 415

His Leu Lys Ser Ile Gly Leu Leu Ser Pro Asp Phe Gln Glu Asp Asn
            420                 425                 430

Glu Thr Glu Ile Asn Phe Leu Leu Lys Gln Ala Leu Thr Ile Val Gly
        435                 440                 445

Thr Leu Pro Phe Thr Tyr Met Leu Glu Lys Trp Arg Trp Met Val Phe
    450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                485                 490                 495

Tyr Cys Asp Pro Ala Ser Leu Phe His Val Ser Asn Asp Tyr Ser Phe
            500                 505                 510

Ile Arg Tyr Tyr Thr Arg Thr Leu Tyr Gln Phe Gln Phe Gln Glu Ala
        515                 520                 525
```

```
Leu Cys Gln Ala Ala Lys His Glu Gly Pro Leu His Lys Cys Asp Ile
    530                 535                 540

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
        675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Ile Phe Gly Val Val Met Ala Leu
            740                 745                 750

Val Val Val Gly Ile Ile Ile Leu Ile Val Thr Gly Ile Lys Gly Arg
        755                 760                 765

Lys Lys Lys Asn Glu Thr Lys Arg Glu Glu Asn Pro Tyr Asp Ser Met
    770                 775                 780

Asp Ile Gly Lys Gly Glu Ser Asn Ala Gly Phe Gln Asn Ser Asp Asp
785                 790                 795                 800

Ala Gln Thr Ser Phe
                805
```

<210> SEQ ID NO 25
<211> LENGTH: 2418
<212> TYPE: DNA
<213> ORGANISM: Artificial Sequence
<220> FEATURE:
<223> OTHER INFORMATION: Humanized human/mouse ACE2 CDS
<220> FEATURE:
<221> NAME/KEY: sig_peptide
<222> LOCATION: (1)..(51)
<220> FEATURE:
<221> NAME/KEY: misc_feature
<222> LOCATION: (1)..(57)
<223> OTHER INFORMATION: Mouse portion of CDS encoding chimeric human/mouse ACE2 protein
<220> FEATURE:
<221> NAME/KEY: misc_feature
<222> LOCATION: (52)..(2220)
<223> OTHER INFORMATION: Extracellular domain encoding portion of CDS encoding chimeric human/mouse ACE2 protein
<220> FEATURE:
<221> NAME/KEY: misc_feature
<222> LOCATION: (58)..(2220)
<223> OTHER INFORMATION: Human portion of CDS encoding chimeric human/mouse ACE2 protein
<220> FEATURE:
<221> NAME/KEY: misc_feature
<222> LOCATION: (2221)..(2418)
<223> OTHER INFORMATION: Mouse portion of CDS encoding chimeric
human/mouse ACE2 protein
<220> FEATURE:
<221> NAME/KEY: misc_feature
<222> LOCATION: (2221)..(2283)
<223> OTHER INFORMATION: Transmembrane domain encoding portion of CDS
encoding chimeric human/mouse ACE2 protein
<220> FEATURE:
<221> NAME/KEY: misc_feature
<222> LOCATION: (2284)..(2418)
<223> OTHER INFORMATION: Cytoplasmic domain encoding portion of CDS
encoding chimeric human/mouse ACE2 protein

<400> SEQUENCE: 25

```
atgtccagct cctcctggct ccttctcagc cttgttgctg ttactactgc tcagtccacc     60

attgaggaac aggccaagac atttttggac aagtttaacc acgaagccga agacctgttc    120

tatcaaagtt cacttgcttc ttggaattat aacaccaata ttactgaaga gaatgtccaa    180

aacatgaata atgctgggga caaatggtct gcctttttaa aggaacagtc cacacttgcc    240

caaatgtatc cactacaaga aattcagaat ctcacagtca agcttcagct gcaggctctt    300

cagcaaaatg ggtcttcagt gctctcagaa gacaagagca aacggttgaa cacaattcta    360

aatacaatga gcaccatcta cagtactgga aaagtttgta acccagataa tccacaagaa    420

tgcttattac ttgaaccagg tttgaatgaa ataatggcaa acagtttaga ctacaatgag    480

aggctctggg cttgggaaag ctggagatct gaggtcggca agcagctgag gccattatat    540

gaagagtatg tggtcttgaa aaatgagatg gcaagagcaa atcattatga ggactatggg    600

gattattgga gaggagacta tgaagtaaat ggggtagatg gctatgacta cagccgcggc    660

cagttgattg aagatgtgga acataccttt gaagagatta aaccattata tgaacatctt    720

catgcctatg tgagggcaaa gttgatgaat gcctatcctt cctatatcag tccaattgga    780

tgcctccctg ctcatttgct tggtgatatg tggggtagat tttggacaaa tctgtactct    840

ttgacagttc cctttggaca gaaaccaaac atagatgtta ctgatgcaat ggtggaccag    900

gcctgggatg cacagagaat attcaaggag gccgagaagt tctttgtatc tgttggtctt    960

cctaatatga ctcaaggatt ctgggaaaat tccatgctaa cggacccagg aaatgttcag   1020

aaagcagtct gccatcccac agcttgggac ctggggaagg gcgacttcag gatccttatg   1080

tgcacaaagg tgacaatgga cgacttcctg acagctcatc atgagatggg gcatatccag   1140

tatgatatgg catatgctgc acaacctttt ctgctaagaa atggagctaa tgaaggattc   1200

catgaagctg ttggggaaat catgtcactt tctgcagcca cacctaagca tttaaaatcc   1260

attggtcttc tgtcacccga ttttcaagaa gacaatgaaa cagaaataaa cttcctgctc   1320

aaacaagcac tcacgattgt tgggactctg ccatttactt acatgttaga gaagtggagg   1380

tggatggtct ttaaagggga aattcccaaa gaccagtgga tgaaaaagtg gtgggagatg   1440

aagcgagaga tagttggggt ggtggaacct gtgccccatg atgaaacata ctgtgacccc   1500

gcatctctgt tccatgtttc taatgattac tcattcattc gatattacac aaggaccctt   1560

taccaattcc agtttcaaga agcactttgt caagcagcta aacatgaagg ccctctgcac   1620

aaatgtgaca tctcaaactc tacagaagct ggacagaaac tgttcaatat gctgaggctt   1680

ggaaaatcag aaccctggac cctagcattg gaaaatgttg taggagcaaa gaacatgaat   1740

gtaaggccac tgctcaacta ctttgagccc ttatttacct ggctgaaaga ccagaacaag   1800

aattcttttg tgggatggag taccgactgg agtccatatg cagaccaaag catcaaagtg   1860
```

```
aggataagcc taaaatcagc tcttggagat aaagcatatg aatggaacga caatgaaatg   1920

tacctgttcc gatcatctgt tgcatatgct atgaggcagt actttttaaa agtaaaaaat   1980

cagatgattc tttttgggga ggaggatgtg cgagtggcta atttgaaacc aagaatctcc   2040

tttaatttct ttgtcactgc acctaaaaat gtgtctgata tcattcctag aactgaagtt   2100

gaaaaggcca tcaggatgtc ccggagccgt atcaatgatg ctttccgtct gaatgacaac   2160

agcctagagt ttctggggat acagccaaca cttggacctc ctaaccagcc ccctgtttcc   2220

atatggctga ttatttttgg tgttgtgatg gcactggtag tggttggcat catcatcctg   2280

attgtcactg ggatcaaagg tcgaaagaag aaaaatgaaa caaaaagaga agagaaccct   2340

tatgactcga tggacattgg aaaaggagaa agcaatgcag gattccaaaa cagtgatgat   2400

gctcagactt ccttttag                                                 2418
```

<210> SEQ ID NO 26
<211> LENGTH: 17
<212> TYPE: PRT
<213> ORGANISM: Artificial Sequence
<220> FEATURE:
<223> OTHER INFORMATION: Signal sequence of chimeric human/mouse ACE2 protein

<400> SEQUENCE: 26

```
Met Ser Ser Ser Ser Trp Leu Leu Leu Ser Leu Val Ala Val Thr Thr
1               5                   10                  15

Ala
```

<210> SEQ ID NO 27
<211> LENGTH: 723
<212> TYPE: PRT
<213> ORGANISM: Artificial Sequence
<220> FEATURE:
<223> OTHER INFORMATION: Extracellular domain of chimeric human/mouse ACE2 protein

<400> SEQUENCE: 27

```
Gln Ser Thr Ile Glu Glu Gln Ala Lys Thr Phe Leu Asp Lys Phe Asn
1               5                   10                  15

His Glu Ala Glu Asp Leu Phe Tyr Gln Ser Ser Leu Ala Ser Trp Asn
            20                  25                  30

Tyr Asn Thr Asn Ile Thr Glu Glu Asn Val Gln Asn Met Asn Asn Ala
        35                  40                  45

Gly Asp Lys Trp Ser Ala Phe Leu Lys Glu Gln Ser Thr Leu Ala Gln
    50                  55                  60

Met Tyr Pro Leu Gln Glu Ile Gln Asn Leu Thr Val Lys Leu Gln Leu
65                  70                  75                  80

Gln Ala Leu Gln Gln Asn Gly Ser Ser Val Leu Ser Glu Asp Lys Ser
                85                  90                  95

Lys Arg Leu Asn Thr Ile Leu Asn Thr Met Ser Thr Ile Tyr Ser Thr
            100                 105                 110

Gly Lys Val Cys Asn Pro Asp Asn Pro Gln Glu Cys Leu Leu Leu Glu
        115                 120                 125

Pro Gly Leu Asn Glu Ile Met Ala Asn Ser Leu Asp Tyr Asn Glu Arg
    130                 135                 140

Leu Trp Ala Trp Glu Ser Trp Arg Ser Glu Val Gly Lys Gln Leu Arg
145                 150                 155                 160

Pro Leu Tyr Glu Glu Tyr Val Val Leu Lys Asn Glu Met Ala Arg Ala
```

```
                165                 170                 175

Asn His Tyr Glu Asp Tyr Gly Asp Tyr Trp Arg Gly Asp Tyr Glu Val
            180                 185                 190

Asn Gly Val Asp Gly Tyr Asp Tyr Ser Arg Gly Gln Leu Ile Glu Asp
        195                 200                 205

Val Glu His Thr Phe Glu Glu Ile Lys Pro Leu Tyr Glu His Leu His
    210                 215                 220

Ala Tyr Val Arg Ala Lys Leu Met Asn Ala Tyr Pro Ser Tyr Ile Ser
225                 230                 235                 240

Pro Ile Gly Cys Leu Pro Ala His Leu Leu Gly Asp Met Trp Gly Arg
                245                 250                 255

Phe Trp Thr Asn Leu Tyr Ser Leu Thr Val Pro Phe Gly Gln Lys Pro
            260                 265                 270

Asn Ile Asp Val Thr Asp Ala Met Val Asp Gln Ala Trp Asp Ala Gln
        275                 280                 285

Arg Ile Phe Lys Glu Ala Glu Lys Phe Phe Val Ser Val Gly Leu Pro
    290                 295                 300

Asn Met Thr Gln Gly Phe Trp Glu Asn Ser Met Leu Thr Asp Pro Gly
305                 310                 315                 320

Asn Val Gln Lys Ala Val Cys His Pro Thr Ala Trp Asp Leu Gly Lys
                325                 330                 335

Gly Asp Phe Arg Ile Leu Met Cys Thr Lys Val Thr Met Asp Asp Phe
            340                 345                 350

Leu Thr Ala His His Glu Met Gly His Ile Gln Tyr Asp Met Ala Tyr
        355                 360                 365

Ala Ala Gln Pro Phe Leu Leu Arg Asn Gly Ala Asn Glu Gly Phe His
    370                 375                 380

Glu Ala Val Gly Glu Ile Met Ser Leu Ser Ala Ala Thr Pro Lys His
385                 390                 395                 400

Leu Lys Ser Ile Gly Leu Leu Ser Pro Asp Phe Gln Glu Asp Asn Glu
                405                 410                 415

Thr Glu Ile Asn Phe Leu Leu Lys Gln Ala Leu Thr Ile Val Gly Thr
            420                 425                 430

Leu Pro Phe Thr Tyr Met Leu Glu Lys Trp Arg Trp Met Val Phe Lys
        435                 440                 445

Gly Glu Ile Pro Lys Asp Gln Trp Met Lys Lys Trp Trp Glu Met Lys
    450                 455                 460

Arg Glu Ile Val Gly Val Val Glu Pro Val Pro His Asp Glu Thr Tyr
465                 470                 475                 480

Cys Asp Pro Ala Ser Leu Phe His Val Ser Asn Asp Tyr Ser Phe Ile
                485                 490                 495

Arg Tyr Tyr Thr Arg Thr Leu Tyr Gln Phe Gln Phe Gln Glu Ala Leu
            500                 505                 510

Cys Gln Ala Ala Lys His Glu Gly Pro Leu His Lys Cys Asp Ile Ser
        515                 520                 525

Asn Ser Thr Glu Ala Gly Gln Lys Leu Phe Asn Met Leu Arg Leu Gly
    530                 535                 540

Lys Ser Glu Pro Trp Thr Leu Ala Leu Glu Asn Val Val Gly Ala Lys
545                 550                 555                 560

Asn Met Asn Val Arg Pro Leu Leu Asn Tyr Phe Glu Pro Leu Phe Thr
                565                 570                 575

Trp Leu Lys Asp Gln Asn Lys Asn Ser Phe Val Gly Trp Ser Thr Asp
            580                 585                 590
```

```
Trp Ser Pro Tyr Ala Asp Gln Ser Ile Lys Val Arg Ile Ser Leu Lys
        595                 600                 605

Ser Ala Leu Gly Asp Lys Ala Tyr Glu Trp Asn Asp Asn Glu Met Tyr
    610                 615                 620

Leu Phe Arg Ser Ser Val Ala Tyr Ala Met Arg Gln Tyr Phe Leu Lys
625                 630                 635                 640

Val Lys Asn Gln Met Ile Leu Phe Gly Glu Glu Asp Val Arg Val Ala
                645                 650                 655

Asn Leu Lys Pro Arg Ile Ser Phe Asn Phe Phe Val Thr Ala Pro Lys
            660                 665                 670

Asn Val Ser Asp Ile Ile Pro Arg Thr Glu Val Glu Lys Ala Ile Arg
        675                 680                 685

Met Ser Arg Ser Arg Ile Asn Asp Ala Phe Arg Leu Asn Asp Asn Ser
    690                 695                 700

Leu Glu Phe Leu Gly Ile Gln Pro Thr Leu Gly Pro Pro Asn Gln Pro
705                 710                 715                 720

Pro Val Ser


<210> SEQ ID NO 28
<211> LENGTH: 21
<212> TYPE: PRT
<213> ORGANISM: Artificial Sequence
<220> FEATURE:
<223> OTHER INFORMATION: ransmembrane domain of chimeric human/mouse
      ACE2 protein

<400> SEQUENCE: 28

Ile Trp Leu Ile Ile Phe Gly Val Val Met Ala Leu Val Val Val Gly
1               5                   10                  15

Ile Ile Ile Leu Ile
            20


<210> SEQ ID NO 29
<211> LENGTH: 44
<212> TYPE: PRT
<213> ORGANISM: Artificial Sequence
<220> FEATURE:
<223> OTHER INFORMATION: Cytoplasmic domain of chimeric human/mouse ACE2
      protein

<400> SEQUENCE: 29

Val Thr Gly Ile Lys Gly Arg Lys Lys Lys Asn Glu Thr Lys Arg Glu
1               5                   10                  15

Glu Asn Pro Tyr Asp Ser Met Asp Ile Gly Lys Gly Glu Ser Asn Ala
            20                  25                  30

Gly Phe Gln Asn Ser Asp Asp Ala Gln Thr Ser Phe
        35                  40


<210> SEQ ID NO 30
<211> LENGTH: 21
<212> TYPE: DNA
<213> ORGANISM: Artificial Sequence
<220> FEATURE:
<223> OTHER INFORMATION: 90034mTM Fwd

<400> SEQUENCE: 30

ggcaaccttt cctgctaaga a                                                21


<210> SEQ ID NO 31
<211> LENGTH: 24
```

<212> TYPE: DNA
<213> ORGANISM: Artificial Sequence
<220> FEATURE:
<223> OTHER INFORMATION: 90034mTM Probe (BHQ)

<400> SEQUENCE: 31
cggagccaat gaagggttcc atga 24

<210> SEQ ID NO 32
<211> LENGTH: 23
<212> TYPE: DNA
<213> ORGANISM: Artificial Sequence
<220> FEATURE:
<223> OTHER INFORMATION: 90034mTM Rev

<400> SEQUENCE: 32
gctgcagaaa gtgacatgat ttc 23

<210> SEQ ID NO 33
<211> LENGTH: 23
<212> TYPE: DNA
<213> ORGANISM: Artificial Sequence
<220> FEATURE:
<223> OTHER INFORMATION: 90034mretU Fwd

<400> SEQUENCE: 33
ccctcctcct ccagtgtatc ttt 23

<210> SEQ ID NO 34
<211> LENGTH: 20
<212> TYPE: DNA
<213> ORGANISM: Artificial Sequence
<220> FEATURE:
<223> OTHER INFORMATION: 90034mretU Probe (MGB)

<400> SEQUENCE: 34
cagcttttaa ggaacatatt 20

<210> SEQ ID NO 35
<211> LENGTH: 24
<212> TYPE: DNA
<213> ORGANISM: Artificial Sequence
<220> FEATURE:
<223> OTHER INFORMATION: 90034mretU Rev

<400> SEQUENCE: 35
gctaacattt tatggccaaa tcaa 24

<210> SEQ ID NO 36
<211> LENGTH: 20
<212> TYPE: DNA
<213> ORGANISM: Artificial Sequence
<220> FEATURE:
<223> OTHER INFORMATION: 90034mretU2 Fwd Primer

<400> SEQUENCE: 36
tcgcgagaag caaggagatc 20

<210> SEQ ID NO 37
<211> LENGTH: 26
<212> TYPE: DNA
<213> ORGANISM: Artificial Sequence
<220> FEATURE:
<223> OTHER INFORMATION: 90034mretU2 Probe (BHQ)

<400> SEQUENCE: 37
tctgtgcttg gaaaagcatc attgcc 26

<210> SEQ ID NO 38
<211> LENGTH: 23
<212> TYPE: DNA
<213> ORGANISM: Artificial Sequence
<220> FEATURE:
<223> OTHER INFORMATION: 90034mretU2 Rev

<400> SEQUENCE: 38
ggagagaaga gctggtgtag atg 23

<210> SEQ ID NO 39
<211> LENGTH: 22
<212> TYPE: DNA
<213> ORGANISM: Artificial Sequence
<220> FEATURE:
<223> OTHER INFORMATION: 90034mretD Fwd

<400> SEQUENCE: 39
cgttgtccaa agagcatcag ac 22

<210> SEQ ID NO 40
<211> LENGTH: 27
<212> TYPE: DNA
<213> ORGANISM: Artificial Sequence
<220> FEATURE:
<223> OTHER INFORMATION: 90034mretD Probe ((BHQ)

<400> SEQUENCE: 40
tggacatctt cactgacatt gctttca 27

<210> SEQ ID NO 41
<211> LENGTH: 20
<212> TYPE: DNA
<213> ORGANISM: Artificial Sequence
<220> FEATURE:
<223> OTHER INFORMATION: 90034mretD Rev

<400> SEQUENCE: 41
gaggccaaag gcacatttcc 20

<210> SEQ ID NO 42
<211> LENGTH: 24
<212> TYPE: DNA
<213> ORGANISM: Artificial Sequence
<220> FEATURE:
<223> OTHER INFORMATION: 90034mretD2

<400> SEQUENCE: 42
tctggctata aggaagcaag gatg 24

<210> SEQ ID NO 43
<211> LENGTH: 28
<212> TYPE: DNA
<213> ORGANISM: Artificial Sequence
<220> FEATURE:
<223> OTHER INFORMATION: 90034mretD2 Probe (BHQ)

<400> SEQUENCE: 43
agagcaactg gagttcagag atccaagg 28

<210> SEQ ID NO 44
<211> LENGTH: 23
<212> TYPE: DNA
<213> ORGANISM: Artificial Sequence
<220> FEATURE:
<223> OTHER INFORMATION: 90034mretD2 Rev

<400> SEQUENCE: 44
ccactgccta tggaacaatt aca 23

<210> SEQ ID NO 45
<211> LENGTH: 22
<212> TYPE: DNA
<213> ORGANISM: Artificial Sequence
<220> FEATURE:
<223> OTHER INFORMATION: 90034mretD3 Fwd

<400> SEQUENCE: 45
gggatttgcc acttgatcct tt 22

<210> SEQ ID NO 46
<211> LENGTH: 25
<212> TYPE: DNA
<213> ORGANISM: Artificial Sequence
<220> FEATURE:
<223> OTHER INFORMATION: 90034mretD3 Probe (BHQ)

<400> SEQUENCE: 46
cccttgagta gagaagaccc tggcg 25

<210> SEQ ID NO 47
<211> LENGTH: 21
<212> TYPE: DNA
<213> ORGANISM: Artificial Sequence
<220> FEATURE:
<223> OTHER INFORMATION: 90034mretD3 Rev

<400> SEQUENCE: 47
cagccaccag gacatctaca c 21

<210> SEQ ID NO 48
<211> LENGTH: 24
<212> TYPE: DNA
<213> ORGANISM: Artificial Sequence
<220> FEATURE:
<223> OTHER INFORMATION: 90034mretD4 Fwd

<400> SEQUENCE: 48
actgacatga gagtgctgaa ggtt 24

<210> SEQ ID NO 49
<211> LENGTH: 17
<212> TYPE: DNA
<213> ORGANISM: Artificial Sequence
<220> FEATURE:
<223> OTHER INFORMATION: 90034mretD4 Probe (MGB)

<400> SEQUENCE: 49
atgtggagga agaagat 17

<210> SEQ ID NO 50
<211> LENGTH: 26
<212> TYPE: DNA
<213> ORGANISM: Artificial Sequence
<220> FEATURE:
<223> OTHER INFORMATION: 90034mretD4 Rev

<400> SEQUENCE: 50
acaaaagatg ctcaggtaga aatgaa 26

<210> SEQ ID NO 51
<211> LENGTH: 23
<212> TYPE: DNA
<213> ORGANISM: Artificial Sequence
<220> FEATURE:
<223> OTHER INFORMATION: mGU

<400> SEQUENCE: 51
ggatgggatc ttggcgcacg ggg 23

<210> SEQ ID NO 52
<211> LENGTH: 23
<212> TYPE: DNA
<213> ORGANISM: Artificial Sequence
<220> FEATURE:
<223> OTHER INFORMATION: mGU2

<400> SEQUENCE: 52
tcttggcatt ttcctcggtg agg 23

<210> SEQ ID NO 53
<211> LENGTH: 23
<212> TYPE: DNA
<213> ORGANISM: Artificial Sequence
<220> FEATURE:
<223> OTHER INFORMATION: mGD

<400> SEQUENCE: 53
aagtctcctt attaaagtga tgg 23

<210> SEQ ID NO 54
<211> LENGTH: 23
<212> TYPE: DNA
<213> ORGANISM: Artificial Sequence
<220> FEATURE:
<223> OTHER INFORMATION: mGD2

<400> SEQUENCE: 54
agagaaccct tatgactcga tgg 23

<210> SEQ ID NO 55
<211> LENGTH: 396
<212> TYPE: DNA
<213> ORGANISM: Artificial Sequence
<220> FEATURE:
<223> OTHER INFORMATION: 90034 Border A

<400> SEQUENCE: 55
atctgtcctc tccaggatta acttcatatt ggtccagcag cttgtttact gttctcttct 60
gtttcttctt ctgctttttt tttcttctct tctcagtgcc caacccaagt tcaaaggctg 120
atgagagaga aaaactcatg aagagatttt actctaggga aagttgctca gtggatggga 180
tcttggaaaa ggagaaagca atgcaggatt ccaaaacagt gatgatgctc agacttcctt 240
ttagcaaagc acttgttatc ttcctgtatg taaatgctaa cttcatagta cacaaaatat 300
gagagtatac acatgtcatt agctatcaaa actatgatct gttcagtaaa cgttgtccaa 360
agagcatcag acttgagtgg acatcttcac tgacat 396

<210> SEQ ID NO 56
<211> LENGTH: 24
<212> TYPE: DNA
<213> ORGANISM: Artificial Sequence
<220> FEATURE:
<223> OTHER INFORMATION: hEx3-4 Fwd

<400> SEQUENCE: 56
aacccagata atccacaaga atgc 24

<210> SEQ ID NO 57
<211> LENGTH: 21
<212> TYPE: DNA
<213> ORGANISM: Artificial Sequence
<220> FEATURE:
<223> OTHER INFORMATION: hEx3-4 Rev

<400> SEQUENCE: 57
gcccagagcc tctcattgta g 21

<210> SEQ ID NO 58
<211> LENGTH: 29
<212> TYPE: DNA
<213> ORGANISM: Artificial Sequence
<220> FEATURE:
<223> OTHER INFORMATION: hEx3-4 Probe

<400> SEQUENCE: 58
ttgaaccagg tttgaatgaa ataatggca 29

<210> SEQ ID NO 59
<211> LENGTH: 21
<212> TYPE: DNA
<213> ORGANISM: Artificial Sequence
<220> FEATURE:
<223> OTHER INFORMATION: hEx16-17 Fwd

<400> SEQUENCE: 59
ttgaaaaggc catcaggatg t 21

<210> SEQ ID NO 60
<211> LENGTH: 22
<212> TYPE: DNA
<213> ORGANISM: Artificial Sequence
<220> FEATURE:
<223> OTHER INFORMATION: hEx16-17 Rev

<400> SEQUENCE: 60
gtcattcaga cggaaagcat ca 22

<210> SEQ ID NO 61
<211> LENGTH: 14
<212> TYPE: DNA
<213> ORGANISM: Artificial Sequence
<220> FEATURE:
<223> OTHER INFORMATION: hEx16-17 Probe

<400> SEQUENCE: 61
ccggagccgt atca 14

<210> SEQ ID NO 62
<211> LENGTH: 23
<212> TYPE: DNA
<213> ORGANISM: Artificial Sequence
<220> FEATURE:
<223> OTHER INFORMATION: mEx11-12 Fwd

<400> SEQUENCE: 62
gagcctctgc ctcatgatga aac 23

<210> SEQ ID NO 63

-continued

```
<211> LENGTH: 22
<212> TYPE: DNA
<213> ORGANISM: Artificial Sequence
<220> FEATURE:
<223> OTHER INFORMATION: mEx11-12 Rev

<400> SEQUENCE: 63

tgcttgacaa agagcttctt ga                                    22


<210> SEQ ID NO 64
<211> LENGTH: 23
<212> TYPE: DNA
<213> ORGANISM: Artificial Sequence
<220> FEATURE:
<223> OTHER INFORMATION: mEx11-12 Probe

<400> SEQUENCE: 64

tgtgaccctg catctctgtt cca                                   23


<210> SEQ ID NO 65
<211> LENGTH: 23
<212> TYPE: DNA
<213> ORGANISM: Artificial Sequence
<220> FEATURE:
<223> OTHER INFORMATION: mEx17-18 Fwd

<400> SEQUENCE: 65

ggttggcatc atcatcctga ttg                                   23


<210> SEQ ID NO 66
<211> LENGTH: 24
<212> TYPE: DNA
<213> ORGANISM: Artificial Sequence
<220> FEATURE:
<223> OTHER INFORMATION: mEx17-18 Rev

<400> SEQUENCE: 66

tcgagtcata agggttctct tctc                                  24


<210> SEQ ID NO 67
<211> LENGTH: 27
<212> TYPE: DNA
<213> ORGANISM: Artificial Sequence
<220> FEATURE:
<223> OTHER INFORMATION: mEx17-18 Probe

<400> SEQUENCE: 67

tcactgggat caaaggtcga aagaaga                               27
```

NON-HUMAN ANIMALS COMPRISING A HUMANIZED ACE2 LOCUS

CROSS-REFERENCE TO RELATED APPLICATIONS

This application is a National Phase application of International Application No. PCT/US2021/039162, filed Jun. 25, 2021, which claims benefit of priority to U.S. Provisional Application No. 63/044,976, filed Jun. 26, 2020, U.S. Provisional Application No. 63/045,183, filed Jun. 28, 2020, U.S. Provisional Application No. 63/093,892, filed Oct. 20, 2020, and U.S. Provisional Application No. 63/093,994, filed Oct. 20, 2020, each of which is incorporated by reference in its entirety.

FEDERALLY SPONSORED RESEARCH OR DEVELOPMENT

This invention was made with Government support under Agreement HHS0100201700020C, awarded by the U.S. Department of Health and Human Services. The Government has certain rights in the invention.

SEQUENCE LISTING

The official copy of the sequence listing is submitted electronically via EFS-Web as an XML formatted sequence listing with a file named 10787US01_ST26.xml, created on Dec. 13, 2022, and having a size of 198 kilobytes, and is filed concurrently with the specification. The sequence listing contained in this XML formatted document is part of the specification and is herein incorporated in its entirety.

TECHNICAL FIELD

Described herein are (1) non-human animals, e.g., rodents (e.g., rats and mice), and tissues or cells derived therefrom, that comprise a human or humanized Angiotensin-converting enzyme 2 (ACE2) locus, e.g., at an endogenous ACE2 locus, and that express therefrom a human or humanized ACE2 protein, (2) nucleic acids encoding the human or humanized ACE2 proteins and the human or humanized ACE2 proteins so encoded, (3) non-human animal embryonic stem cells comprising the nucleic acids encoding the human or humanized ACE2 protein, (4) methods of making and using the non-human animal embryonic stem cells, including methods of making the non-human animals from the non-human animal embryonic stem cells, and (5) methods of making and using the non-human animals that comprise a human or humanized ACE2 locus, e.g., at an endogenous ACE2 locus. Such non-human animals express a human or humanized ACE2 protein comprising an extracellular domain of a human ACE2 protein, and thus, may be used to delineate the biological activity of ligand binding to human ACE2 protein. Such models may be useful, e.g., for understanding coronavirus infections, e.g., SARS-CoV and/or SARS-CoV-2 infection, and/or evaluating the efficacy of a vaccine or treatment protocol for same.

BACKGROUND

Angiotensin-converting enzyme 2 (ACE2) is an enzyme found on cell surface of cells in the lungs, arteries, heart, kidney, and intestines. A primary function of ACE2 is to cleave the carboxyl-terminal amino acid phenylalanine from angiotensin II and hydrolyze it into the vasodilator angiotensin. ACE2 also serves as the main entry point into cells for some coronaviruses (CoVs).

CoVs can cause diseases in animals. In humans, CoVs are responsible for many of the epidemics of recent years. In 2002, the Severe Acute Respiratory Syndrome Coronavirus (SARS-CoV) was responsible for the SARS epidemic, which was contained in July 2003. Since 2004, there have not been any known cases of SARS reported. In 2012, the Middle East Respiratory Syndrome Coronavirus (MERS-CoV) emerged as the second coronavirus resulting in a global public health crisis, although an outbreak with a 32.97% fatality rate did not occur until 2014. Cases of MERS continue to be reported, with a 34.4% case-fatality ratio. SARS-CoV-2, identified in 2019, is the cause of the disease COVID-19 and infection with SARS-CoV-2 reached pandemic levels within months of its first identification. The COVID-19 pandemic is currently ongoing.

Infection with SARS-CoV-2 causes symptoms ranging from mild or non-existent to death resulting from severe damage to the lungs and possibly other organs. Due to variability in testing capabilities among different countries, reported fatality rates vary between 1 to 5 percent. If an infected patient is over 50 years old or if they suffer from an underlying condition such as asthma, diabetes, or heart disease, their chances of surviving COVID-19 decreases. Since infected individuals who are asymptomatic may contribute to the spread of the virus, and since an effective vaccine or treatment protocol is not yet available, the only means by which to reduce transmission of SARS-CoV-2 is requiring all individuals to practice social distancing. This had led to a demand for shortcuts in the regulatory approval process for a potential vaccine or treatment, with human trials of lead vaccine or treatment candidates set to proceed at an unprecedented fast pace.

Infection with SARS-CoV and SARS-CoV-2 is mediated through ACE2. Accordingly, a non-human animal model for coronavirus infection, e.g., SARS-CoV and/or SARS-CoV-2 infection, may be beneficial for the testing of putative vaccines and/or treatments against current and future infection.

SUMMARY

Disclosed herein are a non-human animal, non-human animal cell, or non-human animal genome comprising a modified endogenous ACE2 locus encoding a recombinant ACE2 protein.

In some embodiments, a recombinant ACE2 protein comprises in operable linkage: (i) an ACE2 signal sequence of a non-human animal ACE2 protein or an ACE2 signal sequence of a human ACE2 protein, (ii) an extracellular domain of a human ACE2 protein, (iii) a transmembrane domain of a non-human animal ACE2 protein or a transmembrane domain of a human ACE2 protein, and (iv) a cytoplasmic domain of a non-human animal ACE2 protein or a cytoplasmic domain of a human ACE2 protein. In some embodiments, a recombinant ACE2 protein comprises in operable linkage: (i) an ACE2 signal sequence of a non-human animal ACE2 protein, (ii) an extracellular domain of a human ACE2 protein, (iii) a transmembrane domain of a non-human animal ACE2 protein, and (iv) a cytoplasmic domain of a non-human animal ACE2 protein. In some embodiments a recombinant ACE2 protein comprises an amino acid sequence set forth as SEQ ID NO:24.

In some embodiments, a modified endogenous ACE2 locus of a non-human animal comprises a replacement of the nucleotide sequence encoding the extracellular domain of the endogenous ACE2 protein with a nucleotide sequence encoding the extracellular domain of a human ACE2 protein such that the nucleotide sequence encoding the extracellular domain of a human ACE2 protein is operably linked to an endogenous nucleotide sequence encoding (iii) the transmembrane domain of an endogenous non-human animal ACE2 protein, and (iv) the cytoplasmic domain of an endogenous non-human animal ACE2 protein. In some embodiments the modified endogenous ACE2 locus comprises a nucleotide sequence set forth as SEQ ID NO:5 or set forth as SEQ ID NO:22.

In some embodiments, the nucleotide sequence encoding the extracellular domain of a human ACE2 protein comprises part of the coding sequence of coding exon 1, all of the coding sequences of coding exon 2 to coding exon 16, inclusive, and part of the coding sequence of coding exon 17 of a human ACE2 gene.

Also described herein are nucleotide molecules, e.g., targeting vectors, which may be useful in making non-human animals comprising a modified endogenous ACE2 locus that expresses a human or humanized ACE2 protein. In some embodiments, a targeting vector comprises an insert nucleotide that (a) comprises a nucleotide sequence that encodes at least an extracellular domain of a human ACE2 protein and (b) is flanked by 5' and 3' homology arms that undergo homologous recombination with an endogenous ACE2 locus of a non-human animal, wherein following the homologous recombination of the endogenous ACE2 locus with the 5' and 3' homology arms, the genetically modified endogenous ACE2 locus of the non-human animal encodes, under the control of an endogenous ACE2 promoter, a recombinant ACE2 protein that comprises in operable linkage: (i) an ACE2 signal sequence of a non-human animal ACE2 protein or an ACE2 signal sequence of a human ACE2 protein (ii) the extracellular domain of a human ACE2 protein, (iii) a transmembrane domain of a non-human animal ACE2 protein or a transmembrane domain of a human ACE2 protein, and (iv) a cytoplasmic domain of a non-human animal ACE2 protein or a cytoplasmic domain of a human ACE2 protein. In some embodiments, following the homologous recombination of the endogenous ACE2 locus with the 5' and 3' homology arms, the genetically modified endogenous ACE2 locus of the non-human animal encodes, under the control of an endogenous ACE2 promoter, a recombinant ACE2 protein that comprises in operable linkage: (i) an ACE2 signal sequence of an endogenous non-human animal ACE2 protein, (ii) an extracellular domain of a human ACE2 protein, (iii) a transmembrane domain of an endogenous non-human animal ACE2 protein, and (iv) a cytoplasmic domain of an endogenous non-human animal ACE2 protein. In some embodiments, following homologous recombination, the nucleotide sequence that encodes at least an extracellular domain of a human ACE2 protein replaces an orthologous sequence at the endogenous ACE2 locus. In some targeting vector embodiments, the nucleotide sequence that encodes at least an extracellular domain of a human ACE2 protein comprises part of the coding sequence of coding exon 1 and all of the coding sequences of coding exon 2 to coding exon 16, inclusive, and part of the coding sequence of exon 17 of a human ACE2 gene.

In some embodiments, a targeting vector or nucleic acid comprises a nucleotide sequence set forth as SEQ ID NO:5, SEQ ID NO:22, or SEQ ID NO:25.

In some embodiments, an insert nucleic acid further comprises a second nucleic acid sequence comprising a sequence encoding a selectable marker, preferably wherein the sequence encoding a selectable marker is operably linked to a promoter. In some targeting vector embodiments, the insert nucleotide comprises site-specific recombination sites flanking the second nucleic acid sequence. In some embodiments, the second nucleic acid sequence further comprises a sequence encoding a site-specific recombinase, preferably wherein the sequence encoding the selectable marker is operably linked to a promoter. In some embodiments, a targeting vector comprises from 5' to 3' a nucleotide sequence comprising the nucleotide sequences set forth as SEQ ID NO:18, SEQ ID NO:19, SEQ ID NO:20, and SEQ ID NO:21.

Also described herein are nucleic acids. A nucleic acid embodiment herein may comprises a sequence set forth as SEQ ID NO:5. In some embodiments, a nucleic acid comprises a sequence set forth as SEQ ID NO:22. In some embodiments, a nucleic acid comprises a sequence set forth as SEQ ID NO:25.

Also described herein are a non-human animal, non-human animal cell, or non-human animal genome comprising a genetically modified endogenous ACE2 locus. In some embodiments, a non-human animal, non-human animal cell, or non-human animal genome is modified at an endogenous ACE2 locus with a targeting vector as described herein or to comprise a nucleic acid described herein.

Accordingly, also provided herein are methods of making a non-human animal, non-human animal cell, or non-human animal genome comprising a humanized endogenous ACE2. In some embodiments, a method comprises (a) contacting a non-human animal embryonic stem (ES) cell with a targeting construct comprising an insert nucleic acid that (i) comprises a first nucleic acid sequence encoding at least an extracellular domain and (ii) is flanked by 5' and 3' homology arms that undergo homologous recombination with an endogenous ACE2 locus in the ES cell to form a modified ES cell comprising a genetically modified endogenous ACE2 locus; and wherein following the homologous recombination of the endogenous ACE2 locus with the 5' and 3' homology arms, the endogenous ACE2 locus encodes, under the control of an endogenous ACE2 promoter, a recombinant ACE2 protein that comprises in operable linkage: (i) an ACE2 signal sequence of a non-human animal ACE2 protein or an ACE2 signal sequence of a human ACE2 protein (ii) the extracellular domain of a human ACE2 protein, (iii) a transmembrane domain of a non-human animal ACE2 protein or a transmembrane domain of a human ACE2 protein, and (iv) a cytoplasmic domain of a non-human animal ACE2 protein or a cytoplasmic domain of a human ACE2 protein; (b) introducing the modified non-human animal ES cell into a host embryo of non-human animal to form a donor cell-non-human animal embryo complex; and (c) gestating the donor cell-non-human animal embryo in a surrogate non-human animal mother, wherein the surrogate non-human animal mother produces rodent progeny that express the human or humanized ACE2 protein. In some embodiments, a non-human animal embryonic stem cell is contacted with the targeting vector described herein.

In some embodiments, a non-human animal, no-human animal cell, or non-human animal genome described herein is made according to the methods described herein. In some embodiments, a non-human animal, non-human animal cell, or non-human animal genome comprises a human or humanized ACE2 locus that expresses a human or humanized ACE2 protein, wherein the amino acid sequence of the extracellular domain of a human ACE2 protein is set forth in SEQ ID NO: 27. In some embodiments, a non-human animal, non-human animal cell, or non-human animal genome is heterozygous for the genetically modified endogenous ACE2 locus. In some embodiments, a non-human animal, non-human animal cell, or non-human animal genome is homozygous for the genetically modified endogenous ACE2 locus. In some embodiments, a non-human animal is a mammal, a non-human animal cell is a mammalian cell, or a non-human animal genome is a mammalian genome. In some embodiments, a non-human animal is a rodent, a non-human animal cell is a rodent cell, or a non-human animal genome is a rodent genome. In some embodiments, a non-human animal is a rat or mouse, tanon-human animal cell is a rat cell or a mouse cell, or a non-human animal genome is a rat genome or a mouse genome. In some embodiments, a non-human animal is a mouse, a non-human animal cell is a mouse cell, or a non-human animal genome is a mouse genome. In some animal, cell and/or genome embodiments, the animal, cell and/or genome comprises a sequence encoding a recombinant ACE2 protein and the animal, cell and/or genome expresses the recombinant ACE2 protein.

In some embodiments, a non-human animal comprising a genetically modified endogenous ACE2 locus as described herein expresses a recombinant ACE2 protein in an organ selected from the group consisting of colon, duodenum, kidney, heart, liver, lung, trachea, and any combination thereof. In some embodiments, the expression pattern of a recombinant ACE2 protein in a genetically modified non-human animal as described herein follows the expression pattern of a non-human animal ACE2 protein in a control non-human animal comprising a wildtype endogenous ACE2 locus.

In some embodiments, the recombinant ACE2 protein is expressed on epithelial cells. Accordingly, also described herein is a non-human animal cell expressing a recombinant ACE2 protein, optionally wherein the non-human animal cell (e.g., rat cell or mouse cell) is a somatic cell, optionally wherein the somatic cell is an epithelial cell. Non-limiting examples of epithetical cells that may express a recombination ACE2 protein as described herein include respiratory and/or gastrointestinal epithelial cells, e.g., an alveolar cell of the lung, an esophagus upper and stratified epithelial cell, an absorptive enterocyte from the ileum or colon, etc. In some embodiments, a non-human animal cell as described herein expresses the recombinant ACE2 protein in the epithelium of small intestine villi, surface epithelium of the large intestine (colon), the epithelium of large to small bronchioles and bronchi of the lung, respiratory epithelium of the trachea, proximal tubular epithelium of the kidney, respiratory epithelium of the nasal cavity, and/or the stratum granulosum and/or stratum spinosum of oral mucosa/tongue in the oral cavity.

In some embodiments, a non-human animal cell as described herein comprises a modified ACE2 locus encoding a human or humanized ACE2 protein as described herein, but does not express the human or humanized ACE2 protein. In some embodiments, the non-human animal cell that comprises a modified ACE2 locus encoding a human or humanized ACE2 protein as described herein, but does not express the human or humanized ACE2 protein is a non-human animal embryonic stem (ES) cell, pluripotent cell, or a germ cell. Methods for making such cells are also described. In some embodiments, a method for genetically modifying an endogenous ACE2 locus in an isolated non-human animal (e.g., rodent (e.g., rat or mouse)) embryonic stem (ES) cell, pluripotent cell, or a germ cell comprises introducing into the cell a targeting vector as described herein and (b) identifying a modified rodent ES cell comprising a targeted genetic modification at the ACE2 locus, wherein the modified endogenous ACE2 locus encodes, under the control of an endogenous ACE2 promoter, a recombinant ACE2 protein that comprises in operable linkage: (i) an ACE2 signal sequence of an endogenous non-human animal ACE2 protein, (ii) an extracellular domain of a human ACE2 protein, (iii) a transmembrane domain of an endogenous non-human animal ACE2 protein, and (iv) a cytoplasmic domain of an endogenous non-human animal ACE2 protein.

Also described herein are a non-human animal tissue or a composition comprising the non-human animal cells described herein. In some composition embodiments, the composition further comprises a spike protein of a coronavirus, wherein the spike protein binds the recombinant ACE2 protein and/or a therapeutic agent that inhibits or prevents binding of an ACE2 ligand to the recombinant ACE2 protein, optionally wherein the ACE2 ligand comprises a spike protein of a coronavirus. In some embodiments, a therapeutic agent may be an antigen-binding protein that binds the spike protein of a coronavirus.

Also described herein is use of a non-human animal as a model of coronavirus infection, wherein the non-human animal is described herein and comprises: (a) a genetically modified endogenous ACE2 locus encoding a recombinant ACE2 protein that comprises in operable linkage: (i) an ACE2 signal sequence of a non-human animal ACE2 protein or an ACE2 signal sequence of a human ACE2 protein, (ii) an extracellular domain of a human ACE2 protein, (iii) a transmembrane domain of a non-human animal ACE2 protein or a transmembrane domain of a human ACE2 protein, and (iv) a cytoplasmic domain of a non-human animal ACE2 protein or a cytoplasmic domain of a human ACE2 protein, wherein the non-human animal expresses the recombinant ACE2 protein, and (b) a coronavirus comprising a spike protein that binds to a human ACE2 protein.

Also provided is a method of screening drug candidates that target a ligand of a human ACE2 protein, comprising: a) introducing into a genetically modified non-human animal as described herein a ligand of a human ACE2 protein, wherein the non-human animal expresses a recombinant ACE2 protein as described herein; b) contacting the non-human animal with a drug candidate of interest, wherein the drug candidate is directed against the ligand of a human ACE2 protein; and c) determining if the drug candidate is efficacious in preventing, reducing or eliminating binding of the ligand of a human ACE2 protein to the recombinant ACE2 protein. In some embodiments, introducing comprises infecting the non-human animal with a coronavirus, wherein the coronavirus comprises a spike protein, and wherein the spike protein comprises the ligand of a human ACE2 protein, e.g., wherein the coronavirus is SARS-CoV-2. In some embodiments, preventing, reducing or eliminating binding of SARS-CoV-2 to the recombinant ACE2 protein results in preventing, reducing, or eliminating one or more COVID-19 symptoms in the non-human animal.

Also disclosed is an ACE2-null mouse comprising an endogenous ACE2 locus comprising a deletion of a sequence encoding ACE2. In some embodiments, an ACE2-null mouse comprises an endogenous ACE2 locus as depicted in FIG. 2B, e.g., comprising a deletion of 46,894 bp of ACE2 on the X chromosome, encompassing 27 bp of ACE2 5' untranslated region (UTR) and the entire coding sequence with intervening introns, except for 65 bp at the 3' end of the last coding exon, optionally wherein the endogenous locus also comprises a C to T point mutation in the ACE2 3' UTR. In some embodiments, an endogenous ACE2 locus of an ACE2-null mouse comprises a sequence set forth as SEQ ID NO:55. In some ACE2-null embodiments, a mouse as described herein is heterozygous for the endogenous locus comprising a deletion of a sequence encoding ACE2, e.g., for the endogenous locus depicted in FIG. 2B, e.g., for an endogenous locus comprising a deletion of 46,894 bp of ACE2 on the X chromosome, encompassing 27 bp of ACE2 5' untranslated region (UTR) and the entire coding sequence with intervening introns, except for 65 bp at the 3' end of the last coding exon, optionally wherein the endogenous locus also comprises a C to T point mutation in the ACE2 3' UTR. In some embodiments, an ACE2-null mouse as described herein is homozygous for the endogenous locus comprising a deletion of a sequence encoding ACE2, e.g., for the endogenous locus depicted in FIG. 2B, e.g., for an endogenous locus comprising a deletion of 46,894 bp of ACE2 on the X chromosome, encompassing 27 bp of ACE2 5' untranslated region (UTR) and the entire coding sequence with intervening introns, except for 65 bp at the 3' end of the last coding exon, optionally wherein the endogenous locus also comprises a C to T point mutation in the ACE2 3' UTR. Also provided are nucleic acids for making an ACE2-null mouse, e.g., a nucleic acid comprising a sequence set forth as SEQ ID NO:51, SEQ ID NO:52, SEQ ID NO:53, and/or SEQ ID NO:54.

DESCRIPTION OF THE DRAWINGS

FIG. 1A shows schematics (not-to-scale) of the human and mouse ACE2 loci. The untranslated and coding exons are represented by rectangles, coding sequences are indicated by the filled boxes, the untranslated regions (UTRs) are indicated by the unfilled boxes, and various accession numbers for non-limiting examples of ACE2 genes, along with the chromosomal locations, are indicated at the top of the figure. The asterisks indicate the locations of (A) the upstream (7878hTU) and downstream (7878hTD) primers for the gain-of-allele assay or (B) the upstream (7878mTU) and downstream (7878mTD) primers for the loss-of-allele assay. The fragment to be inserted into the mouse ACE2 locus for humanization is shown underneath the human ACE2 allele, and the fragment to be deleted from the mouse ACE2 locus is shown underneath the mouse ACE2 allele.

TABLE 1

| | |
|---|---|
| A. 5' mouse/5' human | AAGATGTCCA GCTCCTCCTG GCTCCTTCTC<br>AGCCTTGTTG CTGTTACTAC TGCTCAGTCC/<br>ACCATTGAGG AACAGGCCAA GACATTTTTG<br>GACAAGTTTA ACCACGAAGC CGAAGACCTG<br>(SEQ ID NO: 18) |
| B. Human//**XhoI**//(*loxP*)<br>Cassette | CATTTATACA TTTCCACACT TACAACTCAA<br>TTTTCCAATG GAGCTGTTGA TGAACCTAAT<br>//**CTCGAG**//<br>(*ATAACTTCGTATAATGTATGCTATACGAAGTTAT*)<br>ATGCATGCCA GTAGCAGCAC CCACGTCCAC<br>CTTCTGTCTA GTAATGTCCA ACACCTCCCT<br>(SEQ ID NO: 19) |
| C. Cassette<br>(*loxP*)/ICEUI//**NheI**//human | CATTCTCAGT ATTGTTTTGC CAAGTTCTAA<br>TTCCATCAGA CCTCGACCTG CAGCCCCTAG<br>(*ATAACTTCGTATAATGTATG CTATACGAAGTTAT*)<br>GCTAGG TAACTATAACGGTCCTAAGGTAGCGA<br>/**GCTAGC** CTAGGTTGCA AGGCATGAAA<br>GATGCATAAT TGTCAAAGAC TTATATCTTT<br>AATTAGACCT<br>(SEQ ID NO: 20) |
| D. 3' human/3' mouse | AGCCTAGAGT TTCTGGGGAT ACAGCCAACA<br>CTTGGACCTC CTAACCAGCC CCCTGTTTCC/<br>ATATGGCTGA TTATTTTTGG TGTTGTGATG<br>GCACTGGTAG TGGTTGGCAT CATCATCCTG<br>(SEQ ID NO: 21) |

Figure 1B:
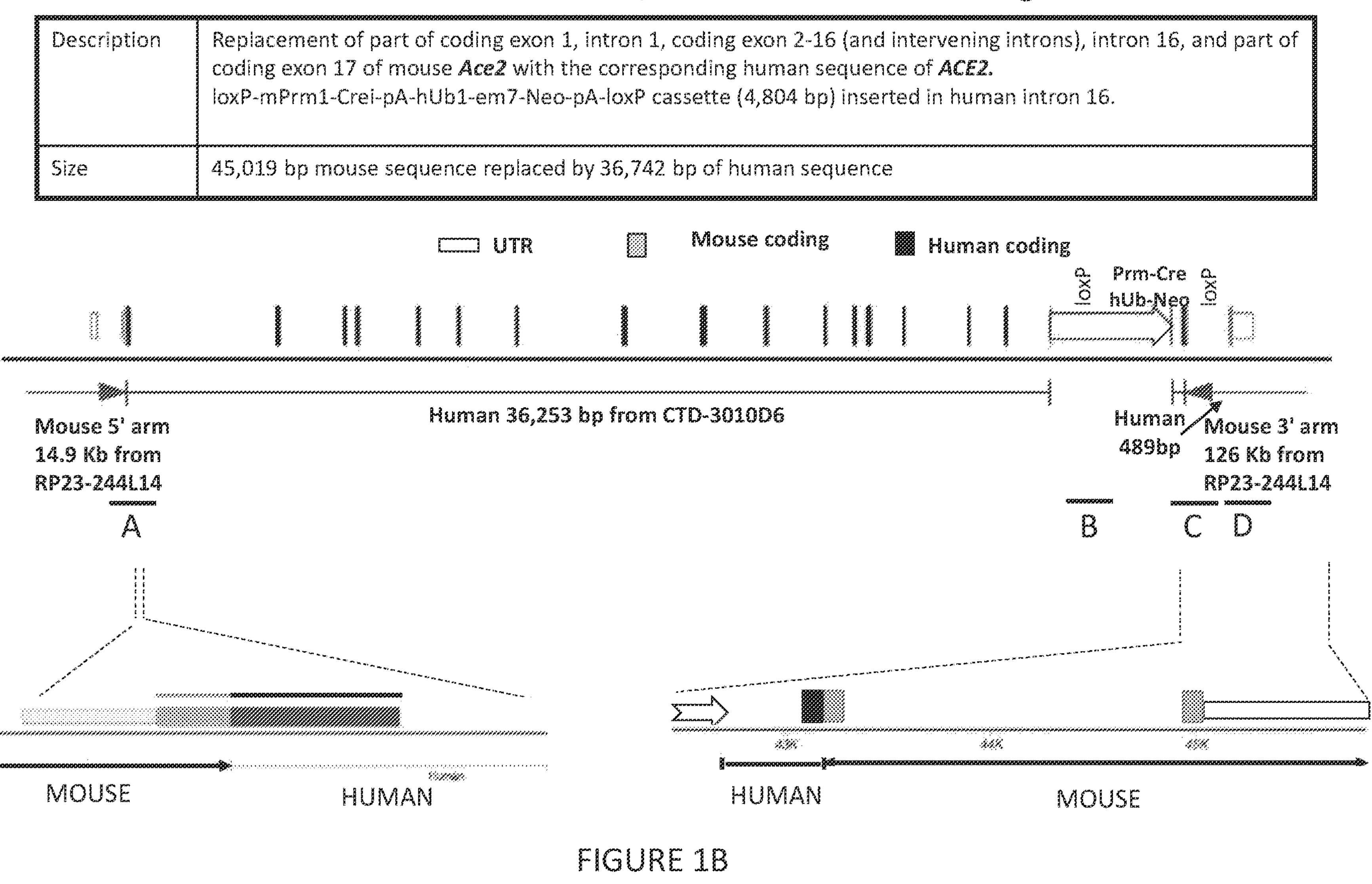
FIG. 1B shows a schematic (not-to-scale) of a humanized ACE2 allele (7878 allele) containing a neomycin resistance self-deleting cassette, which is depicted as the unfilled arrow. The mouse exonic sequences are indicated by the gray filled boxes, the human exonic sequences are indicated by the black filled boxes, and the mouse 5' and 3' untranslated regions (UTRs) are indicated by the white unfilled boxes. The sequences between the different mouse/human, human/cassette, cassette/human, and human/mouse junctions are indicated by the lines labeled A, B, C, and D, respectively, at the bottom of the figure. The sequences of these junctions are provided below in Table 1.

FIG. 1C shows a schematic (not-to-scale) of a cassette-deleted version of the humanized ACE2 allele in FIG. 1B. The mouse exonic sequences are indicated by the gray boxes, the human exons sequences are indicated by the black boxes, and the mouse 5' and 3' UTRs are indicated by the white boxes. The sequences between the different 5' mouse/human junction, the deleted loxP and cloning site, and 3' human/mouse junction are indicated by the lines labeled A, E, and D, respectively, at the bottom of the figure. The sequences of these junctions are provided below in Table 2.

TABLE 2

| | |
|---|---|
| A. 5' mouse/<br>5' human | AAGATGTCCA GCTCCTCCTG GCTCCTTCTC<br>AGCCTTGTTG CTGTTACTAC TGCTCAGTCC/<br>ACCATTGAGG AACAGGCCAA GACATTTTTG<br>GACAAGTTTA ACCACGAAGC CGAAGACCTG<br>(SEQ ID NO: 18) |
| E. Human//<br>**XhoI**/(*loxP*)/<br>ICEUI//**NheI**//<br>Human | CATTTATACA TTTCCACACT TACAACTCAA<br>TTTTCCAATG GAGCTGTTGA TGAACCTAAT/<br>**CTCGAG**/<br>*ATAACTTCGTATAATGTATGCTATACGAAGTTAT*<br>GCTAGG TAACTATAACGGTCCTAAGGTAGCGA |

TABLE 2-continued

| | |
|---|---|
| | **GCTAGC** CTAGGTTGCA AGGCATGAAA GATGCATAAT TGTCAAAGAC TTATATCTTT AATTAGACCT AT (SEQ ID NO: 23) |
| D. 3' human/ 3' mouse | AGCCTAGAGT TTCTGGGGAT ACAGCCAACA CTTGGACCTC CTAACCAGCC CCCTGTTTCC/ ATATGGCTGA TTATTTTTGG TGTTGTGATG GCACTGGTAG TGGTTGGCAT CATCATCCTG (SEQ ID NO: 21) |

Figure 2A:
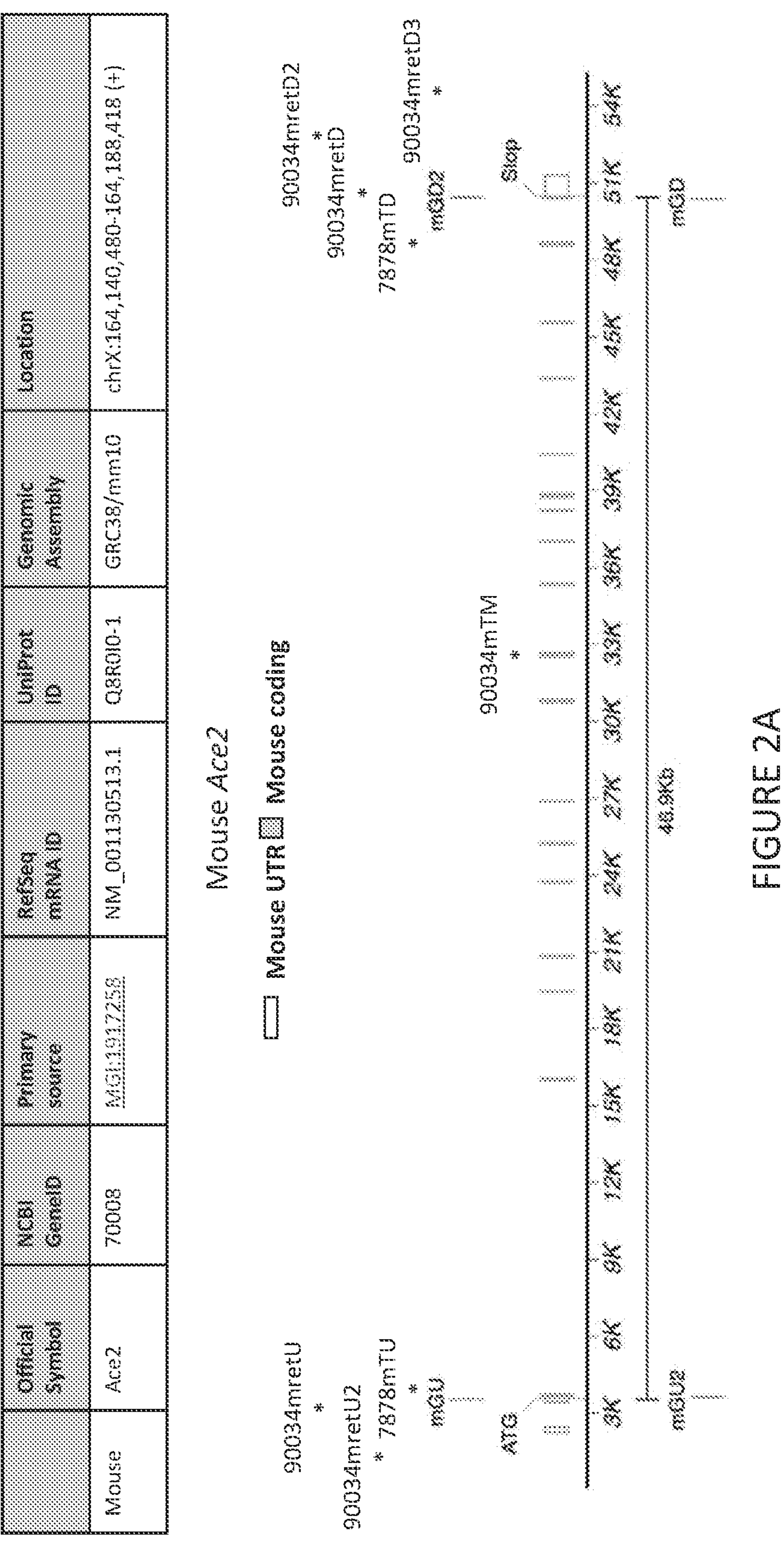

FIG. 2A shows a schematic (not-to-scale) of the mouse ACE2 locus. Untranslated and coding exons are represented by rectangles, and coding sequences are indicated by the filled boxes, the untranslated regions (UTRs) are indicated by the unfilled boxes, and various accession numbers for non-limiting examples of a mouse ACE2 gene, along with the chromosomal locations, are indicated at the top of the figure. The asterisks indicate the locations of (A) upstream (7878mTU) and downstream (7878mTD) primers for the loss-of-allele assay and (B) upstream (90034metU and 90034metU2) and downstream (90034metD, 90034metD2, 90034metD3, and 90034metD4) primers for a retention assay. Also shown are the locations targeted by guide RNAs (mGU, mGU2, mGD, and mGD2) used to collapse the ACE2 gene and create a null allele (ACE2-null) shown in FIG. 2B.

FIG. 2B shows a schematic (not-to-scale) of a mouse ACE2-null allele. The remaining coding sequence is indicated by the filled box, the untranslated regions (UTRs) are indicated by the unfilled boxes and a C to T point mutation in the 3'UTR is also depicted.

FIG. 3 shows an alignment of the mouse ACE2 protein (mACE2; SEQ ID NO:2), the human ACE2 protein (hACE2; SEQ ID NO:4), and the humanized mouse ACE2 protein (7878 final prot; SEQ ID NO:24). The dotted line above the alignment denotes the signal peptide (amino acids 1-17 of SEQ ID NO:24). The underscored residues are those encoded by the introduced human sequences (amino acids 20-740 of SEQ ID NO:24). The boxed residues constitute the transmembrane domain of the humanized mouse ACE2 protein (amino acids 741-761 of SEQ ID NO:24).

Figure 4:
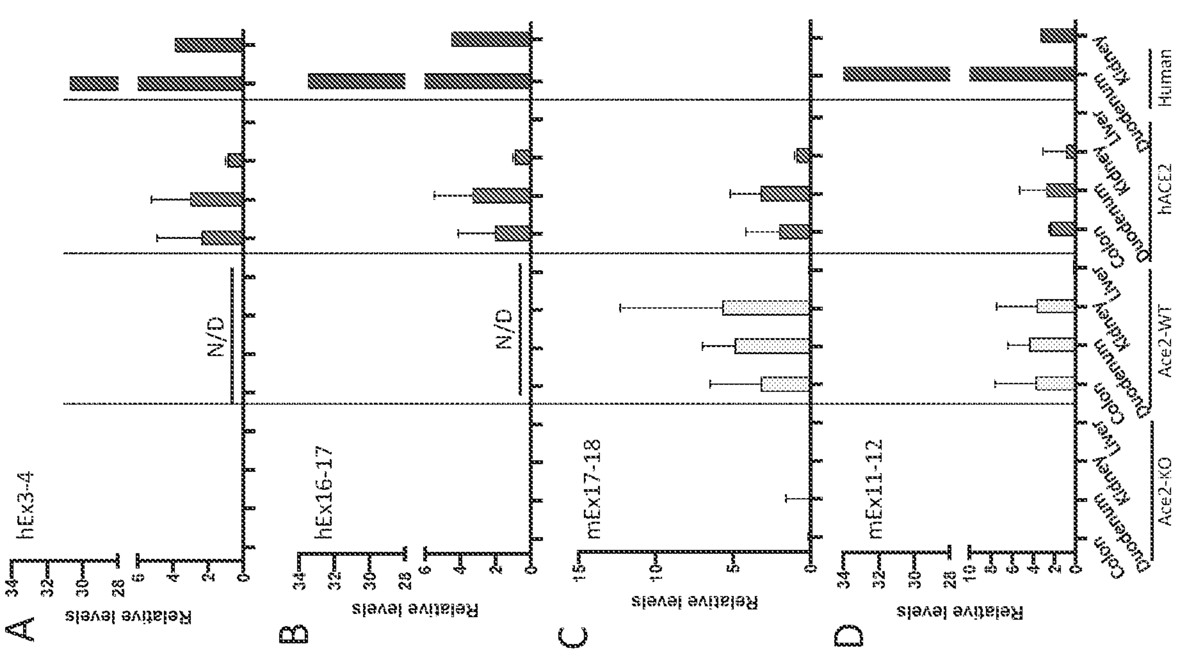

FIG. 4 provides relative levels (y-axis) of mRNA transcripts isolated from the colon, duodenum, kidney, or liver isolated from mice comprising a knockout of ACE2 (ACE2-KO), wildtype mice (ACE2-WT), mice comprising an endogenous ACE2 locus modified to encode a humanized ACE2 protein (hACE2), or human.

Figure 5:
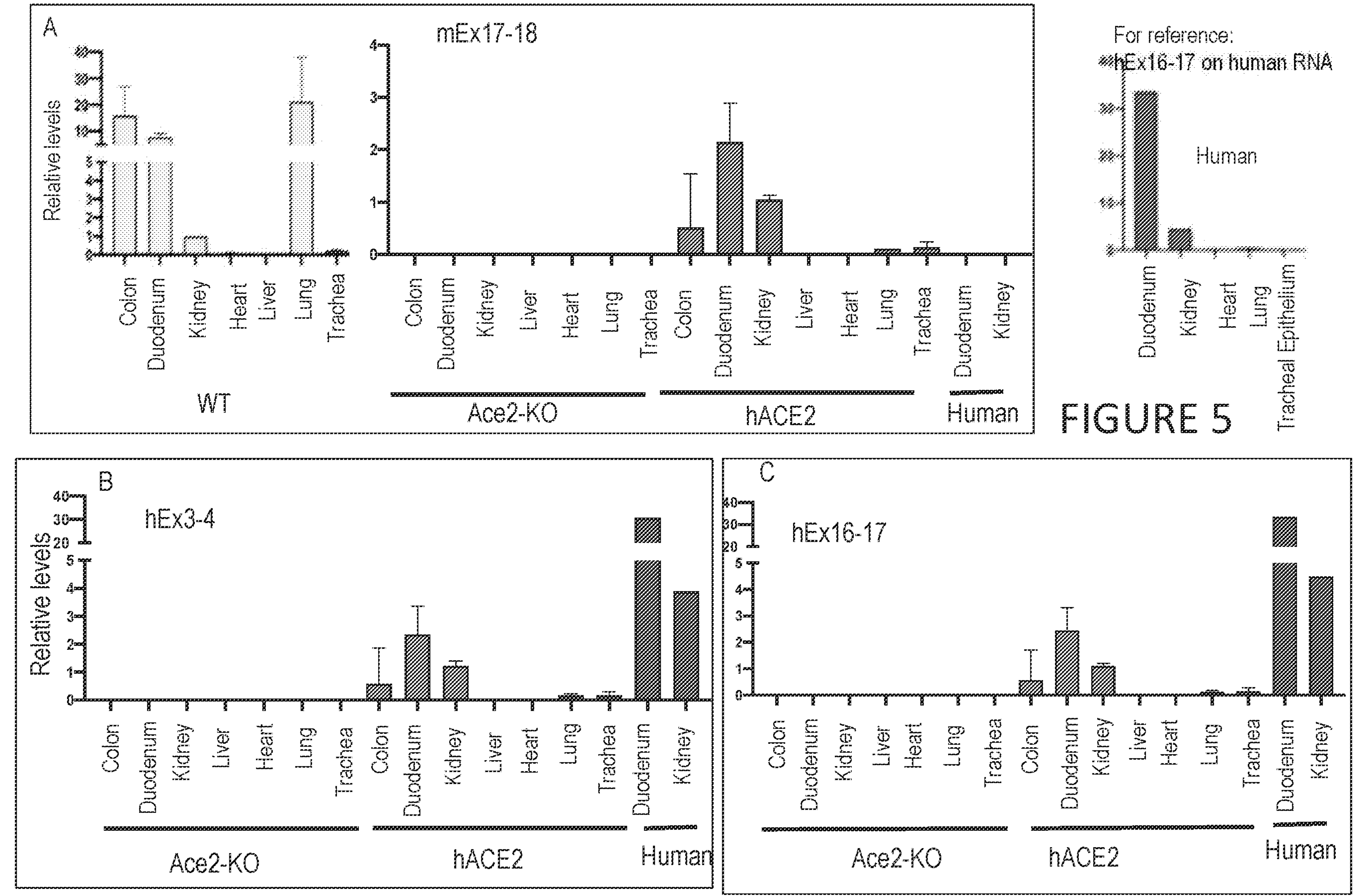

FIG. 5 provides relative levels (y-axis) of mRNA transcripts isolated from colon, duodenum, kidney, liver, heart, lung, or trachea isolated from mice comprising a knockout of ACE2 (ACE2-KO), wildtype mice (ACE2-WT), mice comprising an endogenous ACE2 locus modified to encode a humanized ACE2 protein (hACE2), or human.

Figure 6:
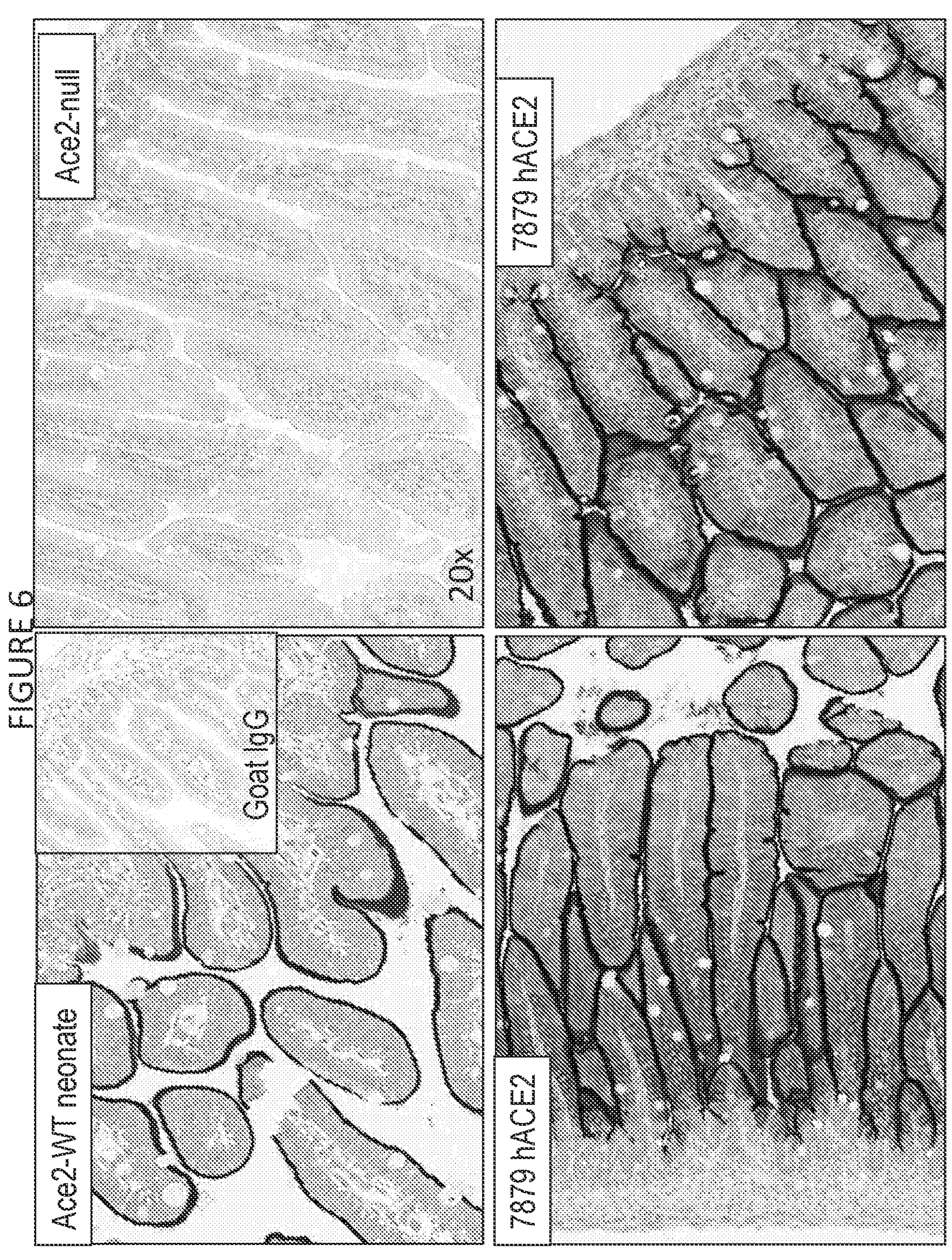

FIG. 6 provides immunohistochemistry images of duodenum (i) isolated from a neonate wild-type mouse (ACE2-WT neonate mouse 6), a mouse comprising a knockout of ACE2 (ACE2-null), and two mice comprising an endogenous ACE2 locus modified to express a humanized ACE2 protein (7879 hACE2 Mouse) and (ii) stained with ACE2 antibodies that recognize mouse and human ACE2. Magnification is at 20×.

Figure 7:
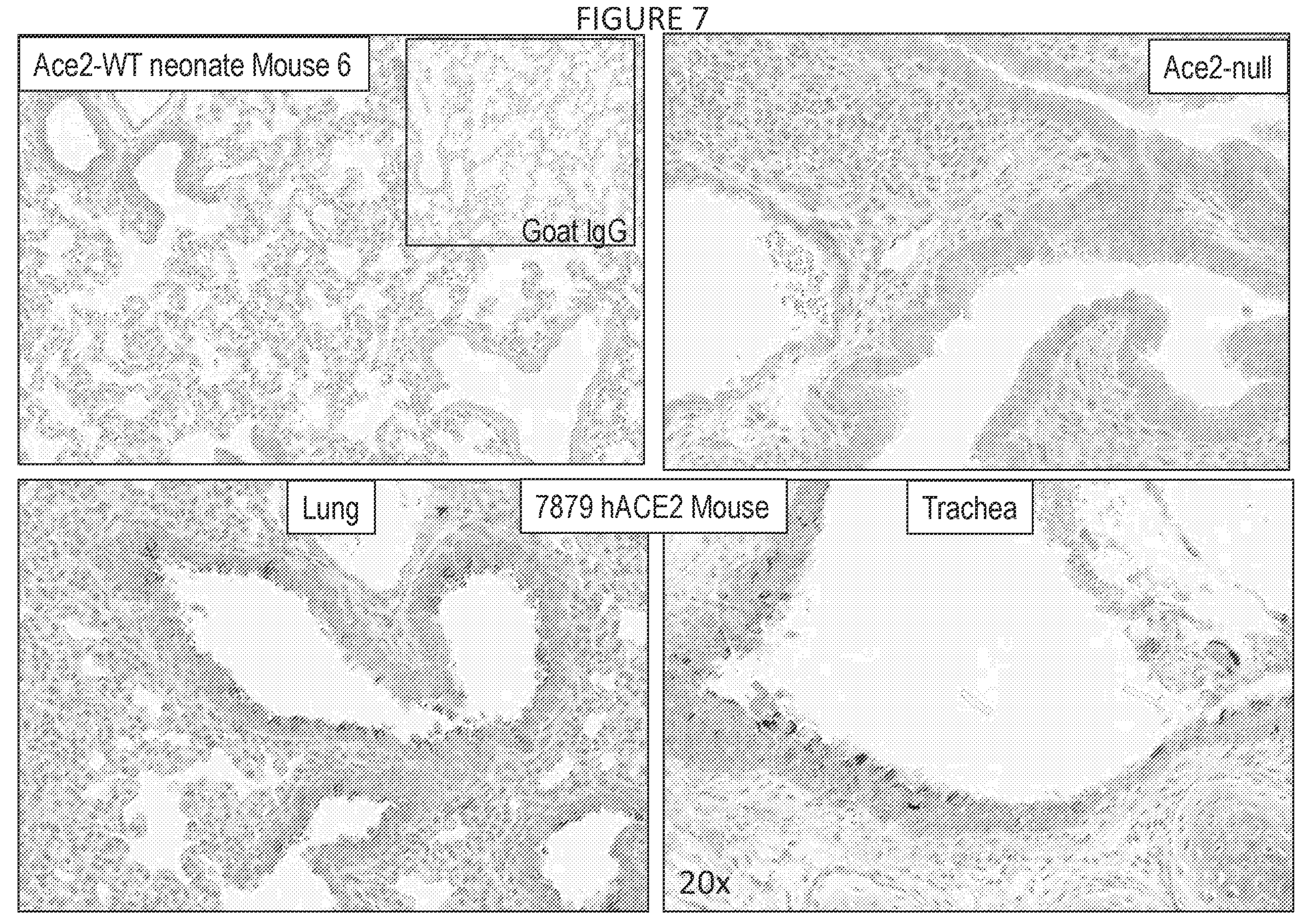

FIG. 7 provides immunohistochemistry images of lung or trachea (i) isolated from a neonate wild-type mouse (ACE2-WT neonate mouse 6), a mouse comprising a knockout of ACE2 (ACE2-null), and a mouse comprising an endogenous ACE2 locus modified to express a humanized ACE2 protein (7879 hACE2 Mouse) and (ii) stained with ACE2 antibodies that recognize mouse and human ACE2. Magnification is at 20×.

FIG. 8 provides the percent starting weight (y-axis) of mice comprising an endogenous ACE2 locus modified to express a humanized ACE2 protein and inoculated on day 0 with PBS (control), $10^2$ PFU of SARS-CoV-2 isolate, WA1, $10^3$ PFU of SARS-CoV-2 isolate, WA1, $10^4$ PFU of SARS-CoV-2 isolate, WA1, or $10^5$ PFU of SARS-CoV-2 isolate, WA1 over 8 days (x-axis).

Figure 9:
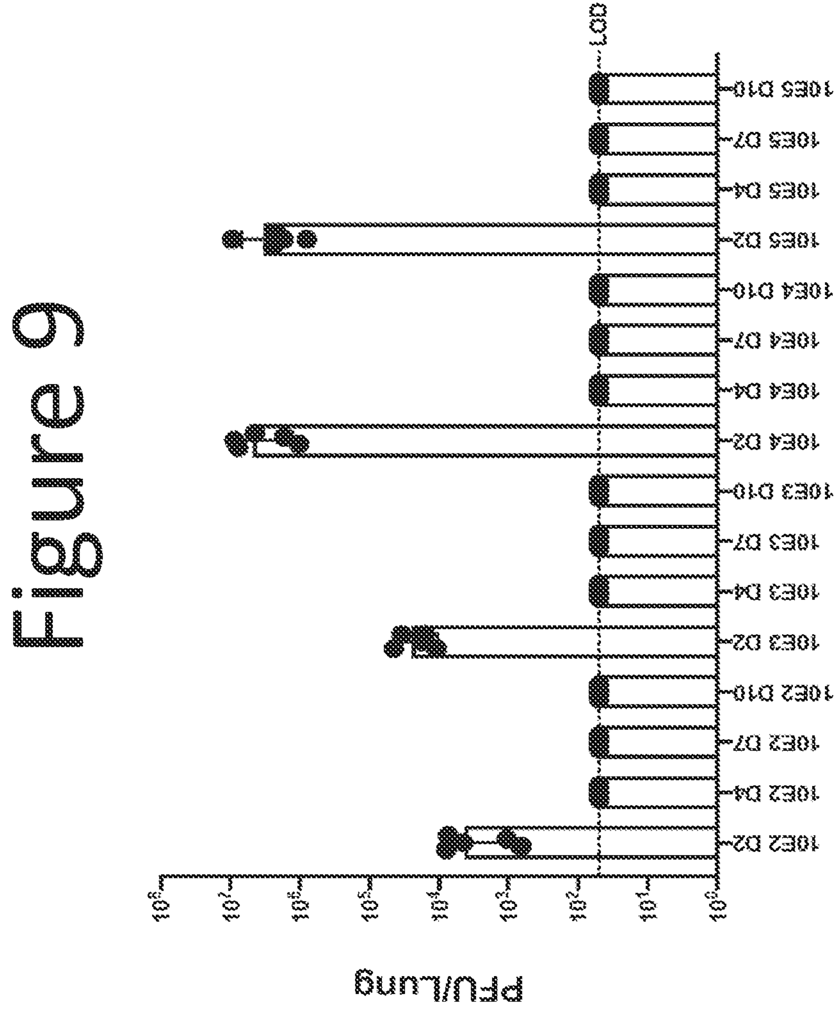

FIG. 9 provides plaque forming units (PFU) per lung isolated from mice comprising an endogenous ACE2 locus modified to express a humanized ACE2 protein and infected with varying doses of SARS-CoV-2 (10E2, 10E3, 10E4, or 10E5; x-axis) 2 days (D2), 4 days (D4), or 7 days (D7) after infection.

Figure 10:
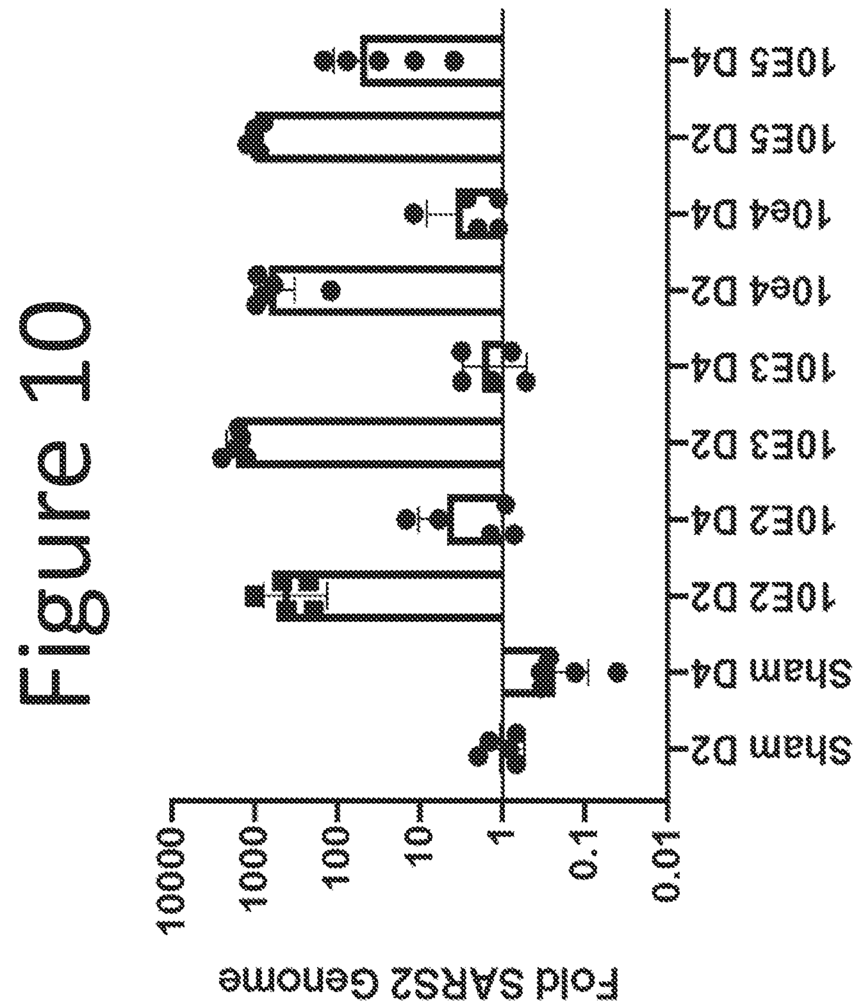

FIG. 10 provides the level of subgenomic SARS-CoV-2 expression (Fold SARS2 Genome; y-axis) found in the lungs isolated from control mice (Sham) or mice from mice comprising an endogenous ACE2 locus modified to express a humanized ACE2 protein and infected with varying doses of SARS-CoV-2 (10E2, 10E3, 10E4, or 10E5; x-axis) 2 days (D2) or 4 days (D4) after infection.

Figure 11:
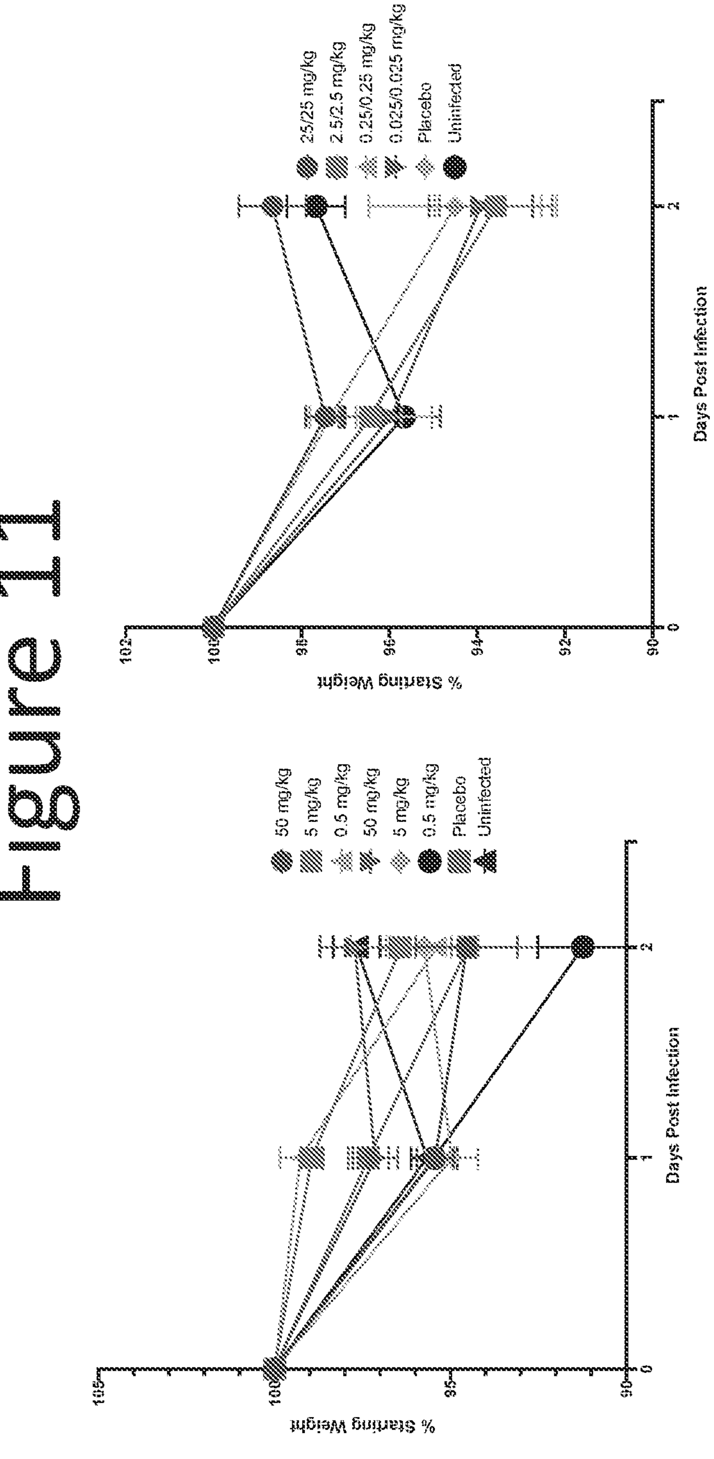

FIG. 11 provides the percent starting weight (y-axis) of mice comprising an endogenous ACE2 locus modified to express a humanized ACE2 protein and prophylactically treated with a placebo, with 50 mg/kg, 5 mg/kg, or 0.5 mg/kg of a single anti-spike protein antibody (left panel) or with a combination of 25/25 mg/kg, 2.5/2.5 mg/kg, or 0.5/0.5 mg/kg of two anti-spike protein antibodies (right panel) 2 days before inoculation on day 0 with $10^5$ PFU SARS-CoV-2 isolate.

Figure 12:
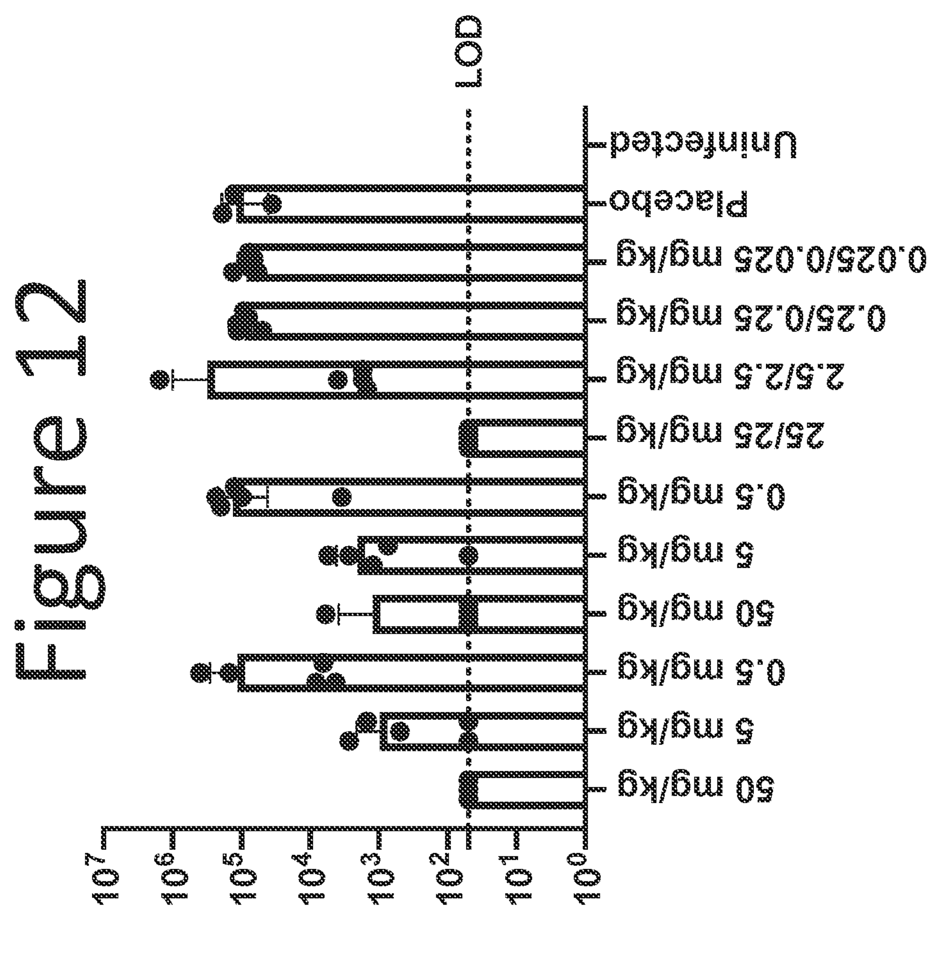
Figure 13:
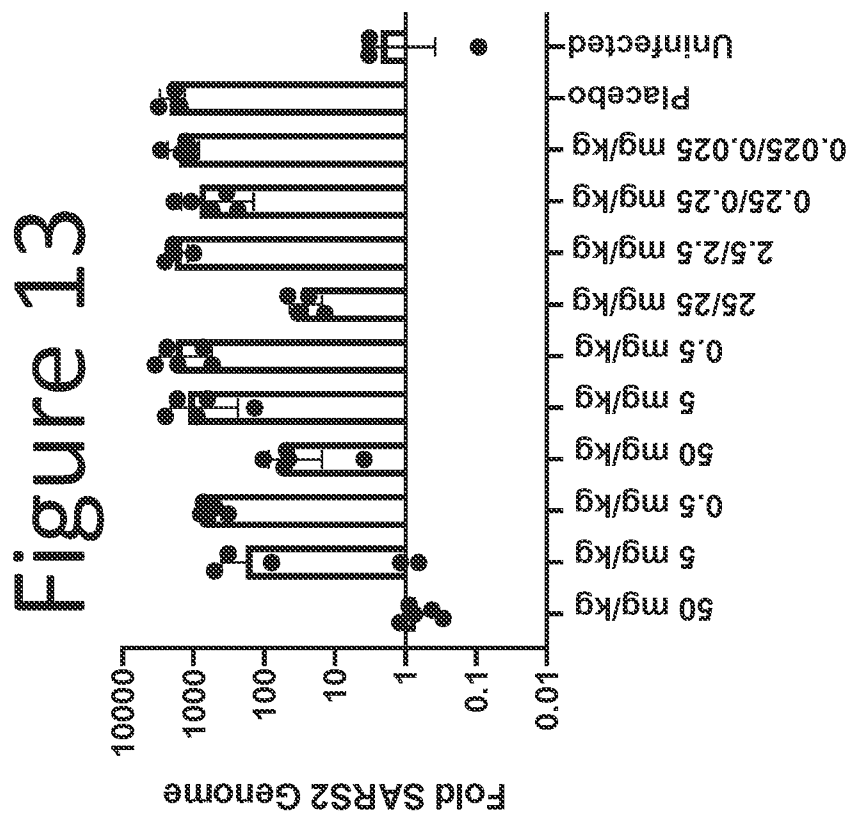

FIG. 12 provides plaque forming units (PFU) per lung isolated from mice comprising an endogenous ACE2 locus modified to express a humanized ACE2 protein and prophylactically treated with a placebo, with 50 mg/kg, 5 mg/kg, or 0.5 mg/kg of a single anti-spike protein antibody or with a combination of 25/25 mg/kg, 2.5/2.5 mg/kg, or 0.5/0.5 mg/kg of two anti-spike protein antibodies 2 days before inoculation with $10^5$ PFU SARS-CoV-2 isolate. Lungs were isolated 2 days after inoculation. LOD=limits of detection FIG. 13 provides the level of subgenomic SARS-CoV-2 expression (Fold SARS2 Genome; y-axis) found in the lungs isolated from mice comprising an endogenous ACE2 locus modified to express a humanized ACE2 protein and prophylactically treated with a placebo, with 50 mg/kg, 5 mg/kg, or 0.5 mg/kg of a single anti-spike protein antibody or with a combination of 25/25 mg/kg, 2.5/2.5 mg/kg, or 0.5/0.5 mg/kg of two anti-spike protein antibodies 2 days before inoculation with $10^5$ PFU SARS-CoV-2 isolate. Lungs were isolated 2 days after inoculation.

Figure 14:
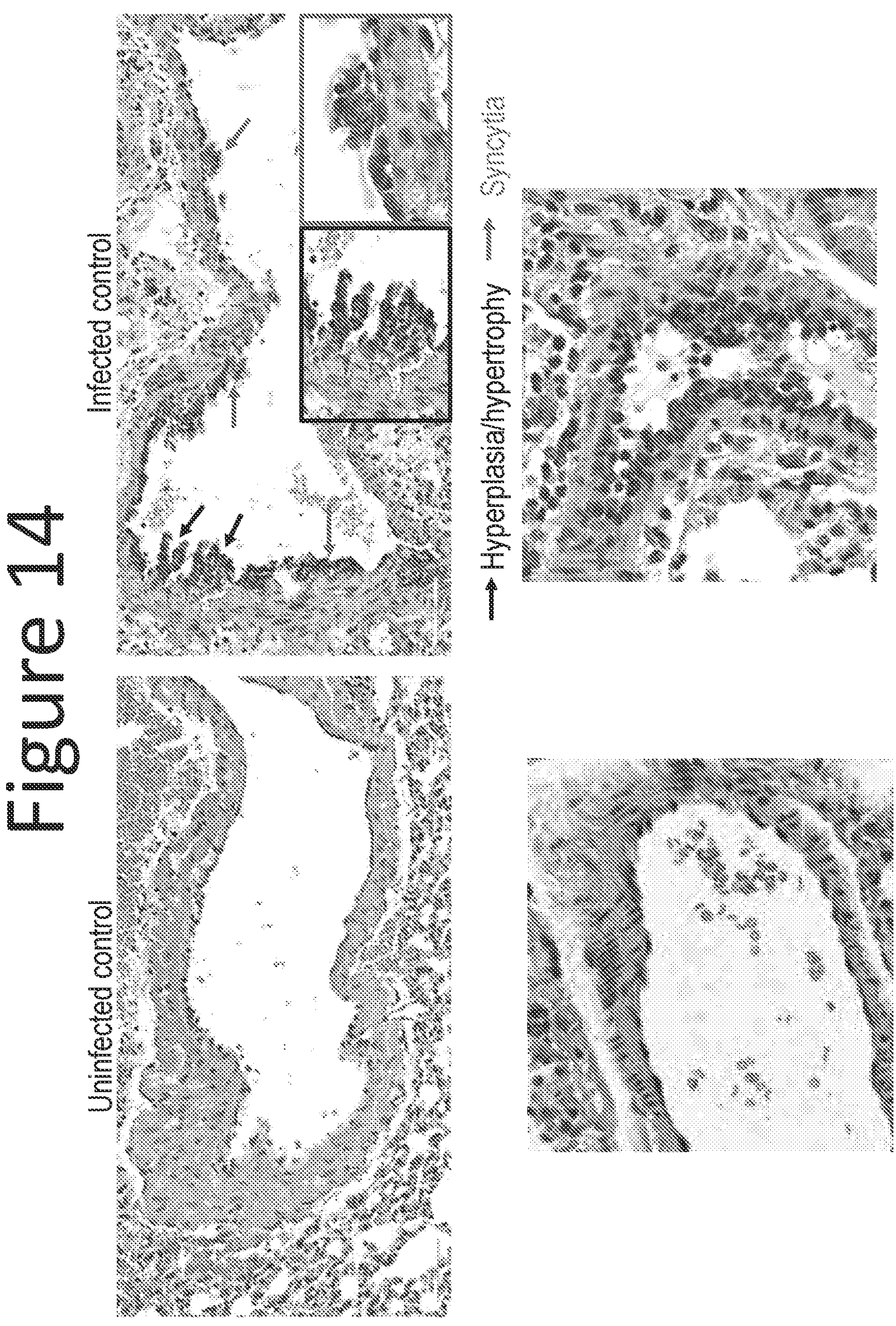

FIG. 14 presents representative H&E images of blood vessel of the lungs of mice comprising an endogenous ACE2 locus modified to express a humanized ACE2 protein that were either uninfected (left) or infected with SARS-CoV-2 (right). Vascular lesions in the infected lungs include endothelial hyperplasia/hypertrophy, endothelial syncytia, and endothelialitis. Magnification is at 40×.

FIG. 15 provides the pathology score (left panel) or plaque forming units (PFU) per lung (right panel) of mice comprising an endogenous ACE2 locus modified to express a humanized ACE2 protein and prophylactically treated with a placebo, with 50 mg/kg, 5 mg/kg, or 0.5 mg/kg of a single anti-spike protein antibody or with a combination of 25/25 mg/kg, 2.5/2.5 mg/kg, or 0.5/0.5 mg/kg of two anti-spike protein antibodies 2 days before inoculation with $10^5$ PFU SARS-CoV-2 isolate. Lungs were isolated 2 days after inoculation.

DESCRIPTION

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell and is capable of being inherited by progeny thereof. Any protocol may be used for the stable incorporation of a nucleic acid into the genome of a cell.

The term "targeting vector" refers to a recombinant nucleic acid that can be introduced by homologous recombination, non-homologous-end-joining-mediated ligation, or any other means of recombination to a target position in the genome of a cell.

The term "wild-type" includes entities having a structure and/or activity as found in a normal (as contrasted with mutant, diseased, altered, or so forth) state or context. Wild-type genes and polypeptides often exist in multiple different forms (e.g., alleles).

The term "endogenous" refers to a nucleic acid sequence that occurs naturally within a cell or non-human animal. For example, an endogenous ACE2 sequence of a non-human animal refers to a native ACE2 sequence that naturally occurs at the ACE2 locus in the non-human animal.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two portions that do not naturally occur together in the same molecule. For example, the term "heterologous," when used with reference to portions of a nucleic acid or portions of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a prokaryotic protein (i.e., a protein naturally expressed in a prokaryotic cell) can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) Nucleic Acids Research 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, an "ACE2 locus" may refer to the specific location of an ACE2 gene, ACE2 DNA sequence, ACE2-encoding sequence, or ACE2 position on a chromosome of the genome of an organism that has been identified as to where such a sequence resides. An "ACE2 locus" may comprise a regulatory element of an ACE2 gene, including, for example, an enhancer, a promoter, 5' and/or 3' untranslated region (UTR), or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

| | | | | | |
|---|---|---|---|---|---|
| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

The term "reporter gene" refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyltransferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreenl), yellow fluorescent proteins (e.g., YFP, eYFP, Citrine, Venus, YPet, PhiYFP, and ZsYellowl), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyanl, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

The term "recombination" includes any process of exchange of genetic information between two polynucleotides and can occur by any mechanism. Recombination in response to double-strand breaks (DSBs) occurs principally through two conserved DNA repair pathways: non-homologous end joining (NHEJ) and homologous recombination (HR). See Kasparek & Humphrey (2011) Seminars in Cell & Dev. Biol. 22:886-897, herein incorporated by reference in its entirety for all purposes. Likewise, repair of a target nucleic acid mediated by an exogenous donor nucleic acid can include any process of exchange of genetic information between the two polynucleotides.

NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to HDR, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) Genome Res. 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Recombination can also occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) Cell 153:910-918; Mandalos et al. (2012) PLOS ONE 7:e45768:1-9; and Wang et al. (2013) Nat Biotechnol. 31:530-532, each of which is herein incorporated by reference in its entirety for all purposes.

The term "antigen-binding protein" includes any protein that binds to an antigen. Examples of antigen-binding proteins include an antibody, an antigen-binding fragment of an antibody, a multispecific antibody (e.g., a bi-specific antibody), an scFV, a bis-scFV, a diabody, a triabody, a tetrabody, a V-NAR, a VHH, a VL, a F(ab), a F(ab)2, a DVD (dual variable domain antigen-binding protein), an SVD (single variable domain antigen-binding protein), a bispecific T-cell engager (BiTE), or a Davisbody (U.S. Pat. No. 8,586,713, herein incorporated by reference herein in its entirety for all purposes).

The term "multi-specific" or "bi-specific" with reference to an antigen-binding protein means that the protein recognizes different epitopes, either on the same antigen or on different antigens. A multi-specific antigen-binding protein can be a single multifunctional polypeptide, or it can be a multimeric complex of two or more polypeptides that are covalently or non-covalently associated with one another. For example, an antibody or fragment thereof can be functionally linked (e.g., by chemical coupling, genetic fusion, non-covalent association or otherwise) to one or more other molecular entities, such as a protein or fragment thereof to produce a bi-specific or a multi-specific antigen-binding molecule with a second binding specificity.

The term "antigen" refers to a substance, whether an entire molecule or a domain within a molecule, which is capable of eliciting production of antibodies with binding specificity to that substance. The term antigen also includes substances, which in wild-type host organisms would not elicit antibody production by virtue of self-recognition, but can elicit such a response in a host animal with appropriate genetic engineering to break immunological tolerance.

The term "epitope" refers to a site on an antigen to which an antigen-binding protein (e.g., antibody) binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996), herein incorporated by reference in its entirety for all purposes.

An "antibody paratope" as described herein generally comprises at a minimum a complementarity determining region (CDR) that specifically recognizes the heterologous epitope (e.g., a CDR3 region of a heavy and/or light chain variable domain).

The term "antibody" includes immunoglobulin molecules comprising four polypeptide chains, two heavy (H) chains and two light (L) chains inter-connected by disulfide bonds. Each heavy chain comprises a heavy chain variable domain and a heavy chain constant region (CH). The heavy chain constant region comprises three domains: CH1, CH2 and CH3. Each light chain comprises a light chain variable domain and a light chain constant region (CL). The heavy chain and light chain variable domains can be further subdivided into regions of hypervariability, termed complementarity determining regions (CDR), interspersed with regions that are more conserved, termed framework regions (FR). Each heavy and light chain variable domain comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3). The term "high affinity" antibody refers to an antibody that has a KD with respect to its target epitope about of 10-9 M or lower (e.g., about 1×10-9 M, 1×10-10 M, 1×10-11 M, or about 1×10-12 M). In one embodiment, KD is measured by surface plasmon resonance, e.g., BIACORE™; in another embodiment, KD is measured by ELISA.

The term "bi-specific antibody" includes an antibody capable of selectively binding two or more epitopes. Bi-specific antibodies generally comprise two different heavy chains, with each heavy chain specifically binding a different epitope—either on two different molecules (e.g., on two different antigens) or on the same molecule (e.g., on the same antigen). If a bi-specific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bi-specific antibody can be on the same or a different target (e.g., on the same or a different protein). Bi-specific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain. A typical bi-specific antibody has two heavy chains each having three heavy chain CDRs, followed by (N-terminal to C-terminal) a CH1 domain, a hinge, a CH2 domain, and a CH3 domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes.

The term "heavy chain," or "immunoglobulin heavy chain" includes an immunoglobulin heavy chain sequence, including immunoglobulin heavy chain constant region sequence, from any organism. Heavy chain variable domains include three heavy chain CDRs and four FR regions, unless otherwise specified. Fragments of heavy chains include CDRs, CDRs and FRs, and combinations thereof. A typical heavy chain has, following the variable domain (from N-terminal to C-terminal), a CH1 domain, a hinge, a CH2 domain, and a CH3 domain. A functional fragment of a heavy chain includes a fragment that is capable of specifically recognizing an epitope (e.g., recognizing the epitope with a KD in the micromolar, nanomolar, or picomolar range), that is capable of expressing and secreting from a cell, and that comprises at least one CDR. Heavy chain variable domains are encoded by variable region nucleotide sequences, which generally comprise VH, DH, and JH segments derived from a repertoire of VH, DH, and JH segments present in the germline. Sequences, locations and nomenclature for V, D, and J heavy chain segments for various organisms can be found in IMGT database, which is accessible via the internet on the World Wide Web (www) at the URL "imgt.org."

The term "light chain" includes an immunoglobulin light chain sequence from any organism, and unless otherwise specified includes human kappa (κ) and lambda (λ) light chains and a VpreB, as well as surrogate light chains. Light chain variable domains typically include three light chain CDRs and four framework (FR) regions, unless otherwise specified. Generally, a full-length light chain includes, from amino terminus to carboxyl terminus, a variable domain that includes FR1-CDR1-FR2-CDR2-FR3-CDR3-FR4, and a light chain constant region amino acid sequence. Light chain variable domains are encoded by light chain variable region nucleotide sequences, which generally comprise light chain VL and light chain JL gene segments, derived from a repertoire of light chain V and J gene segments present in the germline. Sequences, locations and nomenclature for light chain V and J gene segments for various organisms can be found in IMGT database, which is accessible via the internet on the World Wide Web (www) at the URL "imgt.org." Light chains include those, e.g., that do not selectively bind either a first or a second epitope selectively bound by the epitope-binding protein in which they appear. Light chains also include those that bind and recognize, or assist the heavy chain with binding and recognizing, one or more epitopes selectively bound by the epitope-binding protein in which they appear.

The term "complementary determining region" or "CDR," as used herein, includes an amino acid sequence encoded by a nucleic acid sequence of an organism's immunoglobulin genes that normally (i.e., in a wild-type animal) appears between two framework regions in a variable region of a light or a heavy chain of an immunoglobulin molecule (e.g., an antibody or a T cell receptor). A CDR can be encoded by, for example, a germline sequence or a rearranged sequence, and, for example, by a naïve or a mature B cell or a T cell. A CDR can be somatically mutated (e.g., vary from a sequence encoded in an animal's germline), humanized, and/or modified with amino acid substitutions, additions, or deletions. In some circumstances (e.g., for a CDR3), CDRs can be encoded by two or more sequences (e.g., germline sequences) that are not contiguous (e.g., in an unrearranged nucleic acid sequence) but are contiguous in a B cell nucleic acid sequence, e.g., as a result of splicing or connecting the sequences (e.g., V-D-J recombination to form a heavy chain CDR3.

Specific binding of an antigen-binding protein to its target antigen includes binding with an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas non-specific binding is usually the result of van der Waals forces. Specific binding does not however necessarily imply that an antigen-binding protein binds one and only one target.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means $p<0.05$.

I. OVERVIEW

Disclosed herein are non-human animal cells and non-human animals comprising a humanized ACE2 locus and methods of using such non-human animal cells and non-human animals. Non-human animal cells or non-human animals comprising a humanized ACE2 locus express a human ACE2 protein or a chimeric (e.g., humanized) ACE2 protein comprising one or more fragments of a human ACE2 protein (e.g., all or part of the human ACE2 extracellular domain). Ligands binding human ACE2 often will not bind to orthologous non-human animal ACE2 proteins such as mouse ACE2 due to the sequence differences between human ACE2 and the non-human animal ACE2. For example, coronaviruses that infect cells expressing human ACE2 will often not recognize rodent ACE2. (Subbarao and Roberts (2006) *TRENDS Microbiol.* 14:299-303; McCray et al. (2007) *J. Virol.* 81:813-821; Wan (2020) *J. Virol.* 94:1-9; Sun et al. (2020) *Cell Host & Microbe* 28:1-10) Because of this, the progression of human-ACE2-mediated coronavirus infection or therapy thereof cannot be effectively assessed in wild-type non-human animals with unmodified endogenous (i.e., native) ACE2 loci.

As a binding partner for coronavirus, e.g., SARS-CoV-2, non-human animals expressing human or humanized ACE2 can be utilized for studying SARS-CoV-2 infection and associated diseases, e.g., COVID-19, and for determining the efficacy of therapies thereto. For example, in early 2020, efforts to identify effective measures against COVID-19 were in full swing.

II. NON-HUMAN ANIMALS COMPRISING A HUMANIZED ACE2 LOCUS

The cells and non-human animals disclosed herein comprise a humanized ACE2 locus. Cells or non-human animals comprising a humanized ACE2 locus express a human ACE2 protein or a partially humanized, chimeric ACE2 protein in which one or more fragments of the native ACE2 protein have been replaced with corresponding fragments from human ACE2 (e.g., all or part of the extracellular domain).

A. Angiotensin-Converting Enzyme 2 (ACE2)

The cells and non-human animals described herein comprise a humanized ACE2 locus. Angiotensin-converting enzyme 2 (ACE2; ACEH) is encoded by the ACE2 gene. ACE2 is part of the angiotensin-converting enzyme family of dipeptidyl carboxydipeptidases and has considerable homology to human angiotensin 1 converting enzyme. ACE2 is a cell surface expressed aminopeptidase that catalyzes the cleavage of angiotensin I into angiotensin 1-9, and angiotensin II into the vasodilator angiotensin 1-7. The organ- and cell-specific expression of this gene suggests that it may play a role in the regulation of cardiovascular and renal function, as well as fertility. In addition, the encoded protein is a functional receptor for the spike glycoprotein of the human coronavirus HCoV-NL63 and the human severe acute respiratory syndrome coronaviruses, SARS-CoV and SARS-CoV-2 (COVID-19 virus)).

Both the human and mouse ACE2 genes are located on chromosome X, and each comprises 19 untranslated and coding exons of which 18 contain coding sequences. Coding exon numbering used throughout excludes the 5' non-coding exon. Accordingly, "coding exon 1" refers to the first exon comprising coding sequences and subsequent coding exons are numbered accordingly. As such, and in connection with coding exons, the first intron following coding exon 1 may be referred to herein as intron 1.

An exemplary coding sequence for human ACE2 is assigned NCBI Accession Number NM_021804.3. An exemplary coding sequence for mouse ACE2 is assigned NCBI Accession Number NM_001130513.1. An exemplary human ACE2 protein is assigned UniProt Accession No. Q9BYF1-1. An exemplary mouse ACE2 protein is assigned UniProt Accession No. Q8R0I0-1. An exemplary humanized human/mouse ACE2 protein is set forth in SEQ ID NO:24, which comprises in operable linkage a mouse ACE2 signal peptide (SEQ ID NO:26), a human ACE2 extracellular domain (SEQ ID NO:27), a mouse ACE2 transmembrane domain (SEQ ID NO:28), and a mouse ACE2 cytoplasmic domain (SEQ ID NO:28).

B. Humanized ACE2 Loci

A humanized ACE2 locus can be an ACE2 locus in which the entire ACE2 gene is replaced with the corresponding orthologous human ACE2 sequence, or it can be an ACE2 locus in which only a portion of the ACE2 gene is replaced with the corresponding orthologous human ACE2 sequence (i.e., humanized). Optionally, the corresponding orthologous human ACE2 sequence is modified to be codon-optimized based on codon usage in the non-human animal. Replaced (i.e., humanized) regions can include coding regions such as an exon, non-coding regions such as an intron, an untranslated region, or a regulatory region (e.g., a promoter, an enhancer, or a transcriptional repressor-binding element), or any combination thereof. As one example, exons corresponding to 1, 2, 3, 4, 5, 6, 7, 8, 9, 10, 11, 12, 13, 14, 15, 16, 17, 18, or all 19 exons of the ACE2 gene are humanized. Likewise, introns corresponding to 1, 2, 3, 4, 5, 6, 7, 8, 9, 10, 11, 12, 13, 14, 15, 16, 16, or all 18 introns of the human ACE2 gene can be humanized. For example, the coding region of a non-human (e.g., rodent, e.g., rat or mouse) ACE2 gene could be replaced with the corresponding orthologous human ACE2 region. Alternatively, a region of ACE2 encoding an extracellular domain may be humanized. For example, at a non-human animal endogenous ACE2 locus, coding sequences starting in exon 2 (also referred to as coding exon 1) (e.g., after an endogenous ACE2 signal peptide coding region) to exon 18 (also referred to herein as coding exon 17) (e.g., up to an endogenous transmembrane domain coding region) may be replaced with corresponding human ACE2 coding sequences. Likewise, endogenous non-human ACE2 introns corresponding to coding introns 1, 2, 3, 4, 5, 6, 7, 8, 9, 10, 11, 12, 13, 14, 15, and 16 of the human ACE2 can be humanized. Flanking untranslated regions including regulatory sequences can also be humanized. For example, the 5' untranslated region (UTR), the 3'UTR, or both the 5' UTR and the 3' UTR can be humanized, or the 5' UTR, the 3'UTR, or both the 5' UTR and the 3' UTR can remain endogenous. In one specific example, the 3' UTR is humanized, but the 5' UTR remains endogenous. Depending on the extent of replacement by orthologous sequences, regulatory sequences, such as a promoter, can be endogenous or supplied by the replacing human orthologous sequence. For example, the humanized ACE2 locus can include the endogenous non-human animal ACE2 promoter.

The ACE2 protein encoded by the humanized ACE2 locus can comprise one or more domains that are from a human ACE2 protein. The ACE2 protein encoded by the humanized ACE2 locus may also comprise one or more domains that are from the endogenous (i.e., native) non-human animal ACE2 protein. Domains from a human ACE2 protein can be encoded by a fully humanized sequence (i.e., the entire sequence encoding that domain is replaced with the orthologous human ACE2 sequence) or can be encoded by a partially humanized sequence (i.e., some of the sequence encoding that domain is replaced with the orthologous human ACE2 sequence, and the remaining endogenous (i.e., native) sequence encoding that domain encodes the same amino acids as the orthologous human ACE2 sequence such that the encoded domain is identical to that domain in the human ACE2 protein).

As one example, the ACE2 protein encoded by the humanized ACE2 locus can comprise a human ACE2 extracellular domain. Optionally, the human ACE2 extracellular domain comprises, consists essentially of, or consists of a sequence that is at least 85%, 90%, 95%, 96%, 97%, 98%, 99%, or 100% identical to SEQ ID NO:27 and the ACE2 protein retains the activity of an ACE2 protein (e.g., retains the ability to catalyze the cleavage of angiotensin I into angiotensin 1-9, and angiotensin II into the vasodilator angiotensin 1-7, permit coronavirus (e.g., SARS-CoV-2) infection, etc.). The ACE2 protein encoded by the humanized ACE2 locus may comprise an endogenous non-human animal ACE2 transmembrane domain (e.g., a mouse ACE2 transmembrane domain). Optionally, the non-human animal ACE2 transmembrane domain comprises, consists essentially of, or consists of a sequence that is at least 85%, 90%, 95%, 96%, 97%, 98%, 99%, or 100% identical to SEQ ID NO:28 and the ACE2 protein retains the activity of the native ACE2. For example, the ACE2 protein encoded by the humanized ACE2 locus can comprise, consist essentially of, or consist of a sequence that is at least 85%, 90%, 95%, 96%, 97%, 98%, 99%, or 100% identical to SEQ ID NO:29 and the ACE2 protein retains the activity of the native ACE2.

Optionally, a humanized ACE2 locus can comprise other elements. Examples of such elements can include selection cassettes, reporter genes, recombinase recognition sites, or other elements. Alternatively, the humanized ACE2 locus can lack other elements (e.g., can lack a selection marker or selection cassette). Examples of suitable reporter genes and reporter proteins are disclosed elsewhere herein. Examples of suitable selection markers include neomycin phosphotransferase ($neo_r$), hygromycin B phosphotransferase ($hyg_r$), puromycin-N-acetyltransferase ($puro_r$), blasticidin S deaminase ($bsr_r$), xanthine/guanine phosphoribosyl transferase (gpt), and herpes simplex virus thymidine kinase (HSV-k). Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

Other elements such as reporter genes or selection cassettes can be self-deleting cassettes flanked by recombinase recognition sites. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. The polynucleotide encoding the selection marker can be operably linked to a promoter active in a cell being targeted. Examples of promoters are described elsewhere herein. As another specific example, a self-deleting selection cassette can comprise a hygromycin resistance gene coding sequence operably linked to one or more promoters (e.g., both human ubiquitin and EM7 promoters) followed by a polyadenylation signal, followed by a Crei coding sequence operably linked to one or more promoters (e.g., an mPrm1 promoter), followed by another polyadenylation signal, wherein the entire cassette is flanked by loxP sites.

The humanized ACE2 locus can also be a conditional allele. For example, the conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in anti sense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

One exemplary humanized ACE2 locus (e.g., a humanized mouse ACE2 locus) is one in which part of the first coding exon through part of the 17th coding exon of the endogenous ACE2 gene are replaced with the corresponding human sequence. These exons encode the extracellular domain of ACE2. Optionally, the humanized sequence can be through the stop codon and 3' UTR, and optionally into the sequence just downstream of the 3' UTR. Optionally, a portion of the intron upstream of coding exon 1 is also humanized.

C. Non-Human Cells and Non-Human Animals Comprising a Humanized ACE2 Locus

Non-human animal cells and non-human animals comprising a humanized ACE2 locus as described elsewhere herein are provided. The cells or non-human animals can be heterozygous or homozygous for the humanized ACE2 locus. A diploid organism has two alleles at each genetic locus. Each pair of alleles represents the genotype of a specific genetic locus. Genotypes are described as homozygous if there are two identical alleles at a particular locus and as heterozygous if the two alleles differ.

The non-human animal cells provided herein can be, for example, any non-human cell comprising an ACE2 locus or a genomic locus homologous or orthologous to the human ACE2 locus. The cells can be eukaryotic cells, which include, for example, fungal cells (e.g., yeast), plant cells, animal cells, mammalian cells, non-human mammalian cells, and human cells. The term “animal” includes mammals, fishes, and birds. A mammalian cell can be, for example, a non-human mammalian cell, a rodent cell, a rat cell, a mouse cell, or a hamster cell. Other non-human mammals include, for example, non-human primates, monkeys, apes, orangutans, cats, dogs, rabbits, horses, bulls, deer, bison, livestock (e.g., bovine species such as cows, steer, and so forth; ovine species such as sheep, goats, and so forth; and porcine species such as pigs and boars). Birds include, for example, chickens, turkeys, ostrich, geese, ducks, and so forth. Domesticated animals and agricultural animals are also included. The term “non-human” excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be liver cells, such as hepatoblasts or hepatocytes.

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, hepatocytes.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. A specific example of an immortalized cell line is the HepG2 human liver cancer cell line. Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

Non-human animals comprising a humanized ACE2 locus as described herein can be made by the methods described elsewhere herein. The term "animal" includes mammals, fishes, and birds. Non-human mammals include, for example, non-human primates, monkeys, apes, orangutans, cats, dogs, horses, bulls, deer, bison, sheep, rabbits, rodents (e.g., mice, rats, hamsters, and guinea pigs), and livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 12951/SV, 12951/Svlm), 129S2, 129S4, 129S5, 129S9/SvEvH, 129S6 (129/SvEvTac), 129S7, 129S8, 129T1, and 129T2. See, e.g., Festing et al. (1999) *Mammalian Genome* 10:836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/Ola. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. Some suitable rats can be from an inbred rat strain. See, e.g., US 2014/0235933, herein incorporated by reference in its entirety for all purposes.

In some embodiments, a non-human animal comprising a genetically modified endogenous ACE2 locus as described herein expresses a recombinant ACE2 protein in an organ selected from the group consisting of colon, duodenum, kidney, heart, liver, lung, trachea, and any combination thereof. In some embodiments, the expression pattern of a recombinant ACE2 protein in a genetically modified non-human animal as described herein follows the expression pattern of a non-human animal ACE2 protein in a control non-human animal comprising a wildtype endogenous ACE2 locus.

In some embodiments, the recombinant ACE2 protein is expressed on epithelial cells. Accordingly, also described herein is a non-human animal cell expressing a recombinant ACE2 protein, optionally wherein the non-human animal cell (e.g., rat cell or mouse cell) is a somatic cell, optionally wherein the somatic cell is an epithelial cell. Non-limiting examples of epithetical cells that may express a recombination ACE2 protein as described herein include respiratory and/or gastrointestinal epithelial cells, e.g., an alveolar cell of the lung, an esophagus upper and stratified epithelial cell, an absorptive enterocyte from the ileum or colon, etc. In some embodiments, a non-human animal cell as described herein expresses the recombinant ACE2 protein in the epithelium of small intestine villi, surface epithelium of the large intestine (colon), the epithelium of large to small bronchioles and bronchi of the lung, respiratory epithelium of the trachea, proximal tubular epithelium of the kidney, respiratory epithelium of the nasal cavity, and/or the stratum granulosum and/or stratum spinosum of oral mucosa/tongue in the oral cavity.

III. METHODS OF USING NON-HUMAN ANIMALS COMPRISING A HUMANIZED ACE2 LOCUS FOR ASSESSING CORONAVIRUS INFECTION AND/OR ANTI-CORONAVIRUS THERAPIES

Various methods are provided for using the non-human animals comprising a human or humanized ACE2 locus for assessing coronavirus infection and/or the in vivo efficacy of human anti-coronavirus treatments. Because the non-human animals comprise a human or humanized ACE2 locus, the non-human animals will more accurately reflect coronavirus infection mediated by human ACE2 or human anti-coronavirus therapies than non-human animals with a non-humanized ACE2 locus. As one example, the methods can monitor coronavirus infection comprising infecting a non-human animal as described herein with a coronavirus that utilizes a human ACE2 protein for infection. In some embodiments, a non-human animal as described herein may be infected by intranasal inhalation of the coronavirus, e.g., SARS-CoV-2. In some embodiments, a non-human animal as described herein may be infected by intragastric injection.

In some embodiments, the method further comprises assessing the non-human animal for coronavirus related disorders and/or diseases, e.g., lung capacity, gastrointestinal disorders and/or clotting related disorders, e.g., ischemia, and or disease progression. Disease progression may be monitored by obvious clinical signs, e.g., respiratory distress, neurological symptoms, death, etc. Disease progression may also be monitored by measuring the amount of replicating viruses of the coronavirus, e.g., SARS-CoV-2, that may be isolated from organs (e.g., lungs, brain) of of the infected animal, e.g., by well-known plaque assays.

In some embodiments, a non-human animal comprising a modified endogenous ACE2 locus is infected with a SARS-CoV-2 strain, e.g., the non-human animal further comprises replicating SARS-CoV-2. In some embodiments, a non-human animal comprising a modified endogenous ACE2 locus as described herein and replicating SARS-CoV-2 exhibits COVID-19 symptoms for at least one, at least two, at least three, at least four, or at least five days post infection. In some embodiments, the COVID-19 symptom is selected from the group consisting of viral replication in an organ, minimal to severe inflammation (perivascular, vascular, peribronchiolar, septa and alveoli), minimal to severe necrosis (vascular, bronchioles, septa and alveoli), minimal to severe syncytia (vascular endothelium, bronchiolar epithelium and alveolar epithelium), minimal to severe hypertrophy/hyperplasia (vascular endothelium, bronchiolar and alveolar epithelium), minimal to severe hemorrhage (bronchioles and alveoli), minimal to severe edema (bronchioles and alveoli), minimal to severe fibrin (alveoli) and/or minimal to severe hyaline membranes (alveoli), and any combination thereof. In some embodiments, the COVID-19 symptom is selected from the group consisting of viral replication in an organ, necrosis of epithelium, e.g., necrosis of bronchiolar epithelium, vasculitis, endothelialitis, alveolar hyperplasia and/or syncytia, bronchiolar hyperplasia and syncytia, alveolar hemorrhage, perivascular edema, and any combination thereof. In some embodiments, the amount of replicating virus isolated from an organ of an infected non-human animal comprising a genetically modified endogenous is directly correlated with the severity of at least one symptom selected from the group consisting of inflammation (perivascular, vascular, peribronchiolar, septa and alveoli), necrosis (vascular, bronchioles, septa and alveoli), syncytia (vascular endothelium, bronchiolar epithelium and alveolar epithelium), hypertrophy/hyperplasia (vascular endothelium, bronchiolar and alveolar epithelium), hemorrhage (bronchioles and alveoli), minimal to severe edema (bronchioles and alveoli), fibrin (alveoli) and/or hyaline membranes (alveoli), necrosis of epithelium, e.g., necrosis of bronchiolar epithelium, vasculitis, endothelialitis, alveolar hyperplasia and/or syncytia, bronchiolar hyperplasia and syncytia, alveolar hemorrhage, perivascular edema, and any combination thereof. In some embodiments, severity of a COVID19 symptom is scored on a scale of 0 to 4 (0—within normal limits, 1—minimal, 2—mild, 3—moderate and 4—severe).

In some embodiments, a method as described herein assesses or identifies a candidate agent capable of preventing, reducing or otherwise treating coronavirus infection and related disorders, (e.g., preventing, reducing or eliminating binding of the coronavirus (ligand of a human ACE2 protein) to the human ACE2 protein), the method comprising administering an antigen binding protein specific for a coronavirus to a non-human animal that comprises a humanized ACE2 locus and monitoring the non-human animal for coronavirus related disorders and/or diseases, e.g., lung capacity, gastrointestinal disorders and/or clotting related disorders, e.g., ischemia, wherein the non-human animal is infected with the coronavirus before, simultaneously with, or after the administration, and wherein a reduction of the coronavirus related disorders and/or diseases compared to that of a control animal identifies the candidate agent as capable of preventing, reducing or otherwise treating coronavirus infection and related disorders, e.g., identifies the candidate as capable of preventing, reducing or eliminating binding of the coronavirus (ligand of a human ACE2 protein) to human ACE2 protein.

In some embodiments, a non-human animal comprising a modified endogenous ACE2 locus is infected with a SARS-CoV-2 strain, e.g., the non-human animal further comprises replicating SARS-CoV-2, before, after, or simultaneous with an antigen binding protein (e.g., an antibody) specific for SARS-CoV-2 (e.g., the spike protein of SARS-CoV-2). Accordingly, in some embodiments, a non-human animal as described herein comprises a modified endogenous ACE2 locus, replicating SARS-CoV-2, and an antigen binding protein that binds SARS-CoV-2. In some embodiments, a method described herein comprises administering an antigen-binding protein that binds SARS-CoV-2 and SARS-CoV-2 to a non-human animal comprising a genetically modified endogenous ACE2 locus as described herein and monitoring the non-human animal for COVID-19 related symptoms, wherein antigen-binding protein that binds SARS-CoV-2 may be administered prior to, simultaneously with, or after the administration of SARS-CoV-2. In some embodiments, the non-human animal is monitored within one week of administration of (infection with) SARS-CoV-2. In some embodiments, the non-human animal is monitored for at least 3 days after administration of (infection with) SARS-CoV-2. In some embodiments, the non-human animal is monitored for at least 3 days after administration of (infection with) SARS-CoV-2. In some embodiments, the non-human animal is monitored for COVID-19 related symptoms 1 to 2 days after administration of (infection with) SARS-CoV-2.

In some embodiments, the COVID-19 symptom is selected from the group consisting of viral replication in an organ, minimal to severe inflammation (perivascular, vascular, peribronchiolar, septa and alveoli), minimal to severe necrosis (vascular, bronchioles, septa and alveoli), minimal to severe syncytia (vascular endothelium, bronchiolar epithelium and alveolar epithelium), minimal to severe hypertrophy/hyperplasia (vascular endothelium, bronchiolar and alveolar epithelium), minimal to severe hemorrhage (bronchioles and alveoli), minimal to severe edema (bronchioles and alveoli), minimal to severe fibrin (alveoli) and/or minimal to severe hyaline membranes (alveoli), and any combination thereof. In some embodiments, the COVID-19 symptom is selected from the group consisting of viral replication in an organ, necrosis of epithelium, e.g., necrosis of bronchiolar epithelium, vasculitis, endothelialitis, alveolar hyperplasia and/or syncytia, bronchiolar hyperplasia and syncytia, alveolar hemorrhage, perivascular edema, and any combination thereof.

In some embodiments, the dose of the antigen-binding protein is inversely correlated with the amount of replicating virus isolated from an organ of an infected non-human animal comprising a genetically modified endogenous and with the severity of at least one symptom selected from the group consisting of inflammation (perivascular, vascular, peribronchiolar, septa and alveoli), necrosis (vascular, bronchioles, septa and alveoli), syncytia (vascular endothelium, bronchiolar epithelium and alveolar epithelium), hypertrophy/hyperplasia (vascular endothelium, bronchiolar and alveolar epithelium), hemorrhage (bronchioles and alveoli), minimal to severe edema (bronchioles and alveoli), fibrin (alveoli) and/or hyaline membranes (alveoli), necrosis of epithelium, e.g., necrosis of bronchiolar epithelium, vasculitis, endothelialitis, alveolar hyperplasia and/or syncytia, bronchiolar hyperplasia and syncytia, alveolar hemorrhage, perivascular edema, and any combination thereof. In some embodiments, severity of a COVID19 symptom is scored on a scale of 0 to 4 (0—within normal limits, 1—minimal, 2—mild, 3—moderate and 4—severe).

IV. METHODS OF MAKING NON-HUMAN ANIMALS COMPRISING A HUMANIZED ACE2 LOCUS

Various methods are provided for making a non-human animal comprising a humanized ACE2 locus as disclosed elsewhere herein. Any convenient method or protocol for producing a genetically modified organism is suitable for producing such a genetically modified non-human animal. See, e.g., Cho et al. (2009) *Current Protocols in Cell Biology* 42:19.11:19.11.1-19.11.22 and Gama Sosa et al. (2010) *Brain Struct. Funct.* 214(2-3):91-109, each of which is herein incorporated by reference in its entirety for all purposes. Such genetically modified non-human animals can be generated, for example, through gene knock-in at a targeted ACE2 locus.

For example, the method of producing a non-human animal comprising a humanized ACE2 locus can comprise: (1) modifying the genome of a pluripotent cell to comprise the humanized ACE2 locus; (2) identifying or selecting the genetically modified pluripotent cell comprising the humanized ACE2 locus; (3) introducing the genetically modified pluripotent cell into a non-human animal host embryo; and (4) implanting and gestating the host embryo in a surrogate mother. Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized ACE2 locus.

The methods can further comprise identifying a cell or animal having a modified target genomic locus. Various methods can be used to identify cells and animals having a targeted genetic modification.

The screening step can comprise, for example, a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

An example of a suitable pluripotent cell is an embryonic stem (ES) cell (e.g., a mouse ES cell or a rat ES cell). The modified pluripotent cell can be generated, for example, through recombination by (a) introducing into the cell one or more targeting vectors comprising an insert nucleic acid flanked by 5' and 3' homology arms corresponding to 5' and 3' target sites, wherein the insert nucleic acid comprises a humanized ACE2 locus; and (b) identifying at least one cell comprising in its genome the insert nucleic acid integrated at the target genomic locus. Alternatively, the modified pluripotent cell can be generated by (a) introducing into the cell: (i) a nuclease agent, wherein the nuclease agent induces a nick or double-strand break at a recognition site within the target genomic locus; and (ii) one or more targeting vectors comprising an insert nucleic acid flanked by 5' and 3' homology arms corresponding to 5' and 3' target sites located in sufficient proximity to the recognition site, wherein the insert nucleic acid comprises the humanized ACE2 locus; and (b) identifying at least one cell comprising a modification (e.g., integration of the insert nucleic acid) at the target genomic locus. Any nuclease agent that induces a nick or double-strand break into a desired recognition site can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems or components of such systems (e.g., CRISPR/Cas9). See, e.g., US 2013/0309670 and US 2015/0159175, each of which is herein incorporated by reference in its entirety for all purposes.

The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. See, e.g., U.S. Pat. No. 7,294,754, herein incorporated by reference in its entirety for all purposes.

Alternatively, the method of producing the non-human animals described elsewhere herein can comprise: (1) modifying the genome of a one-cell stage embryo to comprise the humanized ACE2 locus using the methods described above for modifying pluripotent cells; (2) selecting the genetically modified embryo; and (3) implanting and gestating the genetically modified embryo into a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal comprise the humanized ACE2 locus. It is recognized that depending on the method used to generate the F0 animal, the number of cells within the F0 animal that have the humanized ACE2 locus will vary. The introduction of the donor ES cells into a pre-morula stage embryo from a corresponding organism (e.g., an 8-cell stage mouse embryo) via for example, the VELOCIMOUSE® method allows for a greater percentage of the cell population of the F0 animal to comprise cells having the nucleotide sequence of interest comprising the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted modification.

The cells of the genetically modified F0 animal can be heterozygous for the humanized ACE2 locus or can be homozygous for the humanized ACE2 locus.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

TABLE 6

Description of Sequences.

| SEQ ID NO | Type | Description |
|---|---|---|
| 1 | DNA | mACE2 |
| 2 | Protein | mACE2-Q8R0I0-1; NP_001123985.1 |
| 3 | DNA | hACE2 |
| 4 | Protein | hACE2-Q9BYF1-1; NP_068576.1 |
| 5 | DNA | 7878 allele |
| 6 | DNA | 7878mTu Fwd Primer |
| 7 | DNA | 7878 mTu Probe |
| 8 | DNA | 7878 mTu Rev Primer |
| 9 | DNA | 7878mTD Fwd Primer |
| 10 | DNA | 7878mTD Probe |
| 11 | DNA | 7878mTD Rev Primer |
| 12 | DNA | 7878hTU Fwd Primer |
| 13 | DNA | 7878hTU Probe |
| 14 | DNA | 7878hTU Rev Primer |
| 15 | DNA | 7878hTD Fwd Primer |
| 16 | DNA | 7878hTD Probe |
| 17 | DNA | 7878hTD Rev Primer |
| 18 | DNA | 7878 Border A |
| 19 | DNA | 7878 Border B |
| 20 | DNA | 7878 Border C |
| 21 | DNA | 7878 Border D |
| 22 | DNA | 7879 Allele |
| 23 | DNA | 7879 Border E |
| 24 | Protein | Chimeric human/mouse ACE2 |
| 25 | DNA | Chimeric human/mouse ACE2 |
| 26 | Protein | mACE2 signal sequence |
| 27 | Protein | hACE2 extracellular domain |
| 28 | Protein | mACE2 transmembrane domain |
| 29 | Protein | mACE2 cytoplasmic domain |
| 30 | DNA | 90034mTU Fwd Primer |
| 31 | DNA | 90034mTU Probe |
| 32 | DNA | 90034mTU Rev Primer |
| 33 | DNA | 90034mretU Fwd Primer |
| 34 | DNA | 90034mretU Probe |
| 35 | DNA | 90034mretU Rev Primer |
| 36 | DNA | 90034mretU2 Fwd Primer |
| 37 | DNA | 90034mretU2 Probe |
| 38 | DNA | 90034mretU2 Rev Primer |
| 39 | DNA | 90034mretD Fwd Primer |
| 40 | DNA | 90034mretD Probe |
| 41 | DNA | 90034mretD Rev Primer |
| 42 | DNA | 90034mretD2 Fwd Primer |
| 43 | DNA | 90034mretD2 Probe |
| 44 | DNA | 90034mretD2 Rev Primer |
| 45 | DNA | 90034mretD3 Fwd Primer |
| 46 | DNA | 90034mretD3 Probe |
| 47 | DNA | 90034mretD3 Rev Primer |
| 48 | DNA | 90034mretD 4 Fwd Primer |
| 49 | DNA | 90034mretD4 Probe |
| 50 | DNA | 90034mretD4 Rev Primer |
| 51 | DNA | mGU |
| 52 | DNA | mGU2 |

TABLE 6-continued

| Description of Sequences. | | |
|---|---|---|
| SEQ ID NO | Type | Description |
| 53 | DNA | mGD |
| 54 | DNA | mGD2 |
| 55 | DNA | 90034 Border A |
| 56 | DNA | Human coding ex 3-4 Foward primer |
| 57 | DNA | Human coding ex 3-4 Reverse primer |
| 58 | DNA | Human coding ex 3-4 Probe |
| 59 | DNA | Human coding ex 16-17 Forward primer |
| 60 | DNA | Human coding ex 16-17 Reverse primer |
| 61 | DNA | Human coding ex 16-17 Probe |
| 62 | DNA | Mouse coding ex 11-12 Forward primer |
| 63 | DNA | Mouse coding ex 11-12 Reverse primer |
| 64 | DNA | Mouse coding ex 11-12 Probe |
| 65 | DNA | Mouse coding ex 17-18 Forward Primer |
| 66 | DNA | Mouse coding ex 17-18 Reverse Primer |
| 67 | DNA | Mouse coding ex 17-18 Probe |

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

The following examples are provided for illustrative purposes only and are not intended to limit the scope of the invention.

Example 1: Generation of Mice Comprising a Humanized ACE2 Locus

Described in this example is the generation of mice comprising a humanized ACE2 locus for use as a model useful in understanding coronavirus infection, particularly SARS-CoV and SARS-CoV-2 function, and validation of vaccination and/or treatment protocols therefor.

Illustrative (not-to-scale) diagrams of the human and mouse ACE2 gene are provided in FIG. 1A. NCBI Accession number NP-001123985.1 provides an exemplary non-limiting mouse ACE2 protein amino acid sequence, which is set forth as SEQ ID NO:2. An exemplary non-limiting example of a nucleotide sequence that encodes the exemplary non-limiting mouse ACE2 protein is set forth as SEQ ID NO:1. Nucleotides 1-51 of SEQ ID NO:1 encodes the mouse ACE2 signal peptide (set forth as amino acids 1-17 of SEQ ID NO:2), nucleotides 52-2220 of SEQ ID NO:1 encode the mouse ACE2 extracellular domain set forth as amino acids 18-740 of SEQ ID NO:2), nucleotides 2221-2283 of SEQ ID NO:1 encode the mouse ACE2 transmembrane domain (set forth as amino acids 741-761 of SEQ ID NO:2), and nucleotides 2284-2418 of SEQ ID NO:1 encode the mouse ACE2 cytoplasmic domain (set forth as amino acids 762-805 of SEQ ID NO:2). NCBI Accession number NP-068576.1 provides an exemplary non-limiting human ACE2 protein amino acid sequence, which is set forth as SEQ ID NO:4. Amino acids 1-17 of SEQ ID NO:4 sets forth the amino acid sequence of the signal peptide of human ACE2 protein, amino acids 18-740 of SEQ ID NO:4 sets forth the amino acid sequence of the extracellular domain of human ACE2 protein, amino acids 741-761 of SEQ ID NO:4 sets forth the amino acid sequence of the transmembrane domain of human ACE2 protein, and amino acids 762-805 of SEQ ID NO:4 sets forth the amino acid sequence of the cytoplasmic domain of human ACE2 protein. An exemplary non-limiting example of a nucleotide sequence that encodes the exemplary non-limiting mouse ACE2 protein is set forth as SEQ ID NO:3. Nucleotides 1-51 of SEQ ID NO:3 encode a signal peptide amino acid sequence of human ACE2 protein (set forth as amino acids 1-17 of SEQ ID NO:4), nucleotides 52-2220 of SEQ ID NO:3 encode an extracellular domain amino acid sequence of human ACE2 protein (set forth as amino acids 18-740 of SEQ ID NO:4), nucleotides 2221-2283 of SEQ ID NO:3 encode a transmembrane domain amino acid sequence of human ACE2 protein (set forth as amino acids 741-761 of SEQ ID NO:4), and nucleotides 2284-2418 of SEQ ID NO:3 encode a cytoplasmic domain amino acid sequence of human ACE2 protein (set forth as amino acids 762-805 of SEQ ID NO:4).

A large targeting vector comprising a 5' homology arm comprising 14.9 kb from RP23-244L14 and 3' homology arm comprising 126 kb from RP23-244L14 was generated to replace part of coding exon 1 through part of coding exon 17 (e.g., part of coding exon 1, intron 1, exons 2-16 and intervening introns, intron 16, and part of coding exon 17) of mouse ACE2 with the corresponding human sequence of ACE2. See, e.g., FIGS. 1A and 1B. The targeting vector is designed to replace 45,019 bp of the mouse sequence with 36,742 bp of the human sequence, which also is modified to comprise a self-deleting foxed neo cassette (loxP-mPrm1-Crei-pA-hUb1-em7-Neo-pA-loxP) inserted into the human intron 16. See, e.g., FIG. 1B.

Since the ACE2 locus is found on the X-chromosome, CRISPR/Cas9 components were introduced into male F1H4 mouse embryonic stem cells together with the large targeting vector described herein. Loss-of-allele assays using the primers and probes set forth in Table 3 were performed to detect loss of the endogenous mouse allele, and gain-of-allele assays using the primers and probes set forth in Table 4 were performed to detect gain of the humanized allele. Loss-of-allele and gain-of-allele assays are described, for example, in US 2014/0178879; US 2016/0145646; WO 2016/081923; and Frendewey et al. (2010) Methods Enzymol. 476:295-307, each of which is herein incorporated by reference in its entirety for all purposes.

TABLE 3

| Mouse TAQMAN® Loss-of-Allele Assays | | |
|---|---|---|
| LOA Assay | Primer/Probe | Sequence |
| 7878mTU | Fwd | CCCAGATGGCTAAATTCAATTGA (SEQ ID NO: 6) |
| | Probe (MBG) | TTCATCTGGAAAATTG (SEQ ID NO: 7) |
| | Rev | GGAATCTGGGCAAATAATTCATTC (SEQ ID NO: 8) |
| 7878mTD | Fwd | GGGCCGCATCAATGATGTC (SEQ ID NO: 9) |
| | Probe (BHQ) | TGGCCTGAATGATAACAGCCTGGA (SEQ ID NO: 10) |
| | Rev | GTGGCTCAAGTGTTGGGTGAATC (SEQ ID NO: 11) |

TABLE 4

| Human TAQMAN® Gain-of-Allele Assays | | |
|---|---|---|
| GOA Assay | Primer/Probe | Sequence |
| 7878hTU | Fwd | GTGAGGCTGGACTTGGGAAT (SEQ ID NO: 12) |
| | Probe (BHQ) | CCTTTCCTCTTTGTCACAGACCTCCA (SEQ ID NO: 13) |
| | Rev | GGAGGGCTCTGCCTGGATT (SEQ ID NO: 14) |
| 7878hTD | Fwd | GCAAAGGTCCCTTTCTTATGTGC (SEQ ID NO: 15) |
| | Probe (BHQ) | CCCAGTGCTACCTCCAAATGCCA (SEQ ID NO: 16) |
| | Rev | CAGGTCCTATGACCAAGTCTCTA (SEQ ID NO: 17) |

The resulting humanized mouse ACE2 allele comprising the self-deleting foxed neo cassette comprises a nucleotide sequence is set forth in SEQ ID NO:5 (referred to as the 7878 allele). FIG. 1B. FIG. 1B also provides the sequences at various junctions (A, B, C, D) of the 7878 allele. The nucleotide sequence of (A) the 5' mouse/human junction is set forth as SEQ ID NO:18. FIG. 1B. The nucleotide sequence of (B) the 5' human/cassette junction is set forth as SEQ ID NO:19. FIG. 1B. The nucleotide sequence of (C) the 3' cassette/human junction is set forth as SEQ ID NO:20. FIG. 1B. The nucleotide sequence of (D) the 3' human/mouse junction is set forth as SEQ ID NO:21.

F0 mice were then generated using the VELOCI-MOUSE® method. See, e.g., U.S. Pat. Nos. 7,576,259; 7,659,442; 7,294,754; US 2008/007800; and Poueymirou et al. (2007) Nature Biotech. 25(1):91-99, each of which is herein incorporated by reference in its entirety for all purposes.

Upon removal of the self-deleting neomycin cassette with Cre recombinase, the loxP and cloning sites (77 bp) remain inserted in human intron 16. FIG. 1C. The resulting humanized mouse, cassette-deleted, ACE2 allele is set forth in SEQ ID NO:22 (referred to as the 7879 allele). FIG. 1C. FIG. 1C also provides the sequence at (E) cloning and loxp site after recombination, which sequence is set forth as SEQ ID NO: 23.

The modified endogenous mouse ACE2 7879 allele encodes a chimeric human/mouse ACE2 protein under the regulatory control of endogenous mouse ACE2 promoter and other regulatory elements. The amino acid sequence of the encoded chimeric human/mouse ACE2 protein is set forth as SEQ ID NO:24. An exemplary nucleotide sequence, e.g., CDS, that encodes the chimeric human/mouse ACE protein is set forth as SEQ ID NO:25.

The chimeric human/mouse ACE2 protein comprises a mouse ACE2 signal sequence at amino acids 1-17 of SEQ ID NO:24 (the amino acid sequence of the signal sequence of the chimeric human/mouse ACE2 protein is set forth as SEQ ID NO:26 and may be encoded by nucleotides 1-51 of SEQ ID NO:25), a human ACE2 extracellular domain at amino acids 18-740 of SEQ ID NO: 24 (the amino acid sequence of the extracellular domain of the chimeric human/mouse ACE2 protein is set forth as SEQ ID NO:27 and may be encoded by nucleotides 52-2220 of SEQ ID NO:25), a mouse ACE2 transmembrane domain at amino acids 741-761 of SEQ ID NO:24 (the amino acid sequence of the transmembrane domain of the chimeric human/mouse ACE2 protein is set forth as SEQ ID NO:28 and may be encoded by nucleotides 2221-2283 of SEQ ID NO:25), and a mouse ACE2 cytoplasmic domain at amino acids 762-805 of SEQ ID NO:24 (the amino acid sequence of the cytoplasmic domain of the chimeric human/mouse ACE2 protein is set forth as SEQ ID NO:29 and may be encoded by nucleotides 2284-2418 of SEQ ID NO:25). The mouse portion(s) of the chimeric human/mouse ACE2 protein spans amino acids 1-19 and 741-805 of SEQ ID NO:24 (and may be encoded by nucleotides 1-57 and 2221-2418 of SEQ ID NO:25, respectively). The human portion of the chimeric human/mouse ACE2 protein spans amino acids 20-740 of SEQ ID NO:24 (and may be encoded by nucleotides 58-2220 of SEQ ID NO:25).

Example 2: Characterization of Humanized ACE2 Mouse

Humanized ACE2 mice were compared to ACE2-null mice. ACE2-null mice lack an ACE coding sequence at an endogenous ACE2 allele (see, e.g., FIGS. 2A and 2B).

Expression Levels of Chimeric Human/Mouse ACE2 Messenger RNA (mRNA)

The expression levels of the chimeric human/mouse ACE2 mRNA were analyzed by TaqMan qRT-PCR analysis as described herein. Messenger RNA levels in this Example were analyzed by Real-Time Quantitative Polymerase Chain Reaction (RT-qPCR). Total RNA from each sample was extracted and reverse transcribed using primers that amplify across intronic boundaries of mouse and human ACE2 genes. RT-qPCR was performed using probes and primers of readily available kits.

Specifically, 1 cm pieces of small intestine, colon, kidney, and liver were isolated directly into RNALater® (Ambion by Life Technologies), and chilled to 4'C. Tissues were homogenized in TRIzolTM, and chloroform was used for phase separation. The aqueous phase, containing total RNA, was purified using the MagMAX™–96 for Microarrays Total RNA Isolation Kit (Ambion by Life Technologies) according to manufacturer's specifications. Genomic DNA was removed using RNase-Free DNase Set (Qiagen). mRNA was reverse-transcribed into cDNA using Super-Script® VILO™ Master Mix (Invitrogen by Life Technologies). cDNA was amplified with the SensiFAST™ Probe Lo-ROX (Meridian) using the 12K Flex System (Thermofisher). A housekeeping control gene (Gapdh) was used to normalize any cDNA input differences. Data were reported as the comparative CT method using delta delta CT.

Negative control mRNAs were extracted from mice that are deleted in the ACE2 gene (aka ACE2-null, or knockout, or KO). Positive control mRNAs were extracted from wild-type (WT) mice. Human control mRNAs from heart (Cat #1H30-50), kidney (Cat #1H50-50), lung (Cat #1H40-50), small intestine (Cat #1H24-50), and adult human tracheal epithelial cells (Cat #504-R25a) were purchased from Cell Applications Inc. (San Diego, Calif.).

The sequences of the primers and probes used in the analysis are provided in Table 5 below. Note that exons denoted in Table 5 are numbered counting coding exons only.

TABLE 5

| Assay | Forward Primer SEQ ID NO | Reverse Primer SEQ ID NO | Probe SEQ ID NO |
|---|---|---|---|
| | ACE2 | | |
| Human coding ex 3-4 | 56 | 57 | 58 |
| Human coding ex 16-17 | 59 | 60 | 61 |
| | ACE2 | | |
| Mouse coding ex 11-12 | 62 | 63 | 64 |
| Mouse coding ex 17-18 | 65 | 66 | 67 |

FIG. 4 shows that post natal (P4-P7) mice comprising an endogenous ACE2 locus modified to encode a humanized ACE2 protein expresses levels of the humanized ACE2 mRNA similar to the levels of wild-type ACE2 expressed by wild-type mice. Panel A and B provide data from the two human-specific assays (hEx3-4 and hEx16-17), which amplify only humanized ACE2 allele and normal human RNA. No amplification was detected in ACE2-KO tissues. Zooming into relative levels shows that humanized ACE2 allele is expressed at lower, but detectable, levels compared with human tissues. The mEx17-18 assay is shown in panel C. This assay amplifies both mouse and humanized ACE2 allele, but does not amplify the human samples. KO mice are negative controls. The mEx11-12 assay amplifies both human and mouse genes due to identity of the base pairs in this region between these species. Here it fails to amplify ACE2-KO tissues. The levels of humanized ACE2 mRNA in aged mice (P40) is shown in FIG. 5. As shown in FIG. 5, as mice age, the levels of humanized ACE2 mRNA in animal genetically expressing a humanized endogenous ACE2 locus remained low when compared to the levels of murine ACE2 mRNA in wildtype mice. Notably, the levels of murine ACE2 mRNA in wildtype mice increase in the colon, duodenum, and lungs as the mice age (FIGS. 4 and 5).

Expression Levels of Chimeric Human/Mouse ACE2 Protein in the Respiratory and Gastrointestinal Tracts Pieces of tissues (lung, trachea, duodenum) from the same mouse cohort as qPCR experiment were harvested directly into chilled 4% paraformaldehyde and post-fixed overnight with mild rocking. Tissues were rinsed 3× with PBS, then serially dehydrated in 70%, 85%, 95%, and 100% ethanol, defatted with xylene, and embedded in paraffin.

Automated staining was performed on a Ventana Ultra autostainer (Roche Diagnostics) using Universal protocol. Four micrometer paraffin sections of different tissues were used.

Slides were deparaffinized with EZPrep (Roche Diagnostics) at 69 C for 24 minutes; antigen retrieval was performed with CC1 buffer (Roche Diagnostics) at 100 C for 56 minutes, followed by blocking with 10% normal horse serum (Vector Labs) for 32 minutes.

Anti-ACE2 antibody recognizing both mouse and human ectodomain (AF933, R&D Systems) or anti-ACE2 antibody recognizing only mouse ectodomain (AF3437 R&D Systems) were added at concentration of 0.5 μg/ml followed by 5-hour incubation at room temperature. Secondary horse anti-goat IgG antibodies (Vector Labs) at 1:200 dilution were incubated for 1 hour at room temperature, followed by detection with DABMap kit (Roche diagnostics) according to the preset protocol parameters. Slides were counterstained with Hematoxylin (Roche Diagnostics) for 32 minutes followed by incubation with Bluing Reagent (Roche Diagnostics) for 8 minutes, washed with soap and tap water, dehydrated in increasing concentrations of ethyl alcohol and xylenes and mounted with Cytoseal-60 (Thermo Scientific). All images were obtained at 20× magnification.

FIGS. 6 and 7 are representative images that show that a mouse comprising an endogenous ACE2 locus modified to encode a humanized ACE2 protein expresses the humanized ACE2 protein on respiratory and gastrointestinal epithelial cells. Provided in Table 7 is a summary of ACE2 expression as observed by immunohistochemistry in various organs of newborn (P5) wildtype (WT) mice, adult (5 wk) wildtype (WT) mice, newborn (P7) mice comprising an endogenous ACE2 locus modified to encode a humanized ACE2 protein (hACE2), and newborn (P7) ACE2 knockout (KO) mice.

TABLE 7

| | 5Wk WT | | P7 hACE2 | | P7 ACE2 KO | |
|---|---|---|---|---|---|---|
| | AF933 | AF3437 | AF933 | AF3437 | AF933 | AF3437 |
| Small intestine | ++ | +++ | +++ | – | – | – |
| | Staining in the epithelium of the villi | | | | | |
| Large intestine (colon) | ++ | +++ | ++ | – | – | – |
| | Staining in the surface epithelium | | | | | |
| Lungs | + | + | + | – | – | – |
| | Staining in the epithelium of large to small bronchioles and bronchi | | | | | |
| Trachea | + | + | + | – | – | – |
| | Staining in the respiratory epithelium | | | | | |
| Liver | + | + | – | – | – | – |
| | Staining in the sinusoidal endothelium | | | | | |
| Kidney | ++ | ++ | ++ | + | – | – |
| | Staining in the proximal tubular epithelium | | | | | |
| Heart | + | + | – | – | – | – |
| | Staining in the muscular junctions | | | | | |
| Nasal cavity | N/A | N/A | –/++ | – | – | – |
| | Staining in the respiratory epithelium | | | | | |
| Oral Cavity | N/A | N/A | +++ | – | – | – |
| | Staining in the Str. granulosum and Str. spinosum of oral mucosa/tongue | | | | | |

The expression of hACE2 in hACE2 mice was similar to ACE2 expression in WT mice and humans with few exceptions. Staining of sinusoidal staining and muscular junctions in the heart observed in WT mice was absent in hACE2 mice. Staining in the nasal mucosa, oral mucosa and tongue was present in hACE2 mice but was absent in WT mice. These exceptions were likely due to human ACE2 gene expression in hACE2 mice.

Example 3: Humanized ACE2 Mice as Models of SARS-CoV-2 Infection and Use in Assessing Anti-SARS-CoV-2 Therapies Humanized ACE2 mice allow for the study of not only non-mouse adapted SARS-CoV-2 infection, but also the efficacy of antibodies for improving SARS-CoV-2-mediated pathologies.

Generally, mice expressing humanized ACE2 as described in Example 1 are treated with antibodies 1 day prior to infection with SARS-CoV-2. Mice are then intranasally inoculated with SARS-CoV-2 and monitored daily for weight loss and signs of clinical disease. At 2 days post-infection, mice are euthanized and lungs were harvested for lung pathology by histological analysis and qRT-PCR for viral titers.

SARS-CoV-2 Model

Humanized ACE2 mice as described in Example 1 were infected with a human SARS-CoV-2 isolate, WA1 at doses of $10^2$ (e.g., 10E2) PFU, $10^3$ (e.g., 10E3) PFU, $10^4$ (e.g., 10E4) PFU, or $10^5$ (e.g., 10E5) PFU. Mice were monitored and weighed daily for 7 days. No significant weight loss was observed among mice infected with SARS-CoV-2 and control mice exposed to PBS only (FIG. 8).

Both plaque assay and qPCR for the presence of the N gene were performed on lung homogenates collected on days 2, 4. 7 and 10 post-infection. As shown in FIG. 9, replicating virus could be isolated at day 2 at all inoculums, however, all groups cleared the virus to below the limit of detection by day 4 post-infection. This trend is confirmed by qPCR. At day 2, mice at all inoculums had detectable virus which exhibited a dose dependent pattern. At day 4 post-infection, only those mice in the $10^5$ group had appreciable expression of the nucleocapsid gene of SARS-CoV-2, FIG. 10.

H&E stained lung sections were examined for pathological changes and providing with a pathology score. Lung sections showed low levels of inflammatory infiltrate and damage (data not shown), demonstrating that the humanized ACE2 mice as described in Example 1 are feasible for use in antibody testing experiments and use of $1\times10^5$ PFU of SARS-COV-2 WA1 is an appropriate inoculum.

Antibody Prophylaxis Against SARS-CoV-2 in SARS-CoV-2 Model

Humanized ACE2 mice were prophylactically treated at 2 days prior to infection via intraperitoneal injection with either one of two single monoclonal antibody specific for SARS-CoV-2 spike protein at 50 mg/kg, 5 mg/kg or 0.5 mg/kg or a combination of both antibodies, each at 25 mg/kg, 2.5 mg/kg, 0.25 mg/kg or 0.25 mg/kg diluted in PBS. On day 0, mice were anesthetized and intranasally infected with $1\times10^5$ PFU of WA1 SARS-CoV-2.

FIG. 11 shows that 50 µg of either a single anti-spike protein antibody or 25 µg each of a combination of two anti-spike antibodies were able to reduce weight loss of mice infected with SARS-CoV-2 over the 2 days of observation.

On day 2 post-infection, mice were sacrificed, and lungs were harvested for analysis of lung pathology and viral titer. Both by plaque assay and by qPCR for the presence of the N gene, a reduction in viral titer was observed in a dose dependent fashion for both the single monoclonal antibodies as well as the combination. (FIG. 12 and FIG. 13). Lung sections of all infected control animals that received placebo showed SARS-CoV-2 induced inflammation characterized by minimal to mild infiltration of lymphocytes, macrophages, and neutrophils, most commonly in the peribronchiolar and perivascular areas, and less commonly in the alveolar septa and vascular wall. Necrosis was most prominently observed in the bronchiolar epithelium. Inflammation in the vascular walls (vasculitis/endothelitis) was accompanied by endothelial hypertrophy/hyperplasia, endothelial syncytia, and vascular necrosis (FIG. 14). Other changes include alveolar and bronchiolar hyperplasia and syncytia, alveolar hemorrhage, and perivascular edema. Histopathological evaluation show that the the monotherapies and combination therapy reduced the lung pathology and total pathology score in a dose-dependent manner; significant reduction was observed only at 50 mg/kg. (FIG. 15). This was correlated well with virus load data, which also showed a greatest reduction at 50 mg/kg (FIG. 15).

Experimental Materials and Methodologies

Viruses and Cells

SARS-CoV-2 WA-1 was obtained from the CDC following isolation from a patient in Washington State (WA-1 strain—BEI #NR-52281). All virus stocks were stored at −80° C. until ready to use. VeroE6 cells from ATCC (catalog #CRL-1586) (Manassas, Va.) were used for growing SAR-CoV-2 virus as well as in plaque assays. VeroE6 cells were grown in DMEM (Invitrogen, Carlsbad, Calif.) with 10% FBS (Atlanta Biologicals, Lawerenceville, Ga.), 1% penicillin/streptomycin (Gemini Bioproducts, West Sacramento, Calif.) and 1% L-glutamine (Gibco).

In Vivo Mouse Infections

All infections were performed in an animal biosafety level 3 facility using appropriate practices including HEPA filtered BCON caging system, HEPA filtered PAPR respirators and Tyvek suiting. Animals were anesthetized using a mixture of xylazine (0.38 mg/mouse) and ketamine (1.3 mg/mouse) in 50 µL total volume by intraperitoneal injection. Mice were inoculated intranasally with 50 µL of either PBS or $1\times10^5$ PFU of WA1 SARS-CoV-2 after which all animals were monitored daily for weight loss. Mice were euthanized at day 2, 4 and 7 post-infection and lung tissue was harvested for further analysis. All animals were housed and used in accordance with appropriate Institutional Animal Care and Use Committee guidelines.

Antibody Treatments

Mice were given monoclonal antibodies via intraperitoneal injection at 2 days prior to infection with SARS-CoV-2. Mice received 50 mg/kg, 5 mg/kg or 0.5 mg/kg of a single monoclonal antibody or a combination of 2 monoclonal antibodies each at 25 mg/kg, 2.5 mg/kg or 0.25 mg/kg (totaling 50 mg/kg, 25 mg/kg and 0.5 mg/kg combined) diluted in sterile PBS (Quality Biological) to a total volume of 100 uL.

Histology:

Lung sections were fixed in 4% paraformaldehyde (PFA) in phosphate-buffered saline (PBS) for a minimum of 48 h, after which they were sent to the Histology Core at the University of Maryland, Baltimore, for paraffin embedding and sectioning. Five-micrometer sections were prepared and used for hematoxylin and eosin (H&E) staining by the Histology Core Services. Sections were imaged at 10× magnification and figures were put together using Adobe Photoshop and Illustrator software.

Histopathological evaluation was done by a board-certified veterinary pathologist. The following parameters were evaluated: inflammation (perivascular, vascular, peribronchiolar, septa and alveoli), necrosis (vascular, bronchioles, septa and alveoli), syncytia (vascular endothelium, bronchiolar epithelium and alveolar epithelium), hypertrophy/hyperplasia (vascular endothelium, bronchiolar and alveolar epithelium), hemorrhage (bronchioles and alveoli), edema (bronchioles and alveoli), fibrin (alveoli) and hyaline membranes (alveoli). A 0-4 severity scoring scale was used (0—within normal limits, 1—minimal, 2—mild, 3—moderate and 4—severe) to score the above 21 parameters. A total pathology score was calculated for each mouse by adding the individual histopathological feature scores, and a maximum pathology score of 84 was possible for an individual animal. Statistical analysis was performed using one-way analysis of variance followed by the Tukey's HSD test and a P value of <0.05 was considered significant.

Plaque Assay on Lung Homogenate

SARS-CoV-2 lung titers were quantified by homogenizing mouse lungs in 1 mL phosphate buffered saline (PBS; Quality Biological Inc.) using 1.0 mm glass beads (Sigma Aldrich) and a Beadruptor (Omni International Inc). VeroE6 cells are plated in 6 well plates with $1\times10^5$ cells per well. SARS-CoV-2 virus titer in plaque forming units was determined by plaque assay. In the plaque assay, 25 μl of the lung homogenate is added to 225 ul of PBS and diluted 10 fold across a 6 point dilution curve with 200 μl of diluent added to each well. After 1 hour, a 3 ml agar overlay containing DMEM is added to each well. Plates are incubated for 3 days at 37° C. (5% $CO_2$) before plaques are counted.

What is claimed is:

1. A rodent comprising a genetically modified endogenous ACE2 locus encoding a recombinant ACE2 protein that comprises in operable linkage:

(i) an ACE2 signal sequence of an endogenous ACE2 protein;

(ii) an extracellular domain of a human ACE2 protein;

(iii) a transmembrane domain of the endogenous ACE2 protein; and (iv) a cytoplasmic domain of the endogenous ACE2 protein;

wherein the rodent expresses the recombinant ACE2 protein.

2. The rodent of claim 1, wherein the genetically modified endogenous ACE2 locus comprises a replacement of a nucleotide sequence encoding the extracellular domain of the endogenous ACE2 protein with a nucleotide sequence encoding the extracellular domain of the human ACE2 protein such that the nucleotide sequence encoding the extracellular domain of the human ACE2 protein is operably linked to an endogenous nucleotide sequence encoding (iii) the transmembrane domain of the endogenous ACE2 protein, and (iv) the cytoplasmic domain of the endogenous ACE2 protein.

3. The rodent of claim 1, wherein the genetically modified endogenous ACE2 locus comprises the nucleotide sequence as set forth in SEQ ID NO: 5 or as set forth in SEQ ID NO:22.

4. The rodent of claim 1, further comprising the sequence as set forth in SEQ ID NO:5, the sequence as set forth in SEQ ID NO:22, or the sequence as set forth in SEQ ID NO:25.

5. The rodent of claim 1, wherein the amino acid sequence of (ii) the extracellular domain of the human ACE2 protein comprises the amino acid sequence as set forth in SEQ ID NO:27.

6. The rodent of claim 1, wherein the rodent is heterozygous or homozygous for the genetically modified endogenous ACE2 locus.

7. The rodent of claim 1, wherein the rodent is a rat or a mouse.

8. The rodent of claim 7, wherein the rodent is a mouse, and wherein the recombinant ACE2 protein comprises in operable linkage:

(i) an ACE2 signal sequence of an endogenous mouse ACE2 protein;

(ii) an extracellular domain of a human ACE2 protein;

(iii) a transmembrane domain of the endogenous mouse ACE2 protein; and (iv) a cytoplasmic domain of the endogenous mouse ACE2 protein.

9. The rodent of claim 8, wherein the amino acid sequence of the recombinant ACE2 protein comprises the amino acid sequence as set forth in SEQ ID NO:24.

10. A rodent cell comprising:

a genetically modified endogenous ACE2 locus encoding a recombinant ACE2 protein that comprises in operable linkage:

(i) an ACE2 signal sequence of an endogenous ACE2 protein;

(ii) an extracellular domain of a human ACE2 protein;

(iii) a transmembrane domain of the endogenous ACE2; and (iv) a cytoplasmic domain of the endogenous ACE2 protein;

wherein the rodent cell is:

(a) an embryonic stem(ES) cell, a pluripotent cell, or a germ cell; or (b) a somatic cell that expresses the recombinant ACE2 protein.

11. A rodent tissue comprising the rodent cell of claim 10.

12. The rodent of claim 1, wherein the rodent comprises in its genome a genetic modification of the endogenous ACE2 locus encoding the recombinant ACE2 protein that comprises in operable linkage:

(i) an ACE2 signal sequence of a rodent ACE2 protein set forth in SEQ ID NO: 26;

(ii) an extracellular domain of a human ACE2 protein set forth in SEQ ID NO: 27;

(iii) a transmembrane domain of a rodent ACE2 protein set forth in SEQ ID NO: 28; and (iv) a cytoplasmic domain of a rodent ACE2 protein set forth in SEQ ID NO: 29.

13. The rodent cell of claim 10, comprising a genetically modified endogenous ACE2 locus encoding a recombinant ACE2 protein that comprises in operable linkage:

(i) an ACE2 signal sequence of a rodent ACE2 protein set forth in SEQ ID NO: 26;

(ii) an extracellular domain of a human ACE2 protein set forth in SEQ ID NO: 27;

(iii) a transmembrane domain of a rodent ACE2 protein set forth in SEQ ID NO: 28; and (iv) a cytoplasmic domain of a rodent ACE2 protein set forth in SEQ ID NO: 29.

14. The rodent cell of claim 10, wherein the rodent cell is an alveolar cell of the lung, an esophagus upper and stratified epithelial cell, an absorptive enterocyte from the ileum or colon, a cholangiocyte, a myocardial cell, a kidney proximal tubule cell, or a bladder urothelial cell.

* * * * *